United States Patent
Ando et al.

(10) Patent No.: US 8,653,063 B2
(45) Date of Patent: Feb. 18, 2014

(54) N-SUBSTITUTED SATURATED HETEROCYCLIC SULFONE COMPOUNDS WITH CB2 RECEPTOR AGONISTIC ACTIVITY

(75) Inventors: Kazuo Ando, Aichi (JP); Yasuhiro Iwata, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 322 days.

(21) Appl. No.: 13/145,439

(22) PCT Filed: Jan. 22, 2010

(86) PCT No.: PCT/JP2010/000377
§ 371 (c)(1), (2), (4) Date: Jul. 20, 2011

(87) PCT Pub. No.: WO2010/084767
PCT Pub. Date: Jul. 29, 2010

(65) Prior Publication Data
US 2011/0281840 A1    Nov. 17, 2011

Related U.S. Application Data

(60) Provisional application No. 61/202,036, filed on Jan. 22, 2009, provisional application No. 61/213,977, filed on Aug. 4, 2009.

(51) Int. Cl.
*C07D 401/14* (2006.01)
*A61K 31/4184* (2006.01)
*C07D 401/12* (2006.01)
*A61K 31/4545* (2006.01)
*A61P 9/10* (2006.01)
*A61P 3/10* (2006.01)
*A61P 31/18* (2006.01)
*A61P 29/00* (2006.01)
*A61P 1/08* (2006.01)
*A61P 11/06* (2006.01)
*A61P 1/04* (2006.01)
*A61P 11/00* (2006.01)

(52) U.S. Cl.
USPC ............ 514/210.21; 514/318; 514/210.8; 514/394; 546/199; 548/306.1

(58) Field of Classification Search
USPC .......... 546/199; 548/306.1; 514/210.8, 318, 514/322, 210.21, 394
See application file for complete search history.

(56) References Cited

U.S. PATENT DOCUMENTS 5,972,968 A * 10/1999 de Nanteuil et al. .......... 514/338
2006/0094750 A1    5/2006 Kon-I et al.

FOREIGN PATENT DOCUMENTS

| JP | 2008-518905 | 6/2008 |
| WO | 2007/102059 | 9/2007 |
| WO | 2008/003665 | 1/2008 |
| WO | 2009/077533 | 6/2009 |

OTHER PUBLICATIONS

Extended European Search Report (in English language) dated Jun. 1, 2012 in corresponding European Patent Application No. 10733374.2.
Verbist B M P et al: "5-Sulfonyl-benzimidazoles as selective CB2 agonists", Bioorganic & Medicinal Chemistry Letters, Pergamon, Elsevier Science, GB, vol. 18, No. 8, Apr. 15, 2008, pp. 2574-2579, XP022606350, ISSN: 0960-894X, DOI:10.1016/J.BMCL.2008.03.048 [retrieved on Mar. 20, 2008].
English translation of International Preliminary Report on Patentability and Written Opinion dated Jul. 26, 2011.
International Search Report issued Feb. 16, 2010 in International (PCT) Application No. PCT/JP2010/000377 along with the Written Opinion.

* cited by examiner

*Primary Examiner* — Niloofar Rahmani
(74) *Attorney, Agent, or Firm* — Wenderoth, Lind & Ponack, L.L.P.

(57) ABSTRACT

This invention relates to compounds of formula (I) or a pharmaceutically acceptable salt thereof, wherein X, $R^1$, $R^2$, $R^3$, $R^4$, $R^5$, $R^6$, $R^7$, k, m, n, p, q, r and s are each as described herein, and compositions containing such compounds, and the use of such compounds in the treatment of a condition mediated by CB2 receptor activity.

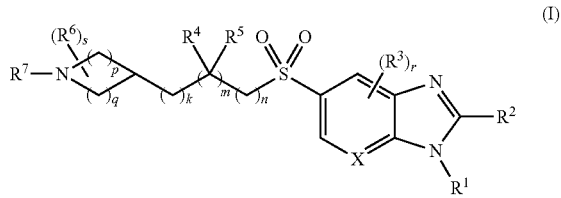

(I)

6 Claims, No Drawings

N-SUBSTITUTED SATURATED HETEROCYCLIC SULFONE COMPOUNDS WITH CB2 RECEPTOR AGONISTIC ACTIVITY

This application is a U.S. national stage of International Application No. PCT/JP2010/000377 filed Jan. 22, 2010, which claims the benefit of U.S. provisional application Ser. No. 61/202,036 filed Jan. 22, 2009 and Ser. No. 61/213,977 filed Aug. 4, 2009.

TECHNICAL FIELD

This invention relates to N-substituted saturated heterocyclic sulfone compounds. These compounds have CB2-selective receptor agonistic activity. The present invention also relates to a pharmaceutical composition, method of treatment and use, comprising the above compounds for the treatment of disease conditions mediated by CB2 receptor activity; in particular CB2 receptor agonistic activity.

BACKGROUND ART

Classical cannabinoids such as the marijuana derived cannabinoid (CB) delta$^9$-tetrahydro-cannabinol, (delta$^9$-THC) produce their pharmacological effects via interaction with specific cannabinoid receptors in the body. So far, two cannabinoid receptors have been characterized: CB1, a receptor found in the mammalian brain and peripheral tissues and CB2, a receptor found predominantly in the peripheral tissues. There is considerable interest in developing cannabinoid analogs that have selective CB2 agonistic activity since it is believed high selectivity for CB2 receptor may offer avenues for harnessing the beneficial effect of CB receptor agonists while avoiding the central adverse events seen with cannabinoid structures (see e.g. Expert Opin. Investig. Drugs (2007) 16(7):951-965).

In general, CB2 receptor agonists are found to be useful for the treatment of a variety of diseases, including inflammatory pain, nociceptive pain, neuropathic pain, fibromyalgia, chronic low back pain, visceral pain, rheumatoid arthritis, Crohn's disease, ulcerative colitis, asthma, dermatitis, seasonal allergic rhinitis, gastroesophageal reflux disease (GERD), constipation, diarrhea, functional gastrointestinal disorder, irritable bowel syndrome (IBS), cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, chronic obstructive pulmonary disease (COPD), cryptogenic fibrosing alveolitis and bronchitis (see J Pharmacol Exp Ther. 2004 February; 308(2):446-53; Proc Natl Acad Sci USA. 2003 Sep. 2; 100(18):10529-33; Br J Pharmacol. 2004 August; 142(8): 1247-54).

WO 2006/048754, WO 2007/102059, WO 2008/003665, and WO 2008/119694 disclose sulfonyl compounds as CB2 agonists. WO 2006/048754 formally discloses a heterocyclyl group on the sulfonyl group. WO 2007/102059 is not disclosed heterocyclic moiety on the sulfonyl group. WO 2008/003665 and WO 2008/119694 only disclose aryl or heteroaryl moiety on the sulfonyl group.

SUMMARY OF INVENTION

Technical Problem

There is a need to provide new CB2 agonists that can be a good drug. They should be well absorbed from the gastrointestinal tract, be metabolically stable and possess favorable pharmacokinetic properties. They should be non-toxic. Furthermore, the ideal drug candidate will exist in a physical form that is stable, non-hygroscopic and easily formulated. In particular, it has been desired that compounds must bind potently to the CB2 receptor whilst showing little affinity for other receptors especially CB1 and show functional activity as agonists. As the selectivity of CB2 and CB1 has not been enough in the prior art (WO 2006/048754), the undesirable side effects such as CNS excitation, memory impairment, dependence, hypothermia would be anticipated. The present invention provides novel compounds which have excellent CB2 agonistic activities with excellent selectivity against CB1.

Solution to Problem

Although sulfonyl compounds as CB2 agonists with a heterocyclyl group have been disclosed in the prior art, no compounds have enough selectivity between CB2 and CB1. The inventors have discovered that introducing appropriate substituents at the terminal nitrogen of saturated heterocyclic ring surprisingly gives an excellent selectivity of CB1 and CB2 with having excellent CB2 receptor agonistic activity.

In this invention, it has now been found out that a new class of N-substituted saturated heterocyclic sulfone compounds show CB2 agonistic activity with little affinity for CB1. The compounds have favorable properties as commercially available drug candidates, and thus are useful for the treatment of disease conditions mediated by CB2 activity such as inflammatory pain, nociceptive pain, neuropathic pain, fibromyalgia, chronic low back pain, visceral pain, acute cerebral ischemia, pain, chronic pain, acute pain, post herpetic neuralgia, neuropathies, neuralgia, diabetic neuropathy, HIV-related neuropathy, nerve injury, rheumatoid arthritic pain, osteoarthritic pain, back pain, cancer pain, dental pain, neuritis, sciatica, inflammation, neurodegenerative disease, cough, broncho constriction, irritable bowel syndrome (IBS), inflammatory bowel disease (IBD), colitis, cerebrovascular ischemia, emesis such as cancer chemotherapy-induced emesis, rheumatoid arthritis, Crohn's disease, ulcerative colitis, asthma, dermatitis, seasonal allergic rhinitis, GERD, constipation, diarrhea, functional gastrointestinal disorders, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, COPD, cryptogenic fibrosing alveolitis and bronchitis (hereinafter, referred as 'CB2 Diseases').

The present invention provides a compound of the following formula (I):

[Chem.1]

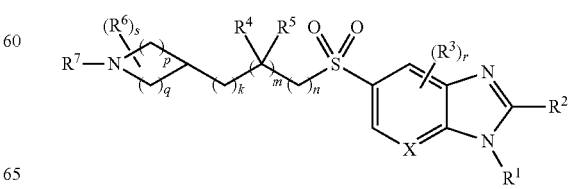

wherein

X is carbon or nitrogen;

$R^1$ is $C_1$-$C_4$ alkyl optionally substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl) amino, cycloalkyl, alkyl-substituted cycloalkyl, hydroxy-substituted cycloalkyl, amino-substituted cycloalkyl, heterocyclyl, alkyl-substituted heterocyclyl, acyl-substituted heterocyclyl and hydroxy-substituted heterocyclyl;

$R^2$ is hydrogen, cycloalkyl, alkyl-substituted cycloalkyl, $C_3$-$C_{10}$ alkyl, alkoxy-substituted $C_3$-$C_{10}$ alkyl or $C_1$-$C_2$ alkyl; said $C_1$-$C_2$ alkyl is optionally substituted with 1 to 2 substituents independently selected from the group consisting of cycloalkyl and alkyl-substituted cycloalkyl;

$R^3$ is halogen, hydroxy, $C_1$-$C_4$ alkyl or $C_1$-$C_4$ alkoxy;

$R^4$ and $R^5$ are independently selected from the group consisting of hydrogen, halogen, hydroxy, $C_1$-$C_4$ alkyl and $C_1$-$C_4$ alkoxy; or alternatively $R^4$ and $R^5$ form a 3 to 6 membered ring;

$R^6$ is $C_1$-$C_4$ alkyl, halogen, hydroxy, hydroxy $C_1$-$C_4$ alkyl, $R^aR^bN$—$C_1$-$C_4$ alkyl, —$CONR^aR^b$, —$CO_2C_1$-$C_4$ alkyl or $C_1$-$C_4$ alkoxy, said $C_1$-$C_4$ alkyl is optionally substituted with 1 to 2 substituents independently selected from the group consisting of cycloalkyl and alkyl-substituted cycloalkyl; said $R^a$ and $R^b$ are independently selected from hydrogen, $C_1$-$C_4$ alkyl and cycloalkyl; said $C_1$-$C_4$ alkyl is optionally substituted with hydroxylamino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; or alternatively $R^a$ and $R^b$ together with nitrogen atom to which they are attached form a 5 to 6 membered ring;

k, m and n are independently selected from 0, 1 and 2;

p and q are independently selected from 0, 1, 2, 3 and 4;

r is independently selected from 0, 1, 2 and 3; when r is two or more than two, $R^3$ may be same or different;

s is independently selected from 0, 1, 2, 3 and 4; when s is two or more than two, $R^6$ may be same or different;

$R^7$ is $C_1$-$C_4$ alkyl, cycloalkyl, hydroxy $C_1$-$C_4$ alkyl, $R^aR^bN$—$C_1$-$C_4$ alkyl, —CO—$NR^aR^b$, —CO—($C_1$-$C_4$ alkyl), —$SO_2$—$NR^aR^b$, —$SO_2$—($C_1$-$C_4$ alkyl), heterocycle ring, or —CO-heterocycle ring;

said $C_1$-$C_4$ alkyl is optionally substituted with 1 to 2 substituents independently selected from the group consisting of $C_1$-$C_4$ alkyl, hydroxy, trifluoromethyl, trifluoromethoxy, $C_1$-$C_4$ alkoxy, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl;

said $R^a$ and $R^b$ are independently selected from hydrogen, $C_1$-$C_4$ alkyl, cycloalkyl, and —CO—$C_1$-$C_4$ alkyl; or alternatively $R^a$ and $R^b$ together with nitrogen atom to which they are attached form a 4 to 6 membered ring which may containing N or O;

or a pharmaceutically acceptable salt thereof.

The compounds of the present invention differ structurally from the cited arts known compounds by the presence of a saturated heterocyclic moiety. In addition the compounds of the present invention are characterized by introducing a substituent to the terminal nitrogen atom of the saturated heterocyclic moiety.

Also, the present invention provides the use of a compound of formula (I) or a pharmaceutically acceptable salt thereof, each as described herein, for the manufacture of a medicament for the treatment of a condition mediated by CB2 receptor activity; in particular, CB2 agonistic activity.

Preferably, the present invention also provides the use of a compound of formula (I) or a pharmaceutically acceptable salt thereof, each as described herein, for the manufacture of a medicament for the treatment of diseases selected from CB2 Diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Further, the present invention provides a method of treatment of a condition mediated by CB2 receptor activity, in a mammalian subject, which comprises administering to a mammal in need of such treatment a therapeutically effective amount of a compound of formula (I) or a pharmaceutically acceptable salt thereof, each as described herein.

Examples of conditions mediated by CB2 receptor activity include, but are not limited to, CB2 Diseases.

Advantageous Effects of Invention

The compounds of the present invention show the CB2 receptor agonistic activity with excellent selectivity against CB1. The compounds of the present invention may show less toxicity, good absorption, distribution, good solubility, less protein binding affinity other than CB2 receptor, less drug-drug interaction, and good metabolic stability.

DESCRIPTION OF EMBODIMENTS

In the compounds (described in formula (I)) of the present invention:

Where X is carbon or nitrogen.

$R^1$ is $C_1$-$C_4$ alkyl optionally substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl) amino, cycloalkyl, alkyl-substituted cycloalkyl, hydroxy-substituted cycloalkyl, amino-substituted cycloalkyl, heterocyclyl, alkyl-substituted heterocyclyl, acyl-substituted heterocyclyl and hydroxy-substituted heterocyclyl;

of these, $C_1$-$C_4$ alkyl optionally substituted with 1 to 2 substituents independently selected from the group consisting of $C_1$-$C_4$ alkyl, hydroxy, trifluoromethoxy, $C_1$-$C_4$ alkylamino, di($C_1$-$C_4$ alkyl)amino, cycloalkyl, alkyl-substituted heterocyclyl, acyl-substituted heterocyclyl and hydroxy-substituted heterocyclyl is preferred for the substituent of $R^1$;

$C_1$-$C_4$ alkyl optionally substituted with 1 to 2 substituents independently selected from the group consisting of methyl, ethyl, propyl, isopropyl, butyl, isobutyl, secbutyl, tert-butyl, hydroxyl, cyclopropyl, cyclobutyl, trifluoromethoxy, methylamino, ethylamino, propylamino, isopropylamino, tert-butylamino, cyclopropylamino, dimethylamino, diethylamino, ethylmethylamino, dipropylamino, pyrrolidin-1-yl, cycloalkyl, N-methylpiperidinyl, N-acetylpiperidinyl and hydroxytetrahydropyranyl is more preferred for the substituent of $R^1$.

Where $R^2$ is hydrogen, cycloalkyl, alkyl-substituted cycloalkyl, $C_3$-$C_{10}$ alkyl, alkoxy-substituted $C_3$-$C_{10}$ alkyl or $C_1$-$C_2$ alkyl; said $C_1$-$C_2$ alkyl is optionally substituted with 1 to 2 substituents independently selected from the group consisting of cycloalkyl and alkyl-substituted cycloalkyl. Of these, $R^2$ is cycloalkyl, alkyl-substituted cycloalkyl, $C_1$-$C_7$ alkyl, said $C_1$-$C_7$ alkyl being substituted with 1 to 2 substituents independently selected from the group consisting of cycloalkyl and alkyl-substituted cycloalkyl is preferred for the substituent of $R^2$;

tertbutyl, neopentyl is more preferred for the substituent of $R^2$.

Where $R^3$ is halogen, hydroxy, $C_1$-$C_4$ alkyl or $C_1$-$C_4$ alkoxy; of these, hydrogen, fluorine, chlorine, methyl, or ethyl is preferred for the substituent of $R^3$.

Where $R^4$ and $R^5$ are independently selected from the group consisting of hydrogen, halogen, hydroxy, $C_1$-$C_4$ alkyl and $C_1$-$C_4$ alkoxy; or alternatively $R^4$ and $R^5$ form a 3 to 6 membered ring; of these, $R^4$ and $R^5$ are independently selected from the group consisting of hydrogen, methyl and ethyl; or alternatively $R^4$ and $R^5$ form a 3 to 5 membered ring is preferred for the substituent of $R^4$ and $R^5$.

Where $R^6$ is $C_1$-$C_4$ alkyl, halogen, hydroxy, hydroxy $C_1$-$C_4$ alkyl, $R^aR^bN$—$C_1$-$C_4$ alkyl, —$CONR^aR^b$, —$CO_2C_1$-$C_4$ alkyl or $C_1$-$C_4$ alkoxy, said $C_1$-$C_4$ alkyl is optionally substituted with 1 to 2 substituents independently selected from the group consisting of cycloalkyl and alkyl-substituted cycloalkyl; said $R^a$ and $R^b$ are independently selected from hydrogen, $C_1$-$C_4$ alkyl and cycloalkyl; said $C_1$-$C_4$ alkyl is optionally substituted with hydroxylamino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; or alternatively $R^a$ and $R^b$ together with nitrogen atom to which they are attached form a 5 to 6 membered ring; of these, methyl, ethyl, hydroxymethyl, —$CONH_2$, or —$CO_2methyl$ is preferred for $R^6$.

Where k, m and n are independently selected from 0, 1 and 2; of these, independently 0 or 1 is preferred for k, m and n.

Where p and q are independently selected from 0, 1, 2, 3 and 4; of these, independently 1 or 2 is preferred for p and q; of these, p=1, q=1 or p=2, q=2 is more preferred for p and q.

Where r is independently selected from 0, 1, 2 and 3; of these, 0 or 1 is preferred for r.

Where s is independently selected from 0, 1, 2, 3 and 4; of these, 0, 1, 2 or 3 is preferred for s.

Where $R^7$ is $C_1$-$C_4$ alkyl, cycloalkyl, hydroxy $C_1$-$C_4$ alkyl, $R^aR^bN$—$C_1$-$C_4$ alkyl, —$CO$—$NR^aR^b$, —$CO$—($C_1$-$C_4$ alkyl), —$SO_2$—$NR^aR^b$, —$SO_2$—($C_1$-$C_4$ alkyl), heterocycle ring, or —$CO$-heterocycle ring;

said $C_1$-$C_4$ alkyl is optionally substituted with 1 to 2 substituents independently selected from the group consisting of $C_1$-$C_4$ alkyl, hydroxy, trifluoromethyl, trifluoromethoxy, $C_1$-$C_4$ alkoxy, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl;

said $R^a$ and $R^b$ are independently selected from hydrogen, $C_1$-$C_4$ alkyl, cycloalkyl, and —$CO$—$C_1$-$C_4$ alkyl; or alternatively $R^a$ and $R^b$ together with nitrogen atom to which they are attached form a 4 to 6 membered ring which may containing N or O; of these, methyl, ethyl, propyl, isopropyl, butyl, isobutyl, sec-butyl, tert-butyl, hydroxyl, cyclopropyl, cyclobutyl, hydroxyethyl, 1-methylhydroxyethyl, 1,1-dimethylhydroxyethyl, dimethylaminoetyhyl, methylaminoethyl, —$CONH_2$, —$CONH$ $C_1$-$C_4$ alkyl, —$CO$ $NR^aR^b$, —$SO_2$—$NH_2$, —$SO_2$—$NHCH_3$, —$SO_2$—$N(CH_3)_2$, —$SO_2$—$CH_3$, —$SO_2$—$C_2H_5$, heterocycle ring, or —$CO$-heterocycle ring; said $C_1$-$C_4$ alkyl is optionally substituted with 1 to 2 substituents independently selected from the group consisting of $C_1$-$C_4$ alkyl, hydroxy, trifluoromethyl, trifluoromethoxy, and $C_1$-$C_4$ alkoxy; is preferred for $R^7$.

The term "heterocyclyl", as used herein, is preferably a 5 to 7 membered heterocyclyl having 1 to 3 heteroatoms such as O, N, or/and S and is exemplified by pyridynyl, pyrazolyl, imidazolyl, triazolyl, oxazolyl, oxolanyl, oxanyl, pyrrolidinyl, imidazolidinyl, 2-oxoimidazolidinyl, or 2-oxopyrrolidinyl.

The term "cycloalkyl", as used herein, preferably a cycloalkyl group having 3 to 8 carbon atoms and is exemplified by cyclobutyl, cyclopentyl or cyclohexyl.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition. As used herein, the article "a" or "an" refers to both the singular and plural form of the object to which it refers unless indicated otherwise.

One embodiment of the invention provides a compound selected from the group consisting of:

3-(1-(2-(dimethylamino)ethyl)-2-neopentyl-1H-benzo[d]imidazol-5-ylsulfonyl)azetidine-1-carboxamide;

3-(1-(2-hydroxy-2-methylpropyl)-2-neopentyl-1H-benzo[d]imidazol-5-ylsulfonyl)azetidine-1-carboxamide;

3-((1-(cyclopropylmethyl)-2-neopentyl-1H-benzo[d]imidazol-5-ylsulfonyl)methyl)azetidine-1-carboxamide;

1-(cyclopropylmethyl)-5-((1-(methylsulfonyl)azetidin-3-yl)methylsulfonyl)-2-neopentyl-1H-benzo[d]imidazole;

1-(cyclopropylmethyl)-2-neopentyl-5-(((1-(pyridin-4-yl)piperidin-4-yl)methylsulfonyl)-1H-benzo[d]imidazole;

2-tert-butyl-1-(cyclopropylmethyl)-5-((1-(methylsulfonyl)piperidin-4-yl)methylsulfonyl)-1H-benzo[d]imidazole;

5-(1-(methylsulfonyl)azetidin-3-ylsulfonyl)-2-neopentyl-1-(2-(trifluoromethoxy)ethyl)-1H-benzo[d]imidazole;

3-(2-neopentyl-1-(2-(trifluoromethoxy)ethyl)-1H-benzo[d]imidazol-5-ylsulfonyl)azetidine-1-carboxamide;

1-(4-(1-(cyclopropylmethyl)-2-neopentyl-1H-benzo[d]imidazol-5-ylsulfonyl)-4-(hydroxymethyl)piperidin-1-yl)ethanone;

(4-(1-(cyclopropylmethyl)-2-neopentyl-1H-benzo[d]imidazol-5-ylsulfonyl)-1-(methylsulfonyl)piperidin-4-yl)methanol;

4-[2-(2,2-dimethylpropyl)-1-[(4-hydroxyoxan-4-yl)methyl]-1H-1,3-benzo[d]imidazole-5-sulfonyl]piperidine-1-carboxamide;

4-(4-((1-(cyclopropylmethyl)-2-neopentyl-1H-benzo[d]imidazol-5-ylsulfonyl)methyl)piperidine-1-carbonyl)imidazolidin-2-one;

bis(4-{[1-(cyclopropylmethyl)-2-(2,2-dimethylpropyl)-1H-1,3-benzodiazole-5-sulfonyl]methyl}piperidine-1-sulfonamide);

3-(1-((1-acetylpiperidin-4-yl)methyl)-2-neopentyl-1H-benzo[d]imidazol-5-ylsulfonyl)azetidine-1-carboxamide;

1-(cyclopropylmethyl)-2-(2,2-dimethylpropyl)-5-{[(1-methanesulfonylpiperidin-4-yl)methane]sulfonyl}-1H-1,3-benzodiazole;

1-(4-{[1-(cyclopropylmethyl)-2-(2,2-dimethylpropyl)-1H-1,3-benzodiazole-5-sulfonyl]methyl}piperidin-1-yl)ethan-1-one;

1-(cyclopropylmethyl)-2-(2,2-dimethylpropyl)-5-(1-methanesulfonylazetidine-3-sulfonyl)-1H-1,3-benzodiazole;

(3S)-3-[1-(cyclopropylmethyl)-2-(2,2-dimethylpropyl)-1H-1,3-benzodiazole-5-sulfonyl]pyrrolidine-1-carboxamide;

N,N-dimethyl-2-(5-(1-(methylsulfonyl)azetidin-3-ylsulfonyl)-2-neopentyl-1H-benzo[d]imidazol-1-yl)ethanamine citrate;

(4-((1-(2-(dimethylamino)ethyl)-2-neopentyl-1H-benzo[d]imidazol-5-ylsulfonyl)methyl)piperidin-1-yl)(1H-pyrazol-4-yl)methanone hydrochloride;
  (S)-N,N-dimethyl-2-(5-(1-methylpyrrolidin-3-ylsulfonyl)-2-neopentyl-1H-benzo[d]imidazol-1-yl)ethanamine dihydrochloride;
  2-(5-(1-ethylazetidin-3-ylsulfonyl)-2-neopentyl-1H-benzo[d]imidazol-1-yl)-N,N-dimethylethanamine;
  2-(3-(1-(2-(dimethylamino)ethyl)-2-neopentyl-1H-benzo[d]imidazol-5-ylsulfonyl)azetidin-1-yl)ethanol; and
  (R)-N,N-dimethyl-2-(5-(1-methylpyrrolidin-3-ylsulfonyl)-2-neopentyl-1H-benzo[d]imidazol-1-yl)ethanamine dihydrochloride;
or a pharmaceutically acceptable salt thereof.

Pharmaceutically acceptable salts of a compound of formula (I) include the acid addition (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci. 64 (8), 1269-1288 by Haleblian (August 1975).

Hereinafter all references to a compound of formula (I) include references to salts and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric and tautomeric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985). Some examples of prodrugs in accordance with the invention include:
  (i) where the compound of formula (I) contains an alcohol functionality (—OH), an ether thereof, for example, replacement of the hydrogen with $(C_1-C_6)$alkanoyloxymethyl; and
  (ii) where the compound of formula (I) contains a primary or secondary amino functionality (—$NH_2$ or —NHR where R is not H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I). Compounds of formula (I) containing one or more asymmetric carbon atoms can exist as two or more stereoisomers. Where the compound contains, for example, a keto or oxime group or an aromatic moiety, tautomeric isomerism ('tautomerism') can occur. It follows that a single compound may exhibit more than one type of isomerism. Included within the scope of the present invention are all stereoisomers, geometric isomers and tautomeric forms of the compounds of formula (I), including compounds exhibiting more than one type of isomerism, and mixtures of one or more thereof. Also included are acid addition salts wherein the counterion is optically active, for example, D-lactate or L-lysine, or racemic, for example, DL-tartrate or DL-arginine. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^2$H, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to F. The following Methods illustrate the preparation of compounds of formula (I). Unless otherwise indicated, $R^1$, $R^2$, $R^3$, $R^4$, $R^5$, $R^6$, $R^7$, $R^a$, $R^b$, X, k, m, n, p, q, r and s in the following Methods are as defined above. All starting materials in the following general syntheses may be commercially available or obtained by conventional methods known to those skilled in the art, such as Journal of Organic Chemistry. 48(4), 604-5; 1983, Canadian Journal of Chemistry, 62(8), 1544-7; 1984, Chemical & Environmental Research. 11 (1 & 2), 63-75; 2002, and Chemical & Pharmaceutical Bulletin. 38(10), 2853-8; 1990, Reactions and Syntheses in the Organic Chemistry Laboratory edited by Lutz-Friedjan Tietze, Theophil Eicher (Univ Science Books) and the disclosures of which are incorporated herein by references.

Method A

This illustrates the preparation of compounds of formula (I).

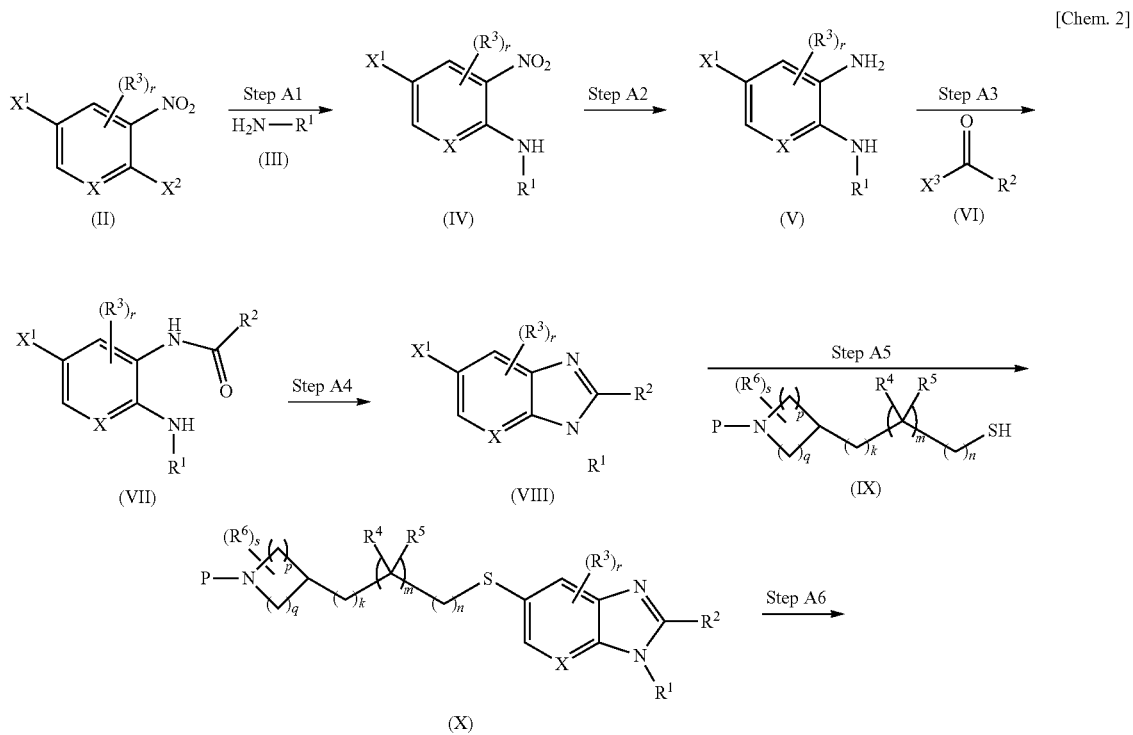

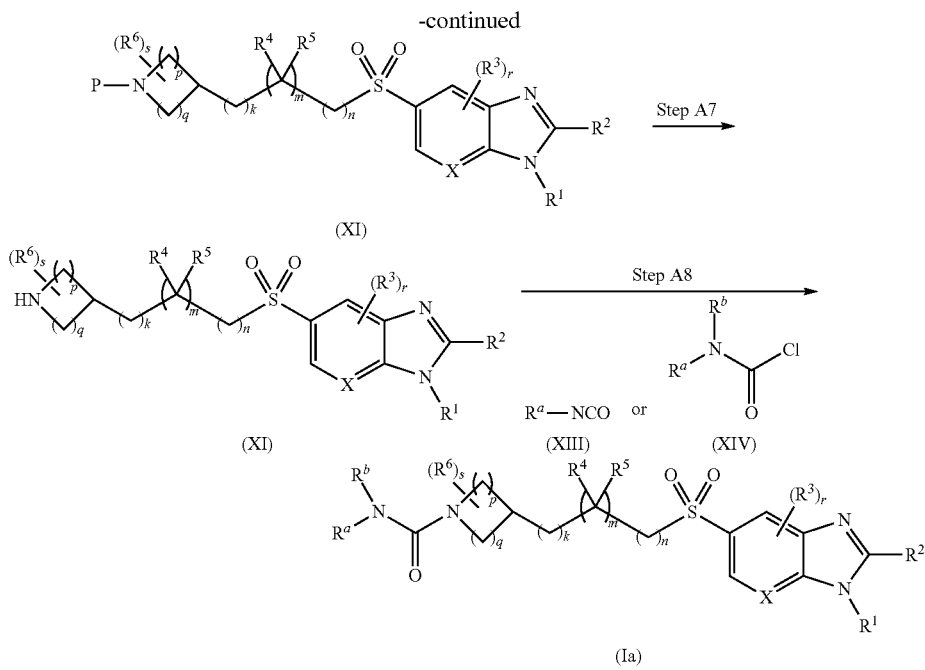

In Reaction Scheme $R^1$, $R^2$, $R^3$, $R^4$, $R^5$, $R^6$, $R^7$, $R^a$, $R^b$, X, k, m, n, p, q, r and s are as defined above. $X^1$, $X^2$ and $X^3$ are a halogen atom, preferably bromine or iodine for $X^1$, fluorine or chlorine for $X^2$, and chlorine for X. P is a Protecting group of NH, such as tert-butyloxycarbonyl, benzyloxycarbonyl, benzyl, preferably tert-butylcarbonyl.

Step A1

In this step, the compound of formula (IV) is prepared by reaction of the compound of formula (II) with the compound of formula (III). Both compounds of formula (II) and formula (III) are commercially available or can be obtained by conventional methods known to those skilled in the art.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; and sulfoxides, such as dimethyl sulfoxide and sulfolane. Of these solvents, alcohols are preferred; ethanol is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

In this reaction, microwave can be employed to accelerate the reaction. In the case of employing microwave, the reaction at a temperature may be from about 0° C. to about 160° C. and the reaction time from about 5 minutes to about 12 hours will usually suffice.

Step A2

In this step, the compound of formula (V) is prepared by reduction of the nitro group of the compound of formula (IV).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aromatic hydrocarbons, such as benzene and toluene; alcohols, such as methanol, ethanol, propanol, 2-propanol and butanol; and esters, such as ethyl acetate. Of these solvents, methanol and ethanol are preferred.

The reaction is carried out in the presence of a reducing agent. There is likewise no particular restriction on the nature of the reducing agents used, and any reducing agent commonly used in reactions of this type may equally be used here. Examples of such reducing agents include a combination of hydrogen gas and a catalyst such as palladium-carbon, platinum-carbon, platinum on sulfide carbon and Raney nickel; a combination of iron and ammonium chloride and a combination of zinc and hydrochloric acid. In the case of employing platinum on carbon, the pressure of hydrogen gas preferably range from about 1 atom to about 4 atom. Of these, a combination of hydrogen gas and platinum on sulfide carbon or a combination of iron and ammonium chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step A3

In this step, the compound of formula (VII) is prepared by amidation of the compound of formula (V) with the compound of formula (VI), which is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; amides, such as formamide, N,N-dimethylformamide, N,N-dimethylacetamide and hexamethylphosphoric triamide; nitriles, such as acetonitrile and benzonitrile; and esters, such as ethyl acetate and methyl acetate. Of these solvents, esters are preferred; ethyl acetate is more preferred. The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step A4

In this step, the desired compound of formula (VIII) is prepared by the cyclization of the compound of formula (VII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aromatic hydrocarbons, such as benzene, toluene and nitrobenzene; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; and esters, such as ethyl acetate and methyl acetate. Of these solvents, alcohols and aromatic hydrocarbons are preferred; methanol, ethanol, propanol, 2-propanol, butanol and toluene are more preferred. The reaction is carried out in the presence of an acid or base. There is likewise no particular restriction on the nature of the acids or bases used, and any ones commonly used in reactions of this type may equally be used here. Examples of such acids or bases include: acids, such as hydrochloric acid, sulfuric acid, or p-toluenesulfonic acid; and alkali metal hydroxides, such as lithium hydroxide, sodium hydroxide and potassium hydroxide. Of these, p-toluenesulfonic acid and sodium hydroxide are preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

In this reaction, microwave can be employed to accelerate the reaction. In the case of employing microwave, the reaction at a temperature may be from about 0° C. to about 130° C. and the reaction time from about 5 minutes to about 12 hours will usually suffice.

Step A5

In this step, the desired compound of formula (X) is prepared by coupling reaction of the compound of formula (VIII) with the compound of formula (IX) under the presence of palladium catalyst. The compound of formula (IX) is commercially available or can be obtained by method F.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, ethers are preferred; dioxane is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step A6

In this step, the desired compound of formula (X1) is prepared by oxidation of the compound of formula (X).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; and aromatic hydrocarbons, such as benzene, toluene and nitrobenzene. Of these solvents, halogenated hydrocarbons are preferred; dichloromethane is more preferred.

The reaction is carried out in the presence of an oxidizing agent. There is likewise no particular restriction on the nature of the oxidizing agents used, and any oxidizing agent commonly used in reactions of this type may equally be used here. Examples of such oxidizing agents include: high valence iodine oxidizing agents, such as $NaIO_4$ or 1,1,1-triacetoxy-1, 1-dihydro-1,2-benziodoxol-3(1H)-one (Dess-Martin periodinane); or peracids, such as $H_2O_2$, $CH_3COOOH$ or m-chloroperbenzoic acid (mCPBA), a combination of $H_2O_2$ and a catalyst such as sodium tungstate. Of these, mCPBA or a combination of $H_2O_2$ and a catalyst such as sodium tungstate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step A7

In this step, the desired compound of formula (XII) is prepared by deprotection of the compound (XI). Typical amino-protecting groups and its cleavage reaction condition are described in "Protective Groups in Organic Synthesis" edited by T. W. Greene et al. (John Wiley & Sons, 1999).

Step A8

In this step, the compound of formula (Ia) is prepared by coupling reaction of the compound of formula (XII), which can be prepared as described in Step A7 with the compound of formula (XIII) or the compound of formula (XIV), both of which are commercially available or obtained by conventional methods known to those skilled in the art.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, halogenated hydrocarbons are preferred; dichloromethane is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method B

This illustrates the preparation of compounds of formula (Ib).

Reaction scheme B

[Chem. 3]

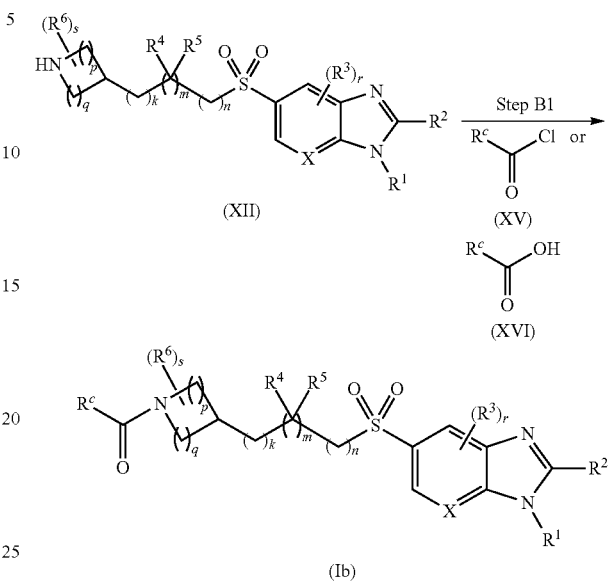

$R^c$ is a $C_1$-$C_4$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl. The compound of formula (XII) can be prepared as described in Step A7.

Step B1

In this step, the desired compound of formula (Ib) is prepared by the amidation ((XV) is used) or coupling ((XVI) is used) reaction of the compound of formula (XII).

Amidation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; and N,N-diethylamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, halogenated hydrocarbons are preferred; dichloromethane is more preferred.

The reaction is normally and preferably effected in the presence of amines, such as N-methylmorpholine, triethylamine, tripropylamine, tributylamine, diisopropylethylamine, dicyclohexylamine, N-methylpiperidine, pyridine, 4-pyrrolidinopyridine and N,N-dimethylaniline. Of these amine, triethylamine is preferred;

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Coupling Reaction

The reaction is normally and preferably effected in the presence of solvent. There is no particular restriction on the nature of the solvent to be employed, provided that it has no adverse effect on the reaction or the reagents involved and that it can dissolve reagents, at least to some extent.

Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide and N,N-dimethylacetamide; ethers, such as diethyl ether diisopropyl ether and tetrahydrofurane; and nitriles, such as acetonitrile and benzonitrile. Of these solvents, ethers are preferred; tetrahydrofuran is more preferred.

The reaction is carried out in the presence of a condensing agent.

There is likewise no particular restriction on the nature of the condensing agents used, and any condensing agent commonly used in reactions of this type may equally be used here. Examples of such condensing agents include: azodicarboxylic acid di-lower alkyl ester-triphenylphosphines, such as diethyl azodicarboxylate-triphenylphosphine; 2-halo-1-lower alkyl pyridinium halides, such as 2-chloro-1-methy pyridinium iodide; diarylphosphorylazides, such as diphenylphosphorylazide (DPPA); chloroformates, such as ethyl chloroformate and isobutyl chloroformate; phosphoryl chlorides, such as diethyl phosphoryl chloride; phosphorocyanidates, such as diethyl phosphorocyanidate (DEPC); imidazole derivatives, such as N,N'-carbonyldiimidazole (CDI); carbodiimide derivatives, such as N,N'-dicyclohexylcarbodiimide (DCC) and 1-ethyl-3-(3-dimethylaminopropyl)carbodiimide hydrochloride (EDAPC); and sulfonyl chloride derivatives, such as 2,4,6-triisopropylbenzenesulfonyl chloride, Reagents, such as N-hydroxysuccinimide (HONSu), 3-hydroxy-4-oxo-3,4-dihydro-1,2,3-benztriazine (HOObt), 2-(1H-benzotriazole-1-yl)-1,1,3,3-tetramethyluronium hexafluorophosphate (HBTU) and N-hydroxybenztriazole (HOBt), may be employed for this step. Of these, HBTU is preferred.

The reaction may be carried out in the presence of base. There is likewise no particular restriction on the nature of the bases used, and any base commonly used in reactions of this type may equally be used here.

Examples of such bases include: amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Of these, triethylamine is preferred.

The reaction can take place over a wide range of temperatures, and the precise reaction temperature is not critical to the invention. The preferred reaction temperature will depend upon such factors as the nature of the solvent, and the starting materials.

However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method C

This illustrates the preparation of compounds of formula (Ic).

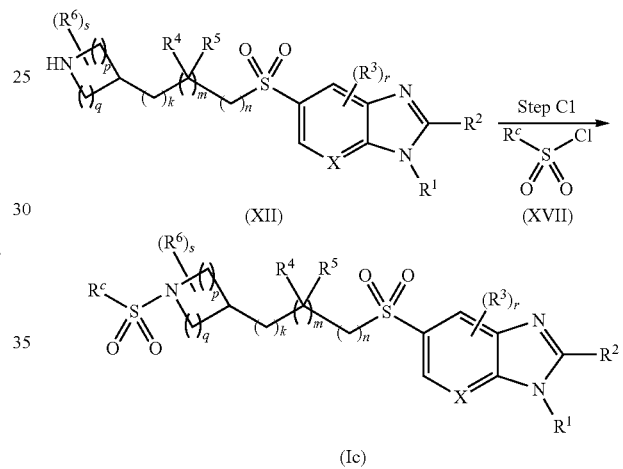

$R^c$ is a $C_1$-$C_4$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl. The compound of formula (XII) can be prepared as described in Step A7.

Step C1

In this step, the desired compound of formula (Ic) is prepared by the amidation of the compound of formula (XII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; and N,N-diethylamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, halogenated hydrocarbons are preferred; dichloromethane is more preferred.

The reaction is normally and preferably effected in the presence of amines, such as N-methylmorpholine, triethylamine, tripropylamine, tributylamine, diisopropylethylamine, dicyclohexylamine, N-methylpiperidine, pyridine, 4-pyrrolidinopyridine and N,N-dimethylaniline. Of these amine, triethylamine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method D

This illustrates the preparation of compound of formula (Id).

Reaction scheme D

[Chem. 5]

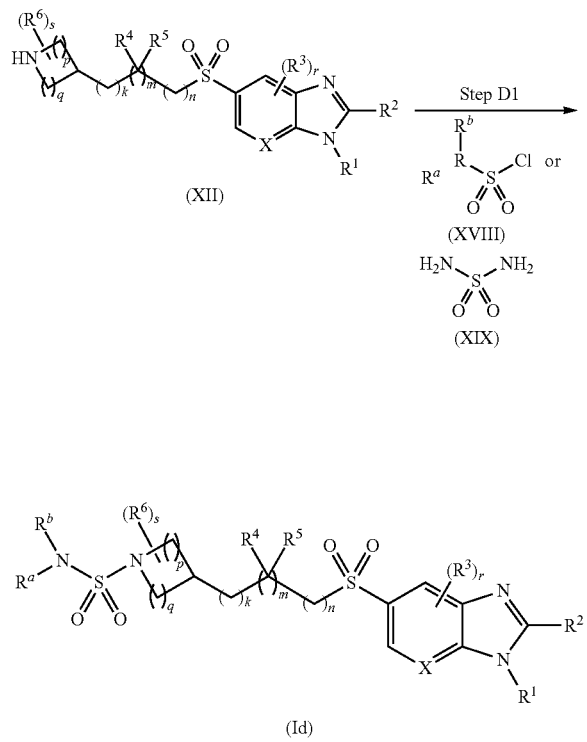

Step D1

In this step, the compound of formula (Id) is prepared by coupling reaction of the compound of formula (XII), which can be prepared as described in Step A7 with the compound of formula (XVIII) or the compound of formula (XIX), both of which are commercially available or obtained by conventional methods known to those skilled in the art.

Reaction with the Compound of Formula (XVIII)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, halogenated hydrocarbons are preferred; dichloromethane is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Reaction with the Compound of Formula (XIX)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; alcohols, such as methanol, ethanol, propanol, 2-propanol and butanol; nitriles, such as acetonitrile and benzonitrile; sulfoxides, such as dimethyl sulfoxide and sulfolane. Of these solvents, dioxane is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about room temperature to about 140° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method E

This illustrates the preparation of intermediate of formula (XII).

Reaction scheme E

[Chem. 6]

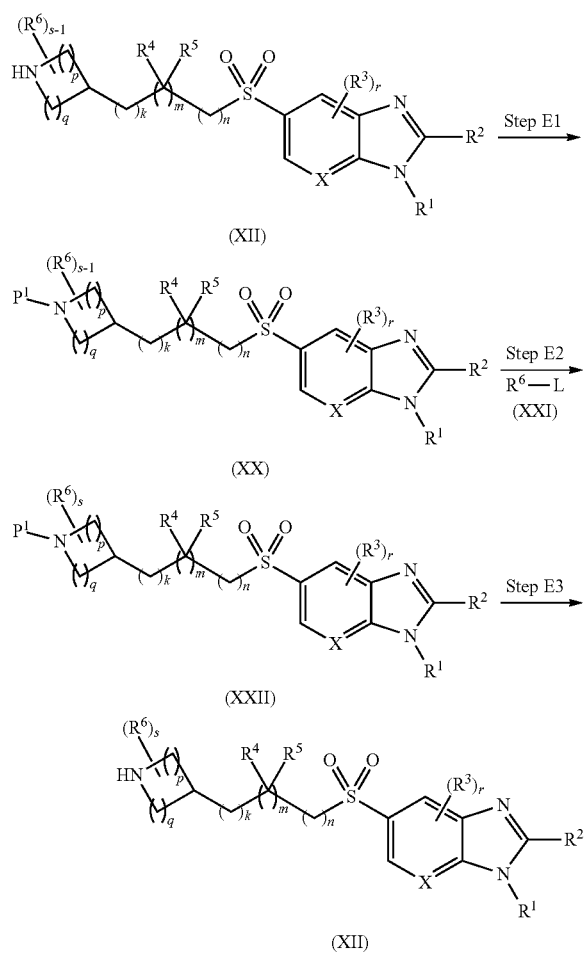

Step E1

In this step, the compound of formula (XX) is prepared by protecting group (P¹) insertion reaction of the compound of formula (XII), which can be prepared as described in Step A7.

Typical amino-protecting groups and its formation condition are described in "Protective Groups in Organic Synthesis" edited by T. W. Greene et al. (John Wiley & Sons, 1999). Of these protecting groups, triphenylmethyl group is preferred.

Step E2

In this step, the compound of formula (XXII) is prepared by coupling reaction of the compound of formula (XX), which can be prepared as described in Step E1 with the compound of formula (XXI) which is commercially available or obtained by conventional methods known to those skilled in the art. The term "L" as used "R⁶-L", is an appropriate leaving group, such as halogen, sulfonyl ester, cyanide.

This reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; strong basic amines, such as 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium diisopropyl amide, potassium diisopropyl amide, sodium diisopropyl amide, lithium bis(trimethylsiiyl) amide and potassium bis(trimethylsilyl)amide; alkyl lithium, such as methyl lithium, n-butyl lithium, sec-butyl lithium and tert-butyl lithium. Of these, alkali metal amides are preferred; lithium diisopropyl amide is preferred.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; ethers, such as diethyl ether, diisopropyl ether, tetrahydrofuran and dioxane; aromatic hydrocarbons, such as benzene and toluene; amides, such as N,N-dimethylformamide, N,N-dimethylacetamide and hexamethylphosphoric triamide; alcohols, such as methanol, ethanol, propanol, 2-propanol and butanol; sulfoxides, such as dimethyl sulfoxide and sulfolane. Of these solvents, ethers are preferred; tetrahydrofuran is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step E3

In this step, the desired compound of formula (XII) is prepared by deprotection of the compound (XI). Typical amino-protecting groups and its cleavage reaction condition are described in "Protective Groups in Organic Synthesis" edited by T. W. Greene et al. (John Wiley & Sons, 1999).

Method F

This illustrates the preparation of intermediate of formula (IX).

Reaction scheme F

[Chem. 7]

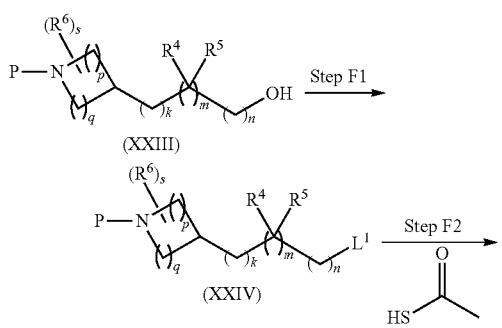

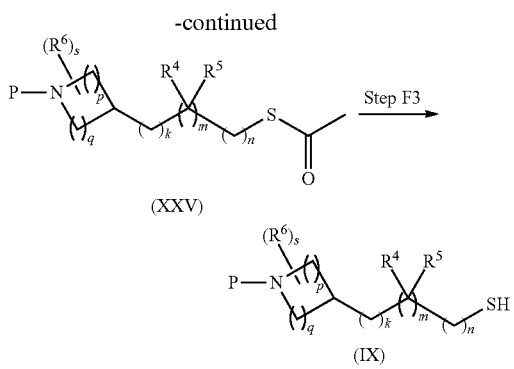

(XXV)

(IX)

In Reaction Scheme, $R^4$, $R^5$, $R^6$, k, m, n, p, q, r and s are as defined above. P is a Protecting group of NH, such as tert-butyloxycarbonyl, benzyloxycarbonyl, benzyl, preferably tert-butylcarbonyl. L is a leaving group, such as halogen and sulfonyl ester.

Step F1

In this step, the compound of formula (XXIV) is prepared by coupling reaction (when L is sulfonyl ester) or substitution reaction (when L is halogen) of the compound of formula (XXIII), which is commercially available or obtained by conventional methods known to those skilled in the art.

Coupling Reaction (When L is Sulfonyl Ester)

The reaction is normally and preferably effected in the presence of sulfonylation reagent, such as methanesulfonyl chloride, toluenesulfonyl chloride, benzenesulfonyl chloride, trifluoromethanesulfonyl anhydride, of these reagent, methanesulfonyl chloride are preferred.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; nitriles, such as acetonitrile and benzonitrile; and aliphatic hydrocarbons, such as hexane, heptane and petroleum ether. Of these solvents, halogenated hydrocarbons are preferred; dichloromethane is more preferred.

This reaction is carried out in the presence of a base. There is likewise no particular restriction on the nature of the bases used, and any base commonly used in reactions of this type may equally be used here. Examples of such bases include: amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0] non-5-ene (DBN), 1,4-diazabicyclo[2.2.2]octane (DABCO), 1,8-diazabicyclo[5.4.0]undec-7-ene (DBU), lutidine, and colidine. Of these, triethylamine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Substitution Reaction (When L is Halogen)

The reaction is carried out in the presence of a halogenated agent. There is likewise no particular restriction on the nature of the reducing agents used, and any halogenated agent commonly used in reactions of this type may equally be used here. Examples of such halogenated agents include a combination of halogen resource and a phosphorous reagent such as tetrabromocarbon and triphenylphosphine, tetrachlorocarbon and triphenylphosphine, iodine and triphenylphosphine; a hydrogen halide such as hydrogen bromide and hydrogen iodide, of these, a combination of hydrogen gas and platinum on sulfide carbon or a combination of iodine and triphenylphosphine is preferred.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aromatic hydrocarbons, such as benzene and toluene; aliphatic hydrocarbons, such as hexane, heptane and petroleum ether; halogenated hydrocarbons, such as dichloromethane, chloroform, carbon tetrachloride and 1,2-dichloroethane. Of these solvents, toluene is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step F2

In this step, the compound of formula (XXV) is prepared by substitution reaction of the compound of formula (XXIV).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; halogenated hydrocarbons, such as dichloromethane, chloroform, carbon tetrachloride and 1,2-dichloroethane; nitriles, such as acetonitrile and benzonitrile. Of these solvents, amides are preferred; N,N-dimethylformamide is more preferred.

This reaction is carried out in the presence of a base. There is likewise no particular restriction on the nature of the bases used, and any base commonly used in reactions of this type may equally be used here. Examples of such bases include: alkali metal alkoxides, such as sodium methoxide, sodium ethoxide, and potassium t-butoxide; alkali metal carbonates, such as lithium carbonate, sodium carbonate, potassium carbonate and cesium carbonate; strong basic amines, such as 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine. Of these, alkali metal carbonates are preferred; potassium carbonate and cesium carbonate are preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step F3

In this step, the compound of formula (IX) is prepared by hydrolysis reaction of the compound of formula (XXV).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: alcohols, such as methanol, ethanol, propanol, 2-propanol and butanol.

This reaction is carried out in the presence of a base. There is likewise no particular restriction on the nature of the bases used, and any base commonly used in reactions of this type may equally be used here. Examples of such bases include: alkali metal alkoxides, such as sodium methoxide, sodium ethoxide, and potassium t-butoxide; alkali metal carbonates, such as lithium carbonate, sodium carbonate, potassium carbonate and cesium carbonate; strong basic amines, such as 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine. Of these, alkali metal carbonates are preferred; potassium carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

The compounds of formula (I), and the intermediates above-mentioned preparation methods can be isolated and purified by conventional procedures, such as distillation, recrystallization or chromatographic purification. Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose. They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations. Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from about 1 wt % to about 25 wt %, preferably from about 5 wt % to about 20 wt % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet. Other possible ingredients include anti-oxidants, colorants, flavoring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line. 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PLGA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid. Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, super-critical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from about 1 microg to about 20 mg of the compound of the invention per actuation and the actuation volume may vary from about 1 microL to about 100 microL. A typical formulation may comprise a compound of formula (I), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 microg of the compound of formula (I). The overall daily dose will typically be in the range about 50 microg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in WO 91/11172, WO 94/02518 and WO 98/55148.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses. These dosages are based on an average human subject having a weight of about 65 kg to about 70 kg. The physician will readily be able to determine doses for subjects whose weight falls outside this range, such as infants and the elderly.

As discussed above, a compound of the invention exhibits CB2 agonist activity. A CB2 agonist of the present invention may be usefully combined with another pharmacologically active compound, or with two or more other pharmacologically active compounds, particularly in the treatment of the cancer, inflammatory diseases, immunomodulatory diseases and gastrointestinal disorder. For example, CB2 agonist, particularly a compound of the formula (I), or a pharmaceutically acceptable salt thereof, as defined above, may be administered simultaneously, sequentially or separately in combination with one or more agents selected from:

(i) 5-$HT_3$ antagonists, e.g. dolasetron, palonosetron, alosetron, azasetron and ramosetron, mitrazapine, granisetron, tropisetron, E-3620, ondansetron and indisetron;

(ii) 5-$HT_4$ agonists, e.g. tegaserod, mosapride, cinitapride and oxtriptane;

(iii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine Modulon (registered trademark) (trimebutine malate), Imodium (registered trademark) (loperamide) and pentazocine;

(iv) tricyclic antidepressants, e.g. imipramine, amitriptyline, clomipramine, amoxapine and lofepramine;

(v) somatostatin analogues, e.g. octreotide, AN-238 and PTR-3173;

(vi) anticholinergics, e.g. dicyclomine and hyoscyamine, ipratropium bromide, ipratropium, tiotropium bromide;

(vii) laxatives, e.g. Trifyba (registered trademark), Fybogel (registered trademark), Konsyl (registered trademark), Isogel (registered trademark), Regulan (registered trademark), Celevac (registered trademark) and Normacol (registered trademark);

(viii) fiber products, e.g. Metamucil (registered trademark);

(ix) antispasmodics, e.g.: mebeverine;

(x) dopamine antagonists, e.g. metoclopramide, domperidone and levosulpiride;

(xi) cholinergics, e.g. neostigmine, pilocarpine, carbachol;

(xii) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xiii) Cl Channel activator: e.g. lubiprostone;

(xiv) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and depoxetine;

(xv) GABA agonists, e.g. gabapentin, topiramate, cinolazepam, clonazepam, progabide, brotizolam, zopiclone, pregabalin and eszopiclone;

(xvi) tachykinin (NK) antagonists, particularly NK-3, NK-2 and NK-1 antagonists, e.g.: nepadutant, saredutant, talnetant, (R,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[1R)-1-[3,5-bis(trifluoromethyl)phenyl] ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl] methylamino]-2-phenyl-piperidine(2S,3S);

(xvii) alpha2 agonists, e.g. clonidine, medetomidine, lofexidine, moxonidine, tizanidine, guanfacine, guanabenz, talipexole and dexmedetomidine;

(xviii) benzodiazepine agonists, e.g. diazepam, zaleplon, Zolpidem, haloxazolam, clonazepam, prazepam, quazepam, flutazolam, triazolam, lormetazepam, midazolam, tofisopam, clobazam, flunitrazepam and flutoprazepam;

(xix) prostaglandin analogues, e.g. Prostaglandin, misoprostol, treprostinil, esoprostenol, latanoprost, iloprost, beraprost, enprostil, ibudilast and ozagrel;

(xx) histamine $H_3$ agonists, e.g. R-alpha-methylhistamine and BP-294;

(xxi) anti-gastric agents, e.g. Anti-gastrin vaccine, itriglumide and Z-360;

(xxii) disease modifying anti-rheumatic drugs (DMARDs), e.g. methotrexate, leflunomide, penicillamine aurothiopropanol sulfonate, sulfasalazine, mesalamine, olsalazine, balsalazide, Hylan G-F 20, glucosamine, chondroitin sulfate, hydro xychloroquine and diacerein;

(xxiii) Tumor Necrosis Factor-Alpha (TNF-alpha) modulators, e.g. etanercept, infliximab, adalimumab, CDP-870, pegsunercept, ISIS-104838.RDP-58 and thalidomide;

(xxiv) interleukin-based therapies, e.g. anakinra, atlizumab, RGN-303, denileukin-diftitox, ilodecakin, oprelvekin and mepolizumab;

(xxv) nonsteroidal antiinflammatory drugs (NSAIDs), e.g. piroxicam, naproxen, indomethacin, ibuprofen, diclofenac, ketorolac, flurbiprofen, aspirin, diflusinal, etodolac, fenbufen, fenoprofen, flufenisal, ketoprofen, meclofenamic acid, mefenamic acid, nabumetone, oxaprozin, phenylbutazone, sulindac, tolmetin and zomepirac;

(xxvi) selective COX-2 Inhibitors, e.g. celecoxib, rofecoxib, vaidecoxib, etoricoxib, lumiracoxib and LAS-34475;

(xxvii) Centrally Acting Analgesics, e.g. tramadol and oxymorphone ER;

(xxviii) immunosupressives, e.g. cyclosporine, tacrolimus, rapamycin, azathioprine and mycophenolate mofetil;

(xxix) Multiple Sclerosis(MS) treatments, e.g. interferon beta-1b, interferon beta-1a, glatiramer acetate, mitoxantrone, cyclophosphamide, MBP-8298, AG-284, tiplimotide, BX-471, E-2007, recombinant glial growth factor-2 and natalizumab;

(xxx) Monoclonal Antibodies, e.g. natalizumab, daclizumab, alemtuzumab, omalizumab, TNX-100 and SGN-40;

(xxxi) insulin secretagogues, e.g. glyburide, glipizide, repaglinide and glimepiride;

(xxxii) biguanides, e.g. metformin;

(xxxiii) alpha-glucosidase inhibitors, e.g. acarbose, voglibose and miglitol;

(xxxiv) PPAR gamma agonists, e.g. pioglitazone and rosiglitazone;

(xxxv) antibiotics, e.g. sulfacetamide, erythromycin, gentamicin, tobramycin, ciprofloxacin and ofloxacin;

(xxxvi) cell adhesion molecule inhibitors , e.g. alicaforsen, MLN-02, alefacept, efalizumab, R-411 and IVL-745;

(xxxvii) anti-allergy drugs, e.g. levocabastine, olopatadine, cromolyn, lodoxamide , pheniramine, ketotifen, mizolastine and epinastine;

(xxxviii) ophthalmologic anti-virals, e.g. adenine arabinoside and idoxuridine;

(xxxix) glaucoma treatments, e.g. timolol, metipranolol, carteolol, betaxolol, levobunolol, brimonidine, iopidine, dorzolamide, epinephrine and dipivefrin;

(xl) alkylating anti-tumor agents, e.g. busulfan, carboplatin, chlorambucil, cisplatin, cyclophosphamide, dacarbazine, ifosfamide, mechlorethamine, melphalan, procarbazine, thiotepa, and uracil mustard;

(xli) nitrosoureas, e.g. carmustine, lumustine and streptozocin;

(xlii) antimetabolites, e.g. 5-fluorouracil, 6-mercaptopurine, capecitabine, cytosine arabinoside, floxuridine, fludarabine, gemcitabine, methotrexate, thioguanine and azathioprine;

(xliii) antitumor biotics, e.g. dactinomycin, daunorubicin, doxorubicin, idarubicin, mitomycin-C, and mitoxantrone;

(xliv) anti-microtubule agents, e.g. vinblastine, vincristine, vindesine, vinorelbine, paclitaxel and docetaxel;

(xlv) vitamine derivatives, e.g., calcipotriol and tacalcitol;

(xlvi) leukotriene antagonists, e.g. montelukast, zafirlukast and pranlukast;

(xlvii) beta2 Agonists, e.g. albuterol, levalbuterol, salmeterol, formotero and arformoterol;

(xlviii) corticosteroids, e.g. prednisone, ciclesonide, budesonide, fluticasone, methyl-prednisolone, hydrocortisone and BP-1011;

(xlix) methylxanthines, e.g. theophylline, aminophylline and doxofylline;

(l) asthma and/or COPD treatments, e.g. roflumilast, tiotropium, israpafant, N-acetylcysteine and alphal-antitrypsin;

(li) a vanilloid receptor agonist (e.g. resinferatoxin) or antagonist (e.g. capsazepine);

(lii) an alpha-2-delta ligand such as gabapentin, pregabalin, 3-methylgabapentin, (1alpha,3alpha,5alpha)(3-aminomethyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid; and (liii) a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino-carbonyl]-4-methylbenzenesulfonamide or 4-[(1S)-1-({[5-chloro-2-(3-fluorophenoxy)pyridin-3-yl]carbonyl}amino)ethyl]benzoic acid.

Method for Assessing Biological Activities:

The CB2 receptor binding affinity, other biological activities and pharmacokinetic properties of the compounds of this invention are determined by the following procedures.

Rat CB2 Binding

Rat spleen cells were placed in tissue preparation buffer [50 mM Tris-HCl (pH7.4 at 25° C.) and 2 mM EDTA] and homogenized using a hand held Polytron PT1200 disruptor set at 25,000 rpm for 30 seconds on ice, then kept on ice for 15 min. The homogenates were centrifuged at 1,000×g at 4° C. for 10 min. The supernatant was recovered and centrifuged at 40,000×g at 4° C. for 10 min. The pellets were then resuspended in 50 mM Tris-HCl (pH7.4 at 25° C.). This suspension was centrifuged once more in the same manner. The final pellet was resuspended in TME buffer (25 mM Tris-HCl (pH7.4), 5 mM $MgCl_2$, 1 mM EDTA, 0.5% BSA), aliquoted and stored at −80° C. until assayed. An aliquot was used for the determination of protein concentration using BCA™ protein assay kit (PIERCE) and the measurement was made on Wallac 1420 ARVOsx multilabel counter with BSA as a standard.

For the binding experiments, 20 microL of test compounds were incubated with 20 microL of [$^3$H] CP55,940 (Perkin Elmer, final 1 nM) and 160 microL of membrane homogenate (1 microg protein/tube) for 60 minutes at 37° C. Nonspecific binding was determined by 1 microM CP55,940 (TOCRIS Cookson Inc) at the final concentration. All incubations were harvested by vacuum filtration through GF/B fiber filters pre-soaked in 5% BSA in TME buffer using Uni-Filter cell harvester (Packard). Filters were rinsed with wash buffer (25 mM Tris-HCl (pH7.4), 5 mM $MgCl_2$, 1 mM EDTA) and then dried up at 50° C. for 30 min. The radioactivity was measured by scintillation counting using Top-Count Microplate Scintillation Counter (Packard).

Rat CB1 binding affinities were also determined by a method similar to the above by using rat whole brains.

Human CB2 Binding

Human CB2 transfected Chinese hamster ovary K1 (CHO-K1) cells were established and grown to 60-80% confluence. The collected cell pastes were washed with cold PBS, suspended in 50 mM Tris-HCl (pH7.4 at 25° C.) containing protease inhibitor cocktail and homogenized using a hand held Polytron PT 1200 disruptor set at 25,000 rpm for 30 seconds on ice. The homogenates were centrifuged at 1,000×g at 4° C. for 10 min. The supernatant was recovered and centrifuged at 40,000×g at 4° C. for 10 min. The pellets were then resuspended in 50 mM Tris-HCl (pH7.4 at 25° C.). This suspension was centrifuged once more in the same manner. The final pellet was resuspended in TME buffer (25 mM Tris-HCl (pH7.4), 5 mM $MgCl_2$, 1 mM EDTA, 0.5% BSA), aliquoted and stored at −80° C. until assayed. An aliquot was used for the determination of protein concentration using BCA™ protein assay kit (PIERCE) and the measurement was made on Wallac 1420 ARVOsx multilabel counter with BSA as a standard.

For the binding experiments, 20 microL of test compounds were incubated with 20 microL of [$^3$H] CP55,940 (Perkin Elmer, final 1 nM) and 160 microL of membrane homogenate (1 microg protein/tube) for 60 minutes at 37° C. Nonspecific binding was determined by 1 microM CP55,940 (TOCRIS Cookson Inc) at the final concentration.

All incubations were harvested by vacuum filtration through GF/B fiber filters pre-soaked in 5% BSA in TME buffer using Uni-Filter cell harvester (Packard). Filters were rinsed with wash buffer (25 mM Tris-HCl (pH7.4), 5 mM $MgCl_2$, 1 mM EDTA) and then dried up at 50° C. for 30 min. The radioactivity was measured by scintillation counting using Top-Count Microplate Scintillation Counter (Packard).

Human CB1 binding affinities were also determined by a method similar to the above by using Human CB1 transfected Chinese hamster ovary-K1 (CHO-K1) cells, [$^3$H] SR141716A (Amersham Bioscience) and AM251 (TOCRIS Cookson Inc).

Agonist-induced cAMP change in human CB2 transfected CHO-K1 cells

Human CB2 transfected Chinese hamster ovary-K1 (CHO-K1) cells were established and grown in F-12 medium containing 10% dialysed FBS. On the day of the assay, the cells were harvested with PBS/1 mM EDTA, centrifuged and washed with PBS. Cell pellets were resuspended in the assay buffer (F-12 medium, 20 mM HEPES, 1 mM IBMX, 0.1% BSA) at the concentration of $1 \times 10^5$ cells/mL. The agonist samples were diluted from 10 mM stock solution in DMSO and dispensed into 384-well plate (5 microL/well) with dilute buffer, to which the prepared cell suspension was added (10 microL/well). After incubation for 30 minutes at room temperature, forskolin was added to the plate (5 microL/well, final 5 microM) and placed in 37° C. incubator for 30 minutes. Then, CAMP-XL665 conjugated was added and placed at room temperature for 30 minutes (10 microL/well), and then the anti-cAMP-cryptase conjugate was added to the lysate (10 microL/well). After further incubation for 60 minutes at room temperature, measurements were made on the PHERAstar (Excitation 337 nm, Emission 665 nm/620 nm). Data analysis was made based on the ratio of fluorescence intensity of each well at 620 nm and 665 nm. The equation "sigmoidal dose-response" was used for the determination of $EC_{50}$ and Emax values.

Agonist-induced cAMP change in human CB1 receptor was measured by using human CB1 transfected Chinese hamster ovary-K1 (CHO-K1) cells in the above similar method.

All compounds of Examples showed CB2 receptor agonistic activity ($EC_{50} < 0.03$ microM) with excellent selectivity against CB1 ($EC_{50} > 25$ microM).

Human Dofetilide Binding Assay

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac). Binding assays were conducted in a total volume of 30 microL in 384-well plates. The activity was measured by PHERAstar (BMG LABTECH) using fluorescence polarization technology. Ten microL of test compounds were incubated with 10 microL of fluorescence ligand (6 nM Cy3B tagged dofetilide derivative) and 10 microL of membrane homogenate (6 microg protein) for 120 minutes at room temperature. Nonspecific binding was determined by 10 microM E4031 at the final concentration.

All compounds of Examples showed high IC50 value (0.6 microM in example 5 and others are more than 30 microM) of human dofetilide binding.

Caco-2 Permeability

Caco-2 permeability was measured according to the method described in Shiyin Yee, Pharmaceutical Research, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the pre-incubation, the media was removed and test compound solution (10 microM) in buffer was added to the apical compartment. The inserts were moved to wells containing fresh basolateral buffer at 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$P_{app}$ (cm/sec)=(F*VD)/(SA*MD) where SA is surface area for transport (0.3 $cm^2$), VD is the donor volume (0.3 ml), MD is the total amount of drug on the donor side at t=0. All data represent the mean of 2 inserts. Monolayer integrity was determined by Lucifer Yellow transport.

Half-Life in Human Liver Microsomes (HLM)

Test compounds (1 microM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0.0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/ internal standard versus time. The slope of the line of best fit through the points yields the rate of metabolism (k). This was converted to a half-life value using following equations: Half-life=ln 2/k TNBS-Induced Chronic Colonic Allodynia in the Rat Male IGS (Sprague-Dawley) rats, 240-270 g (7 weeks, Charles River Japan) are used. Environment conditions are controlled at a 12-h light/dark cycle with lights on at 07:00 and an ambient temperature of 23+/−2° C. Rats are housed under this condition for 4 days before the surgery. Each group is used a group of 6-8 rats. Rats are fasted for 24 hours before use. After weighing and administration of the anesthetic (Ketamine/Xylazine), the animal is placed in the dorsal decubitus position. The abdomen is shaved and disinfected with 10% povidoneiodine solution (isodine). A 2-cm long median laparotomy is conducted by making the incision 3 cm from the sternum. The cecum is then found, grasped with the fingers, removed from the abdominal cavity and placed on a compress that has been previously moistened with isotonic saline. TNBS (Fluka; 50 mg/kg; 1.5 ml/kg in 30% EtOH) is injected into the proximal colon (1 cm from the cecum). Sham group's animal undergoes the same surgery but TNBS is not injected. After injection, the intestines are put back into the abdominal cavity. The muscle wall is then sutured with silk, using two cross-stitches. The skin is also sutured. After 7 days from the surgery, the balloon (5 cm in length) is inserted through the anus and kept in position (tip of balloon is 5 cm from the anus) by taping the catheter to the base of the tail. The animals are individually placed without restraint in cages for distention session. The balloon is progressively inflated by step of 5 mm Hg, from 0 to 70 mm Hg, each step of inflation lasting 30 s. Each cycle of colonic distention is controlled by a standard barostat (G&J Electronic Inc. CANADA). The pain threshold corresponds to the pressure that produced the first abdominal contraction. The abdominal contraction corresponds to waves of contraction of oblique musculature with inward turning of the hindlimb, or to humpbacked position, or to squashing of the lower abdomen against the floor (Wesselmann U et al., (1998) Neurosci Lett 246: 73-76). To determine the basal colonic threshold, two cycles of distention are performed on the same animal with an interval of >10 min before compound administration. The 1st distention is conducted to acclimate the rat to the colonic distention. The baseline is determined by the second distention. The effect of a test compound on the colonic threshold is investigated at X min post dosing. If necessary, the time course of effect of a test compound may be studied at different times.

Distribution of the Treatment Groups is as Follows:

TABLE 1

|  | Injection of TNBS | Treatment |
| --- | --- | --- |
| Sham control group | No | Vehicle |
| TNBS control group | Yes | Vehicle |
| Treated group | Yes | Test compound |

The data are expressed as median threshold (mm Hg) required to induce abdominal contractions in each group (vertical bars represent 1st and 3rd quartiles). Data are analyzed using Kruskal-Wallis test followed by Mann-Whitney U-test.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230-400 mesh ASTM) or Fuji Silysia Chromatorex (registered trademark) DU3050 (Amino Type, 30-50 micrometer) or Biotage silica (32-63 mm, KP-Sil) or Biotage amino bounded silica (35-75 mm, KP-NH). Microwave apparatus used in the reaction was Emrys optimizer (Personal chemistry) or Initiator™ Sixty (Biotage). The purification of compounds using HPLC was performed by the following apparatus and conditions ("process A"); Apparatus; Waters MS-trigger AutoPurification™ system Column; Waters XTerra C18, 19×50 mm, 5 micrometer particle, Method A; Methanol or acetonitrile/0.05% (v/v) formic acid aqueous solution, Method B; Methanol or acetonitrile/0.01% (v/v) ammonia aqueous solution. The purity check of the compounds obtained from "process A" was performed by the following apparatus and conditions Apparatus; Waters Acquity Ultra Parformance LC on TUV Detector and ZQ mass spectrometer, Column; Waters ACQUITY C18, 2.1×50 mm, 1.7 micrometer particle Detector; UV 210 nm, MS detect; ESI posi mode, Method name; QC_neutral_full_1pt5 min, Conditions; acetonitrile/10 mM sodium acetate aqueous solution, 5% (0 to 0.1 min.) gradient 5% to 95% (0.1 to 0.8 min) 95% (0.8 to 1 min); 1 ml/min, at 60° C., Analytical time; 1.5 min. The purification using HPLC ("Process B") was perfomed by the following apparatus and conditions: Apparatus; UV-trigger preparative HPLC system, Waters (Column; XTerra MS C18, 5 micrometer, 19×50 mm or 30×50 mm), Detector; UV 254 nm, Conditions; acetonitrile:0.05% formic acid aqueous solution or acetonitrile: 0.01% aqueous ammonia solution; 20 ml/min (19×50 mm) or 40 ml/min (30×50 mm) at room temperature. Low-resolution mass spectral data (EI) were obtained on a Integrity (Waters) mass spectrometer or a Automass 120 (JEOL) mass spectrometer or GC-MS Agilent Technologies, 6890GC/5793MSD. Low-resolution mass spectral data (ESI) were obtained by the following apparatus and conditions: Apparatus; Waters Alliance HPLC system on ZQ or ZMD mass spectrometer and UV detector, Column; Waters XTerra (registered trademark) C18, 2.1×30 mm, 3.5 micrometer particle, Gradient; 4-96% (0-2 min), 96% (2-4 min), Flow rate; 0.5 mL/min, UV detection: 254 nm, MS detection; ESI posi/nega mode, Eluent; acetonitrile: ca. 0.01% aqueous ammonium formate solution (Neutral full range), acetonitrile: 0.05% aqueous formic acid solution (Acidic full range), acetonitrile: 0.01% aqueous ammonia solution (Basic full range). NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. IR spectra were measured by a Shimazu infrared spectrometer (IR-470). Optical rotations were measured using a JASCO DIP-370 Digital Polarimeter (Japan Spectroscopic Co., Ltd.). Chemical symbols have their usual meanings; b.p. (boiling point), m.p. (melting point), L (liter(s)), mL (milliliter(s)), g (gram(s)), mg (milligram(s)), mol (moles), mmol (millimoles), eq. (equivalent(s)).

Example 1

3-(1-(2-(dimethylamino)ethyl)-2-neopentyl-1H-benzo[d]imidazol-5-ylsulfonyl)azetidine-1-carboxamide

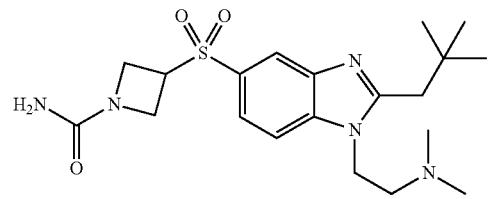

[Chem.8]

Step A 2-(5-bromo-2-neopentyl-1H-benzo[d]imidazol-1-yl)-N,N-dimethylethanamine

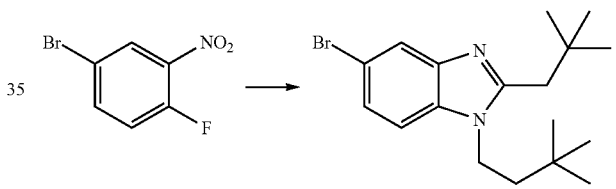

[Chem.9]

N,N-dimethylethylenediamine (2.08 g, 23.6 mmol) and triethylamine (2.56 mL, 18.2 mmol) were dissolved in ethanol (30 mL) at room temperature. Then to the solution was added 4-bromo-1-fluoro-2-nitrobenzene (4.00 g, 18.2 mmol). The mixture was stirred at 75° C. for 14 h. The mixture was concentrated in vacuo and the residue was diluted with ethyl acetate and saturated sodium bicarbonate aqueous solution to separate. The aqueous layer was extracted with ethyl acetate and the combined organic layers were dried over magnesium sulfate and concentrated in vacuo.

The residue was dissolved in tetrahydrofuran (50 mL). To the solution was added tri-fluoroacetic acid (1.54 mL, 20.0 mmol) and 5% PLATINUM ON CHARCOAL TYPE 128 PASTE (Johnson Matthey, 262 mg). The mixture was stirred under hydrogen at 3.5 to 4.5 atm for 3 h. The catalyst was filtered off through a celite pad and the filtrate was concentrated in vacuo.

The residue was dissolved in dichloromethane (40 mL). To the solution at 0° C. was added triethylamine (5.11 mL, 36.4 mmol), followed by tert-butylacetyl chloride (2.45 g, 18.2 mmol) in dichloromethane (10 mL). After stirring for 30 min at room temperature, the reaction was quenched with saturated sodium bicarbonate aqueous solution and the mixture was separated. The organic layer was dried over magnesium sulfate and concentrated in vacuo.

The obtained product was separated into two parts. Each part was dissolved in ethanol (18 mL) and added 8 mol/L sodium hydroxide solution (3.4 mL). The mixture was stirred at 130° C. for 1 h under microwave. After two reaction mixture were combined, the mixture was concentrated in vacuo. The residue was diluted with water and ethyl acetate to separate. The organic layer was washed with water and brine, dried over magnesium sulfate and concentrated in vacuo. The residue was purified by silica gel column chromatography (hexane-ethyl acetate, gradient) to give the title compound (4.19 g, 68%).

MS (ESI) m/z 338 [M($^{79}$Br)+H]$^+$, 340 [M($^{81}$Br)+H]$^+$.

$^1$H-NMR (300 MHz, CDCl$_3$) δ: 7.87(d, J=1.5 Hz, 1H), 7.34 (dd, J=8.4, 1.5 Hz, 1H), 7.19 (d, J=8.4 Hz, 1H), 4.24 (t, J=7.9 Hz, 2H), 2.79 (s, 2H), 2.58 (t, J=7.9 Hz, 2H), 2.31 (s, 6H), 1.09 (s, 9H).

Step B tert-butyl 3-iodoazetidine-1-carboxylate

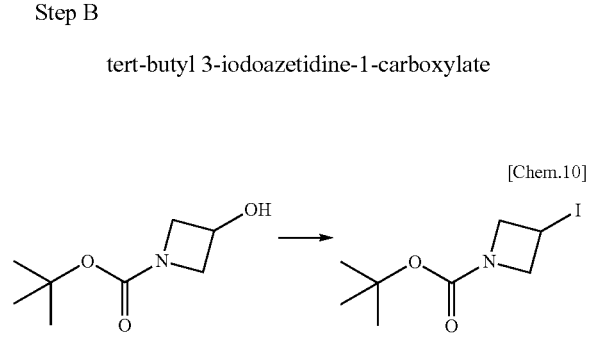

[Chem.10]

To a solution of tert-butyl 3-hydroxyazetidine-1-carboxylate (3.35 g, 19.3 mmol) in toluene (200 mL) was added imidazole (3.95 g, 58.0 mmol), triphenylphosphine (10.1 g, 38.7 mmol) and iodine (7.36 g, 29.0 mmol). The mixture was heated for 100° C. for 1 h, cooled to room temperature, then poured into sodium bicarbonate aqueous solution (30 mL). Excess triphenylphosphine was destroyed by addition of iodine until iodine coloration persisted in organic layer. The organic layer was separated and washed with saturated sodium thiosulfate aqueous solution, dried over sodium sulfate. The crude product was purified by silica gel column chromatography (hexane-ethyl acetate=9:1 to 1:1) to gave the title compound (5.42 g, 99%) as clear oil.

$^+$MS (ESI) m/z 284 (M+H)$^+$.

Step C tert-butyl 3-(acetylthio)azetidine-1-carboxylate

[Chem.11]

Mixture of tert-butyl 3-iodoazetidine-1-carboxylate (STEP B, 2.05 g, 7.24 mmol), cesium carbonate (4.72 g, 14.5 mmol), thioacetic acid (1.10 g, 14.5 mmol) and dimethyl formamide (10 mL) was stirred at 70° C. for 4 h. The reaction mixture was cooled to room temperature and diluted with diethyl ether (200 mL). The resulting mixture was washed with water (80 mL×3) and brine (50 mL), then dried over magnesium sulfate.

The crude product was purified with silica gel column chromatography (hexane-ethyl acetate=4:1) to give the title compound (1.64 g, 98%) as orange oil.

MS (ESI) m/z 232 (M+H)$^+$.

Step D tert-butyl 3-mercaptoazetidine-1-carboxylate

[Chem.12]

Mixture of tert-butyl 3-(acetylthio)azetidine-1-carboxylate (STEP C, 700 mg, 3.03 mmol), methanol (10 mL) and potassium carbonate (836 mg, 6.05 mol) was stirred at 50° C. for 2 h and cooled to room temperature. To the reaction mixture was added 2 mol/L hydrochloric acid for solution acidified (pH <4). The resulting solution was extracted with diethyl ether (30 mL×2). The organic layer was combined and washed with water (30 mL×2) and brine (30 mL). The extract was dried with magnesium sulfate and concentrated. Resulting crude product (581 mg) was used without further purification.

$^1$H-NMR (300 MHz, CDCl$_3$) δ: 4.34 (dd, J=8.8, 8.0 Hz, 2H), 3.79 (dd, J=8.8, 5.9 Hz, 2H), 3.71-3.59 (m, 1H), 2.00 (d, J=8.0 Hz, 1H), 1.44 (s, 9H).

Step E tert-butyl 3-(1-(2-(dimethylamino)ethyl)-2-neopentyl-1H-benzo[d]imidazol-5-ylthio)azetidine-1-carboxylate

[Chem.13]

-continued

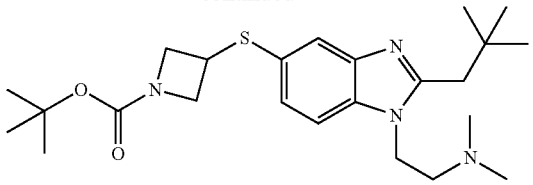

A mixture of 2-(5-bromo-2-neopentyl-1H-benzo[d]imidazol-1-yl)-N,N-dimethylethanamine (STEP A, 338 mg, 1.00 mmol), tert-butyl 3-mercaptoazetidine-1-carboxylate (STEP D, 246 mg, 1.30 mmol), Xantphos (28.9 mg, 0.0500 mmol), tris(dibenzylideneacetone)dipalladium (22.3 mg, 0.0250 mmol) and N,N-diisopropylethylamine (262 microL, 1.50 mmol) in 1,4-dioxane (4 mL) was stirred at 160° C. for 1 h under microwave. The mixture was concentrated in vacuo and the residue was purified by amine gel column chromatography (hexane-ethyl acetate, gradient) to give the title compound (442 mg, 99%) as a yellow oil.

MS (ESI) m/z 447 (M+H)+.

$^1$H-NMR (300 MHz, CDCl$_3$) δ: 7.72 (s, 1H), 7.28-7.23 (m, 2H), 4.30-4.21 (m, 4H), 4.02-3.85 (m, 3H), 2.80 (s, 2H), 2.59 (t, J=7.7 Hz, 2H), 2.32 (s, 6H), 1.40 (s, 9H),

Step F tert-butyl 3-(1-(2-(dimethylamino)ethyl)-2-neopentyl-1H-benzo[d]imidazol-5-ylsulfonyl)azetidine-1-carboxylate

[Chem.14]

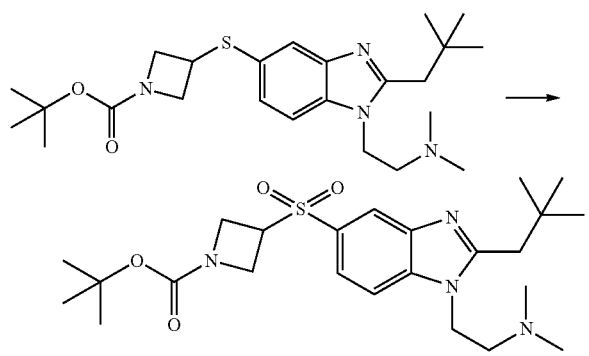

To a solution of tert-butyl 3-(1-(2-(dimethylatnino)ethyl)-2-neopentyl-1H-benzo[d]imidazol-5-ylthio)azetidine-1-carboxylate (STEP E, 442 mg, 0.990mmol) in dichloromethane (10 mL) at 0° C. was added trifluoroacetic acid (381 microL, 4.95 mmol) and 70% m-chloroperbenzoic acid (478 mg, 2.08 mmol). After stirring for 14 h, the reaction was quenched with dimethyl sulfoxide (0.2 mL). The mixture was diluted with ethyl acetate and washed with saturated sodium bicarbonate aqueous solution. The organic layer was dried over sodium sulfate and concentrated in vacuo. The residue was purified by amine gel column chromatography (hexane - ethyl acetate, gradient) to give the title compound (297 mg, 63%) as an amorphous.

MS (ESI) m/z 479 (M+H)+.

$^1$H-NMR (300 MHz, CDCl$_3$) δ: 8.29 (d, J=2.0 Hz, 1H), 7.79 (dd, J=8.6, 2.0 Hz, 1H), 7.48 (d, J=8.6 Hz, 1H), 4.35-4.25 (m, 4H), 4.09-3.98 (m, 3H), 2.85 (s, 2H), 2.61 (t, J=7.3 Hz, 2H), 2.32 (s, 6H), 1.41 (s, 9H), 1.12 (s, 9H).

Step G 3-(1-(2-(dimethylamino)ethyl)-2-neopentyl-1H-benzo[d]imidazol-5-ylsulfonyl)azetidine-1-carboxamide fumarate

[Chem.15]

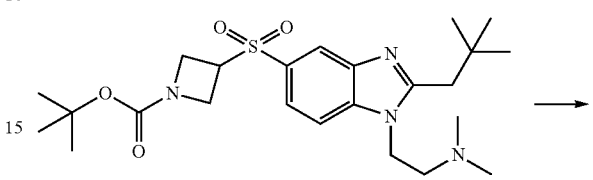

fumarate

To a solution of tert-butyl 3-(1-(2-(dimethylamino)ethyl)-2-neopentyl-1H-benzo[d]imidazol-5-ylsulfonyl)azetidine-1-carboxylate (STEP F, 297 mg, 0.620 mmol) in methanol (6 mL) was added chlorotrimethylsilane (634 microL, 4.96 mmol). After stirring for 1 h at 60° C., the mixture was concentrated in vacuo.

The residue was diluted with dichloromethane (6 mL) and to the mixture was added triethylamine (436 microL, 3.10 mmol) and trimethylsilyl isocyanate (252 microL, 1.86 mmol) at room temperature. After stirring for 20 min, the reaction was quenched with methanol (1 mL) and concentrated in vacuo. The residue was diluted with ethyl acetate and water. The mixture was washed with saturated sodium bicarbonate aqueous solution and brine, dried over sodium sulfate and concentrated in vacuo. The residue was purified by silica gel chromatography (dichloromethane-methanol, gradient) to give the title compound (202 mg, 77%) as an amorphous.

The obtained urea was dissolved in methanol (2 mL) and to the solution was added fumaric acid (61 mg, 0.527 mmol) and the mixture was concentrated in vacuo. Recrystallization from ethanol (8 mL) and methanol (1 mL) gave the title compound (1.5 fumarate, 165 mg).

MS (ESI) m/z 422 (M+H)+.

NMR (DMSO-d6); $^1$-H-NMR (300 MHz, CDCl$_3$) δ: 8.08 (d, J=1.5 Hz, 1H), 7.79 (d, J=8.8 Hz, 1H), 7.48 (dd, J=8.8, 1.5

Hz, 1H), 6.62 (s, 3H), 6.06 (brs, 2H), 4.45-4.36 (m, 3H), 4.01-3.90 (m, 4H), 2.84 (s, 2H), 2.60 (t, J=6.6 Hz, 2H), 2.22 (s, 6H), 1.08 (s, 9H).

Example 2

3-(1-(2-hydroxy-2-methylpropyl)-2-neopentyl-1H-benzo[d]imidazol-5-ylsulfonyl)azetidine-1-carboxamide

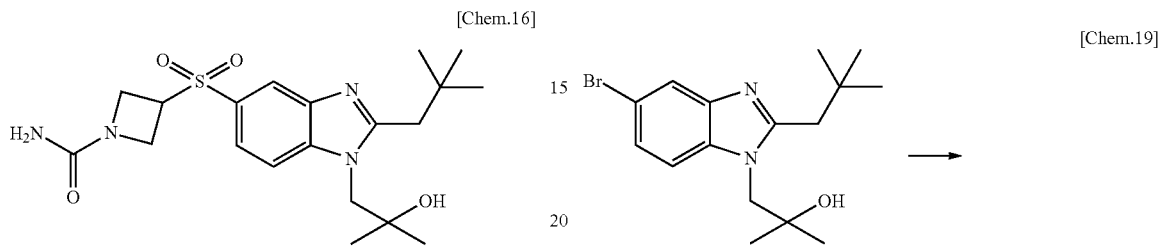

[Chem.16]

Step A 1-amino-2-methylpropan-2-ol

[Chem.17]

To a suspension of lithium aluminumhydride (6.08 g, 160 mmol) in tetrahydrofuran (180 mL) at 0° C. was added acetone cyanohydrin (7.32 mL, 80.0 mmol) in tetrahydrofuran (20 mL) over a period of 15 min. After refluxing for 4 h, the mixture was cooled to 0° C. The reaction was quenched with sodium sulfate decahydrate and potassium fluoride. After stirring at 35° C. for 30 min, the mixture was filtered through a celite pad. The filtrate was concentrated in vacuo to give the title compound (3.98 g, 56%) as an oil.

$^1$H-NMR (300 MHz, CDCl$_3$) δ: 2.60 (s, 2H), 1.69 (s, 6H), peaks of OH and NH$_2$ were not observed.

Step B 1-(5-bromo-2-neopentyl-1H-benzo[d]imidazol-1-yl)-2-methylpropan-2-ol

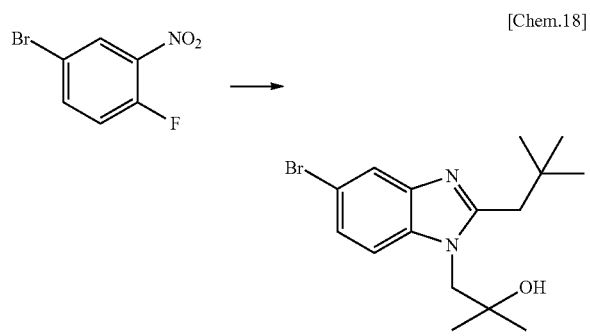

[Chem.18]

The title compound was prepared according to the procedure described in STEP A of Example 1 using 1-amino-2-methylpropan-2-ol (STEP A) instead of N,N-dimethylethylenediamine.

$^1$H-NMR (300 MHz, CDCl$_3$) δ: 7.85(s, 1H), 7.34-7.25 (m, 2H), 4.16 (s, 2H), 2.86 (s, 2H), 1.28 (s, 6H), 1.04 (s, 9H), a peak of OH was not observed.

Step C tert-butyl 3-(1-(2-hydroxy-2-methylpropyl)-2-neopentyl-1H-benzo[d]imidazol-5-ylsulfonyl)azetidine-1-carboxylate

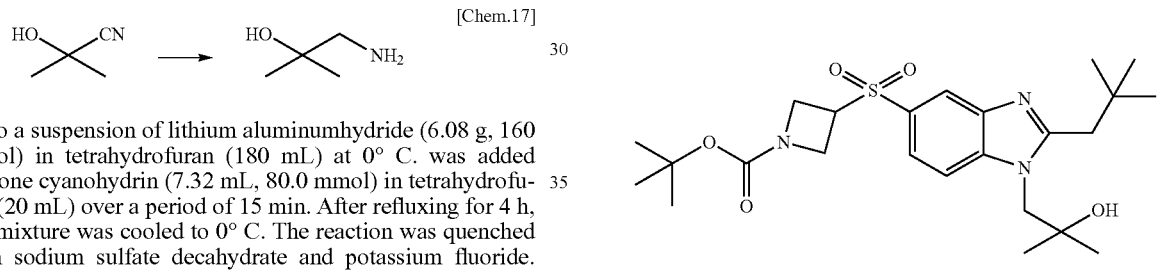

[Chem.19]

A mixture of 1-(5-bromo-2-neopentyl-1H-benzo[d]imidazol-1-yl)-2-methylpropan-2-ol (STEP B, 296 mg, 0.871 mmol), tert-butyl 3-mercaptoazetidine-1-carboxylate (STEP D of Example 1, 214 mg, 1.13 mmol), Xantphos (25.2 mg, 0.0436 mmol), tris(dibenzylideneacetone)dipalladium (19.9 mg, 0.0218 mmol) and N,N-diisopropylethylamine (228 microL, 1.31 mmol) in 1,4-dioxane (4 mL) was stirred at 160° C. for 1 h under microwave. The mixture was concentrated in vacuo.

MS (ESI) m/z 448 (M+H)$^+$.

To a solution of the obtained sulfide in methanol (9 mL) was added 30% hydrogen peroxide aqueous solution (267 microL, 8.71 mmol) and sodium tungstate dihydrate (14.4 mg, 0.0436 mmol) at room temperature. After stirring for 16 h, dimethyl sulfoxide (1 mL) was added to the mixture to quench the reaction. After 10 min, the mixture was concentrated. The residue was diluted with dichloromethane and washed with brine, dried over sodium sulfate and concentrated in vacuo. The crude product was purified by silica gel column chromatography (hexane-ethyl acetate, gradient) to give the title compound (408 mg, 98%) as an amorphous.

MS (ESI) m/z 480 (M+H)$^+$.

$^1$H-NMR (300 MHz, CDCl$_3$) δ: 8.28 (d, J=1.8 Hz, 1H), 7.74 (dd, J=8.4, 1.8 Hz, 1H), 7.60 (d, J=8.4 Hz, 1H), 4.36-4.25 (m, 2H), 4.23 (s, 2H), 4.08-4.00 (m, 3H), 2.93 (s,2H), 1.51 (s,1H), 1.42 (s, 9H), 1.30 (s, 6H), 1.08 (s, 9H).

Step D 3-(1-(2-hydroxy-2-methylpropyl)-2-neopentyl-1H-benzo[d]imidazol-5-ylsulfonyl)azetidine-1-carboxamide

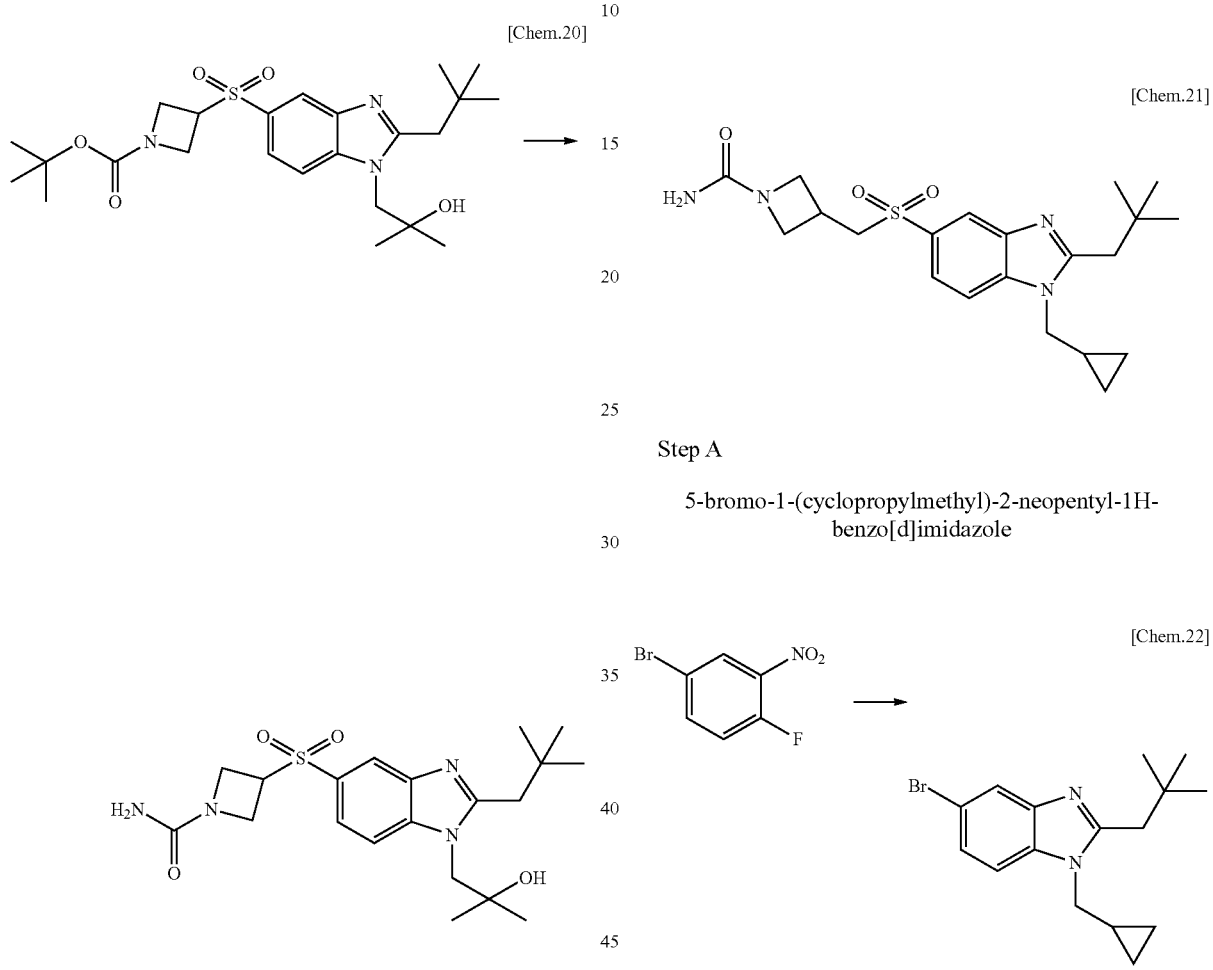

To a solution of tert-butyl 3-(1-(2-hydroxy-2-methylpropyl)-2-neopentyl-1H-benzo[d]imidazol-5-ylsulfonyl)azetidine-1-carboxylate (STEP C, 408 mg, 0.851 mmol) in methanol (9 mL) was added chlorotrimethylsilane (544 microL, 4.25 mmol). After stirring for 1 h at 60° C., the mixture was concentrated in vacuo. The residue was diluted with dichloromethane (9 mL) and to the mixture was added triethylamine (598 microL, 4.25 mmol) and trimethylsilyl isocyanate (345 microL, 2.55 mmol) at room temperature. After stirring for 20 min, the reaction was quenched with methanol (1 mL) and concentrated in vacuo. The residue was diluted with ethyl acetate and water. The mixture was washed with saturated sodium bicarbonate aqueous solution and brine, dried over sodium sulfate and concentrated to give a pale yellow solid (295 mg). The solid was added ethanol (1.5 mL) and ethyl acetate (1.5 mL) and the suspension was stirred at 65° C. for 15 min. The mixture was cooled to room temperature and the solid was filtered to give the title compound (177 mg, 49%) as a white solid.

MS (ESI) m/z 423 (M+H)$^+$.

$^1$H-NMR (300 MHz, CDCl$_3$) δ: 8.30 (s, 1H), 7.75 (d, J=8.1 Hz, 1H), 7.62 (d, J=8.1 Hz, 1H), 4.40-4.01 (m, 7H), 4.23 (s, 2H), 3.74 (brs, 1H), 2.93 (s, 2H), 1.30 (s, 6H), 1.08 (s, 9H).

Example 3

3-((1-(cyclopropylmethyl)-2-neopentyl-1H-benzo[d]imidazol-5-ylsulfonyl)methyl)azetidine-1-carboxamide

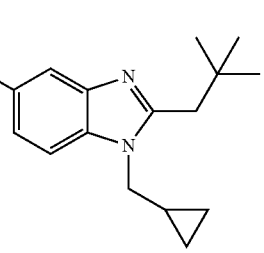

Step A 5-bromo-1-(cyclopropylmethyl)-2-neopentyl-1H-benzo[d]imidazole

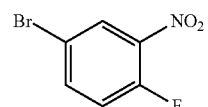

Cyclopropylamine (1.81 g, 25.5 mmol) and triethylamine (5.11 mL, 36.4 mmol) were dissolved in ethanol (25 mL). Then to the solution was added 4-bromo-1-fluoro-2-nitrobenzene (4.00 g, 18.2 mmol) in ethanol (5 mL) at room temperature. After refluxing for 2 h, the mixture was concentrated in vacuo.

The residue was diluted with ethyl acetate and the solution was washed with saturated ammonium chloride aqueous solution, dried over magnesium sulfate and concentrated in vacuo.

The residue was dissolved in tetrahydrofuran (50 mL). To the solution was added 5% PLATINUM ON CHARCOAL TYPE 128 PASTE (Johnson Matthey, 247 mg) and the mixture was stirred under hydrogen at 3.5 to 4.5 atm for 4 h. The mixture was filtered through celite and the filtrate was concentrated in vacuo.

The residue was dissolved in dichloromethane (40 mL). To the solution at 0° C. was added triethylamine (5.11 mL, 36.4 mmol), followed by tert-butylacetyl chloride (2.45 g, 18.2 mmol) in dichloromethane (10 mL). After stirring for 30 min at room temperature, the reaction was quenched with saturated sodium bicarbonate aqueous solution to separate. The aqueous layer was extracted with dichloromethane and the combined organic layers were washed with brine, dried over sodium sulfate and concentrated in vacuo.

The obtained product was separated into three parts. Each part was dissolved in ethanol (18 mL) and added 8 mol/L sodium hydroxide solution (2.3 mL). The mixture was stirred at 130° C. for 1 h under microwave. After three reaction mixture were combined and the whole was concentrated in vacuo. The residue was diluted with water and dichloromethane to separate. The organic layer was washed with brine, dried over magnesium sulfate and concentrated in vacuo. The crude was purified by silica gel column chromatography (hexane-ethyl acetate, gradient) to give the title compound (3.95 g, 68%) as a solid.

MS (ESI) m/z 321 [M($^{79}$Br)]$^+$, 323 [M($^{81}$Br)]$^+$.

$^1$H-NMR (300 MHz, CDCl$_3$) δ: 7.87 (d, J=1.6 Hz, 1H), 7.33 (dd, J=8.2, 1.6 Hz, 1H), 7.22 (d, J=8.2 Hz, 1H), 4.05 (d, J=6.6 Hz, 2H), 2.80 (s, 2H), 1.22-1.04 (m, 1H), 1.07 (s, 9H), 0.65-0.56 (m, 2H), 0.40-0.32 (m, 2H).

Step B tert-butyl 3-(hydroxymethyl)azetidine-1-carboxylate

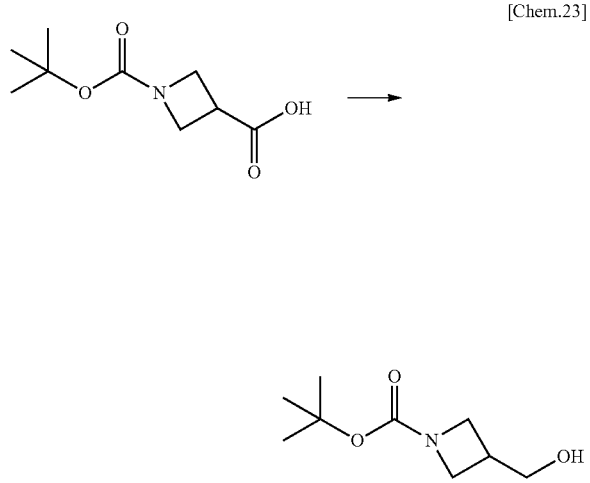

[Chem.23]

To a solution of 1-(tert-butoxycarbonyl)azetidine-3-carboxylic acid (3.00 g, 14.9 mmol) in tetrahydrofuran (15 mL) was added N-methylmorpholine (1.80 mL, 16.4 mmol) and isobutyl chloroformate (2.13 mL, 16.4 mmol) at 0° C. The mixture was stirred for 20 min. The resulting precipitate was filtered off and the filter cake was washed with tetrahydrofuran (1 mL). The filtrate was cooled to 0° C. and a solution of sodium borohydride (0.846 g, 22.4 mmol) in water (2 mL) was added. The resulting mixture was stirred for 1 h. and quenched with sodium bicarbonate aqueous solution. The mixture was extracted with ethyl acetate (55 mL). The organic layer was washed with brine (30 mL) and dried over sodium sulfate. The resulting solution was concentrated in vacuo. The crude product (2.79 g) was used for the next step without purification.

MS (ESI) m/z 188 (M+H)$^+$.

Step C tert-butyl 3-(acetylthiomethyl)azetidine-1-carboxylate

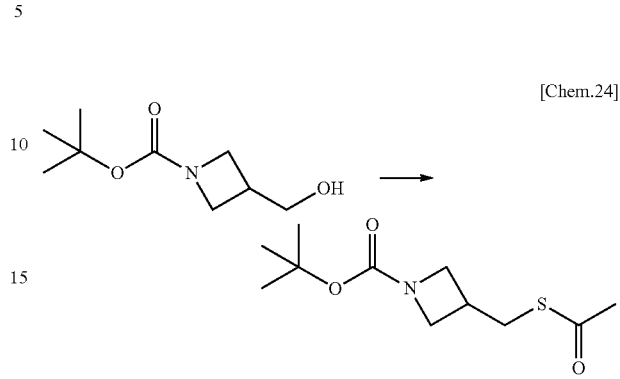

[Chem.24]

To a solution of tert-butyl 3-(hydroxymethyl)azetidine-1-carboxylate (2.79 g, 14.9 mmol) and triethylamine (3.14 mL, 22.4 mmol) in dichloromethane (10 mL) was added methanesulfonyl chloride in dichloromethane (1 mL) at 0° C. After stirring for 30 min at room temperature, the reaction was quenched with sodium bicarbonate aqueous solution. The mixture was concentrated under reduced pressure and the residue was diluted with ethyl acetate and washed with sodium bicarbonate aqueous solution and saturated ammonium chloride aqueous solution. The resulting solution was dried over magnesium sulfate and concentrated to give the crude product (3.24 g) as yellow oil.

MS (ESI) m/z 266(M+H)$^+$.

A mixture of the obtained product (3.24 g), thioacetic acid (3.32 g, 30.5 mmol), potassium carbonate (2.19 g, 15.9 mmol) and dimethyl formamide (10 mL) was stirred at room temperature for 5 h. The reaction mixture was diluted with ethyl acetate (50 mL). The resulting mixture was washed with water (30 mL) and brine (25 mL), and then dried over sodium sulfate. The crude product was purified with silica gel column chromatography (hexane-ethyl acetate, gradient) to give the title compound (2.16 g, 72%).

MS (ESI) m/z 246(M+H)$^+$.

Step D tert-butyl 3-(mercantomethyl)azetidine-1-carboxylate

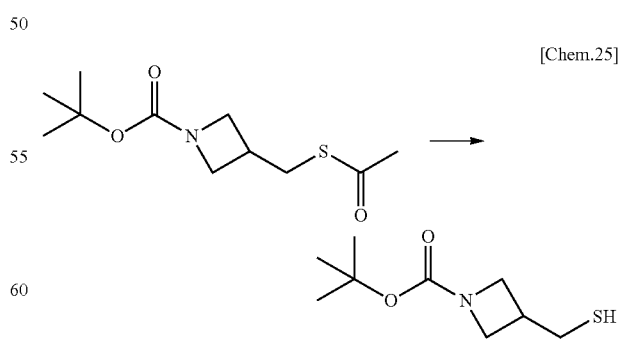

[Chem.25]

A mixture of tert-butyl 3-(sulfanylmethyl)azetidine-1-carboxylate (1.01 g3.13 mmol), 5-bromo-2-tert-butyl-1-(cyclopropylmethyl)-1H-1,3-benzodiazole (0.789 g, 3.88 mmol), N,N-diisopropylethylamine (0.820 mL, 4.69 mmol), Xantphos (91.0 mg, 0.156 mmol) and tris(dibenzylideneacetone) dipalladium (72.0 mg, 0.078 mmol) and 1,4-dioxane (10 mL) was stirred at 135° C. for 17 h. After cooling, the mixture was diluted with ethyl acetate (50 mL) and washed with saturated ammonium chloride aqueous solution. The organic phase was dried over magnesium sulfate. The resulting solution was concentrated in vacuo. The residue was used for next step without purification.

MS (ESI) m/z 204(M+H)$^+$, 202(M−H)$^-$.

Step E tert-butyl 3-((1-(cyclopropylmethyl)-2-neopentyl-1H-benzo[d]imidazol-5-ylsulfonyl)methyl)azetidine-1-carboxylate

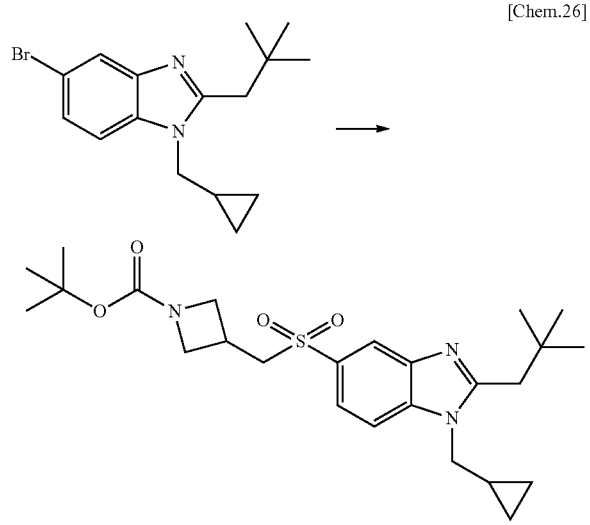

[Chem.26]

A mixture of tert-butyl 3-(sulfanylmethyl)azetidine-1-carboxylate (1.01 g, 3.13 mmol), 5-bromo-2-tert-butyl-1-(cyclopropylmethyl)-1H-1,3-benzodiazole (0.789 g, 3.88 mmol), N,N-diisopropylethylamine (0.820 mL, 4.69 mmol), Xantphos (91.0 mg, 0.156 mmol) and tris(dibenzylideneacetone) dipalladium (72.0 mg, 0.078 mmol) and 1,4-dioxane (10 mL) was stirred at 135° C. for 17 h. After cooling, the mixture was diluted with ethyl acetate (50 mL) and washed with saturated ammonium chloride aqueous solution. The organic phase was dried over magnesium sulfate. The resulting solution was concentrated in vacuo. The residue was used for next step without purification.

MS (ESI) m/z 444(M+H)$^+$.

To a solution of the obtained sulfide in methanol (10 mL) was added 30% hydrogen peroxide aqueous solution (3.20 mL, 31.3 mmol) and a solution of sodium tungstate dihydrate (52.0 mg, 0.157 mmol) in water (0.5 mL) at room temperature. The resulting mixture was stirred for 6 h. Dimethyl sulfoxide (1 mL) was added to the mixture to quench the reaction. After 15 min, the mixture was concentrated and the residue was diluted with ethyl acetate (30 mL) and washed with water and brine. The organic layer was dried over magnesium sulfate and concentrated under reduced pressure. The crude product was purified by silica gel column chromatography (hexane-ethyl acetate=9:1 to ethyl acetate only) to give the title compound (1.48 g, 99%) as an amorphous.

MS (ESI) m/z 476 (M+H)$^+$.

Step F 5-(azetidin-3-ylmethylsulfonyl)-1-(cyclopropylmethyl)-2-neopentyl-1H-benzo[d]imidazole

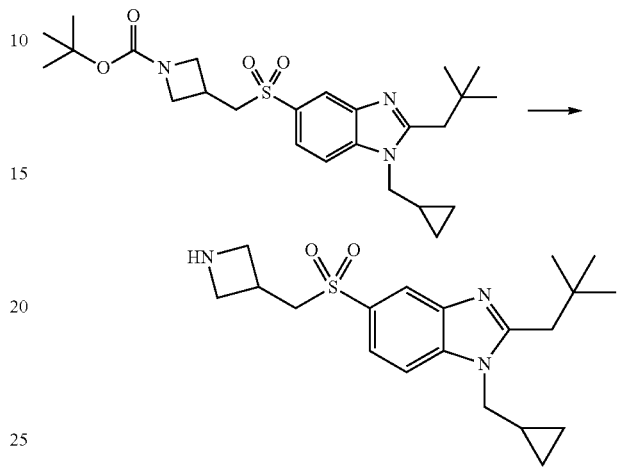

[Chem.27]

To a solution of tert-butyl 3-((1-(cyclopropylmethyl)-2-neopentyl-1H-benzo[d]imidazol-5-ylsulfonyl)methyl)azetidine-1-carboxylate (STEP E, 1.48 g, 3.11 mmol) in methanol (10 mL) was added chlorotrimethylsilane (1.35 g, 12.4 mmol). The resulting mixture was refluxed for 1 h. The reaction mixture was concentrated to give the title compound (1.26 g) as an amorphous.

MS (ESI) m/z 376 (M+H)$^+$.

Step G 3-((1-(cyclopropylmethyl)-2-neopentyl-1H-benzo[d]imidazol-5-ylsulfonyl)methyl)azetidine-1-carboxamide

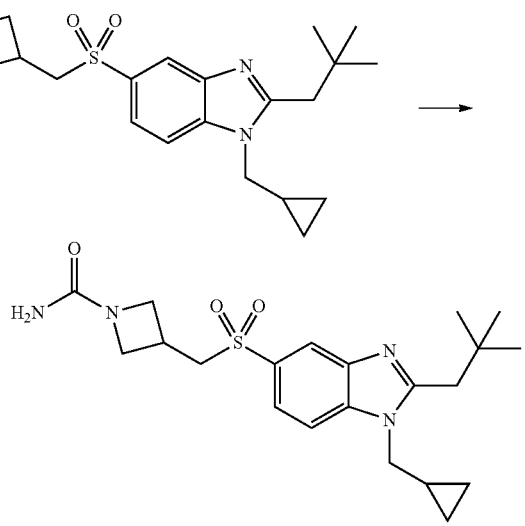

[Chem.28]

To the solution of 5-(azetidin-3-ylmethylsulfonyl)-1-(cyclopropylmethyl)-2-neopentyl-1H-benzo[d]imidazole (STEP F, 350 mg, 0.780 mmol) and triethylamine (395 microL, 2.81 mmol) in dichloromethane (5 mL) was added trimethylsilyl isocyanate (162 microL, 1.02 mmol) at room temperature. The resulting solution was stirred for 1 h. The reaction mixture was concentrated in vacuo. The residue was extracted with ethyl acetate (15 mL) and washed with water (30 mL). The organic layer was dried over magnesium sulfate. The crude product was purified with silica gel column chromatography (ethyl acetate-methanol=100:1 to 100:8) to give the title compound (198 mg, 61%).

MS (ESI) m/z 419 (M+H)$^+$, 417(M−H)$^-$.

This product was recrystallized with ethyl acetate (3 mL), ethanol (0.5 mL) and hexane (1 mL) to give the title compound as white solid (129 mg).

$^1$H-NMR (300 MHz, CDCl$_3$) δ: 8.28(d, J=1.5 Hz, 1H), 7.75 (dd, J=8.0, 1.5 Hz, 1H), 7.51(d, J=8.0Hz, 1H), 4.21 (s, 2H), 4.13 (d, J=6.6 Hz, 2H), 4.10 (dd, J=8.1, 8.0 Hz, 2H), 3.73 (dd, J=8.1, 5.9 Hz, 2H), 3.44 (d, J=8.1 Hz, 2H), 3.13-3.00 (m, 1H), 2.86 (s, 2H), 1.32-1.10 (m, 1H), 1.11 (s, 9H), 0.69-0.62 (m, 2H), 0.43-0.37 (m, 2H).

Example 4

1-(cyclopropylmethyl)-5-((1-(methylsulfonyl)azetidin-3-yl)methylsulfonyl)-2-neopentyl-1H-benzo[d]imidazole

[Chem.29]

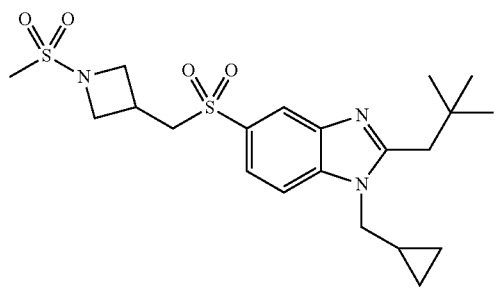

Step A 1-(cyclopropylmethyl)-5-((1-(methylsulfonyl)azetidin-3-yl)methylsulfonyl)-2-neopentyl-1H-benzo[d]imidazole

[Chem.30]

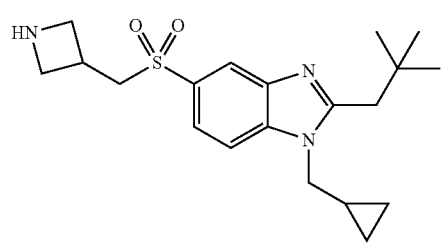

-continued

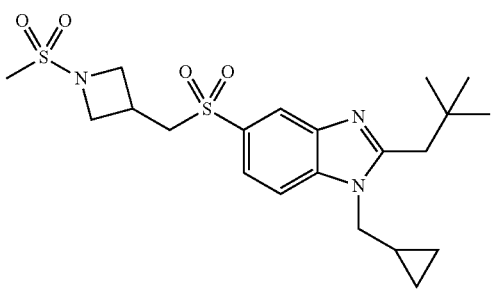

To a solution of 5-(azetidin-3-ylmethylsulfonyl)-1-(cyclopropylmethyl)-2-neopentyl-1H-benzo[d]imidazole (STEP F of Example 3, 350 mg, 0.780 mmol) and triethylamine (395 microL, 2.81 mmol) in dichloromethane (10 mL) was added methanesulfonyl chloride (67.0 microL, 0.819 mmol) and stirred for 3 h at room temperature. The reaction mixture was concentrated in vacuo, extracted with ethyl acetate (15 mL) and water (30 mL). The organic layer was dried over magnesium sulfate and concentrated in vacuo. The crude product was purified by silica gel column chromatography (dichloromethane-methanol=100:0 to 100:6). The resulting product was recrystallized with ethanol (6 mL)-ethyl acetate (1 mL) to give the title compound (212 mg) as pale yellow solid.

$^1$H-NMR (300 MHz, CDCl$_3$) δ: 8.27(d, J=1.5 Hz, 1H), 7.74 (dd, J=8.8, 1.5 Hz, 1H), 7.51(d, J=8.8 Hz, 1H), 4.13 (d, J=6.6 Hz, 2H), 3.99 (dd, J=8.8, 8.0 Hz, 2H), 3.72 (dd, J=8.0, 6.6 Hz, 2H), 3.43 (d, J=7.3 Hz, 2H), 3.14-3.00 (m, 1H), 2.86 (s, 2H), 2.83 (s, 3H), 1.32-1.10 (m, 1H), 1.11 (s, 9H), 0.69-0.62 (m, 2H), 0.43-0.37(m, 2H).

Example 5

1-(cyclopropylmethyl)-2-neopentyl-5-((1-(pyridin-4-yl)piperidin-4-yl)methylsulfonyl)-1H-benzo[d]imidazole

[Chem.31]

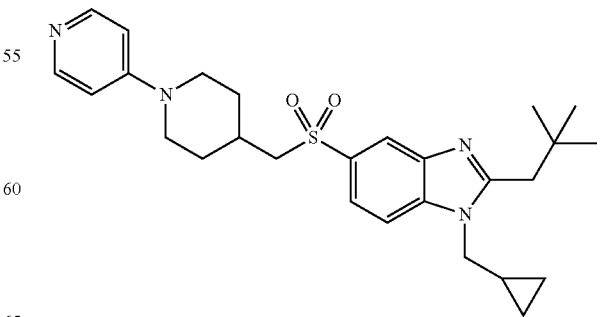

Step A tert-butyl 4-(acetylthiomethyl)piperidine-1-carboxylate

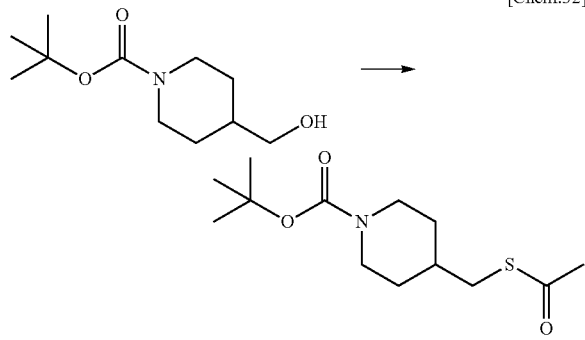

[Chem. 32]

The title compound was prepared according to the procedure described in STEP C of Example 3 using tert-butyl 4-(hydroxymethyl)piperidine-1-carboxylate instead of tert-butyl 3-(hydroxymethyl)azetidine-1-carboxylate.

$^1$H-NMR (300 MHz, CDCl$_3$) δ: 4.15-4.03 (m, 2H), 2.82 (d, J=6.6 Hz, 2H), 2.70-2.59 (m, 2H), 2.34 (s, 3H), 1.79-1.53 (m, 3H), 1.45-1.06 (m, 2H).

Step B tert-butyl 4-(mercaptomethyl)piperidine-1-carboxylate

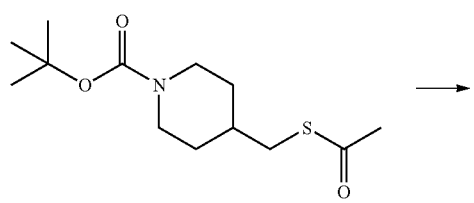

[Chem. 33]

The title compound was prepared according to the procedure described in Step D of Example 3 using tert-butyl 4-(acetylthiomethyl)piperidine-1-carboxylate (STEP A) instead of tert-butyl 3-(acetylthiomethyl)azetidine-1-carboxylate.

$^1$H-NMR (300 MHz, CDCl$_3$) δ: 4.21-4.03 (m, 2H), 2.77-2.60 (m, 2H), 2.46 (dd, J=8.8, 6.4 Hz, 2H), 1.87-1.52 (m, 3H), 1.25-1.03 (m, 2H).

Step C tert-butyl 4-((1-(cyclopropylmethyl)-2-neopentyl-1H-benzo[d]imidazol-5-ylsulfonyl)methyl)piperidine-1-carboxylate

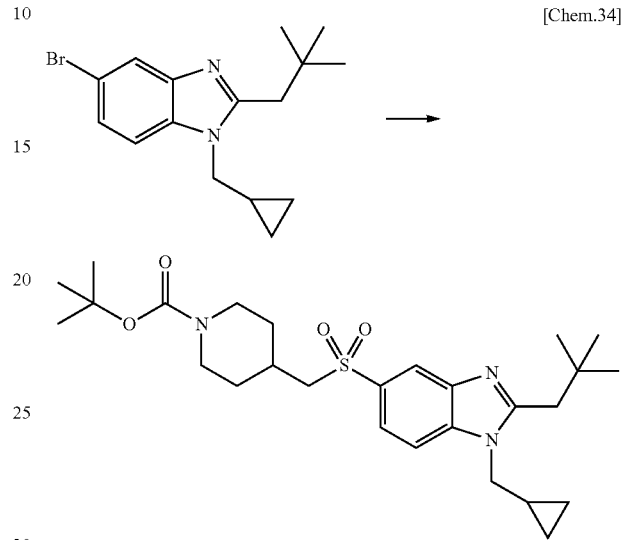

[Chem. 34]

The title compound was prepared according to the procedure described in STEP C of Example 2 using 5-bromo-1-(cyclopropylmethyl)-2-neopentyl-1H-benzo[d]imidazole (STEP A of Example 3) and tert-butyl 4-(mercaptomethyl)piperidine-1-carboxylate (STEP B) instead of tert-butyl 3-mercaptoazetidine-1-carboxylate.

MS (ESI) m/z 504 (M+H)$^+$.

$^1$H-NMR (300 MHz, CDCl$_3$) δ: 8.31 (s, 1H), 7.78 (d, J=8.4 Hz, 1H), 7.49 (d, J=8.4 Hz, 1H), 4.16-3.99 (m, 2H), 4.13 (d, J=6.6 Hz, 2H), 3.06 (d, J=6.6 Hz, 2H), 2.86 (s, 2H), 2.78-2.66 (m, 2H), 2.25-2.10 (m, 1H), 1.97-1.80 (m, 2H), 1.44 (s, 9H), 1.28-1.17 (m, 3H), 1.11 (s, 9H), 0.67-0.61 (m, 2H), 0.42-0.37 (m, 2H).

Step D 1-(cyclopropylmethyl)-2-neopentyl-5-(piperidin-4-ylmethylsulfonyl)-1H-benzo[d]imidazole

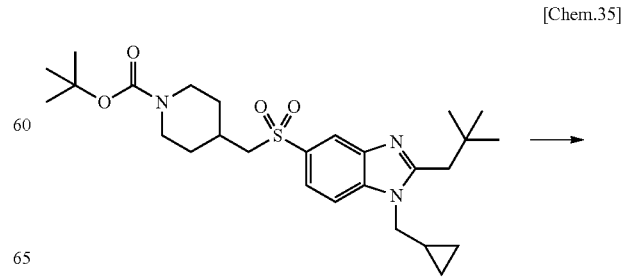

[Chem. 35]

-continued

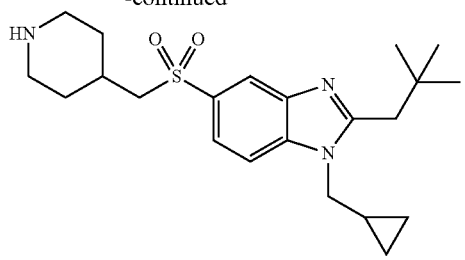

To a solution of tert-butyl 4-((1-(cyclopropylmethyl)-2-neopentyl-1H-benzo[d]imidazol-5-ylsulfonyl)methyl)piperidine-1-carboxylate (STEP C, 1.39 g, 2.76 mmol) in methanol (15 mL) was added chlorotrimethylsilane (1.41 mL, 11.0 mmol). After stirring for 18 h, the mixture was concentrated in vacuo. The residue was diluted ethyl acetate and basified with saturated sodium bicarbonate aqueous solution. The aqueous layer was extracted with ethyl acetate and the combined organic layers were dried over sodium sulfate and concentrated to give the title compound (809 mg, 73%) as an amorphous.
MS (ESI) m/z 404 (M+H)$^+$.
Step E 1-(cyclopropylmethyl)-2-neopentyl-5-((1-(pyridin-4-yl)piperidin-4-yl)methylsulfonyl)-1H-benzo[d]imidazole

[Chem.36]

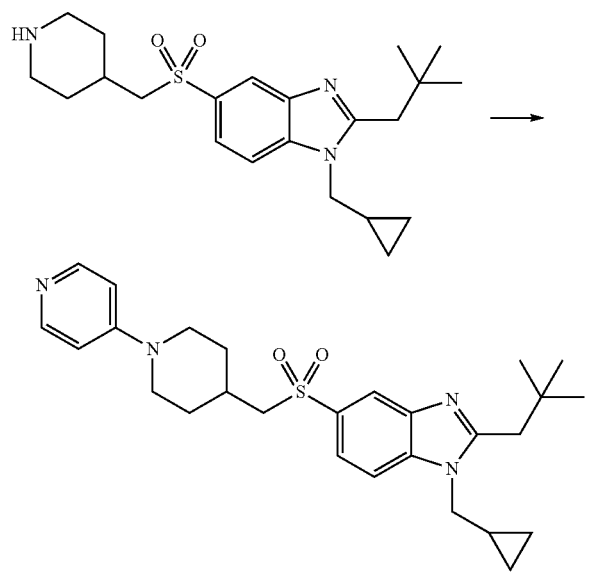

A mixture of 1-(cyclopropylmethyl)-2-neopentyl-5-(piperidin-4-ylmethylsulfonyl)-1H-benzo[d]imidazole (STEP D, 25 mg, 0.062 mmol), 4-chloropyridine hydrochloride (19 mg, 0.12 mmol) and triethylamine (35 microL, 0.25 mmol) in ethanol was stirred at 150° C. under microwave for 3 h. The solvent was removed. The residue was diluted with ethyl acetate and saturated sodium bicarbonate aqueous solution to separate. The aqueous layer was extracted with ethyl acetate (3 mL×2) and the organic layer was filtered through magnesium sulfate column. The filtrate was concentrated in vacuo. The residue was purified by prep-LC-MS ("process A").
MS (ESI) m/z 481 (M+H)$^+$.

Example 6

2-tert-butyl-1-(cyclopropylmethyl)-5-((1-(methylsulfonyl)piperidin-4-yl)methylsulfonyl)-1H-benzo[d]imidazole

[Chem.37]

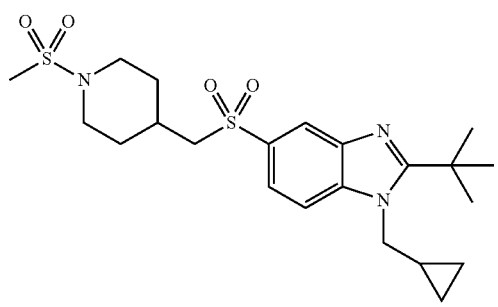

Step A 5-bromo-2-tert-butyl-1-(cyclopropylmethyl)-1H-benzo[d]imidazole

[Chem.38]

Cyclopropylmethylamine (1.81 g, 25.5 mmol) and triethylamine (5.11 mL, 36.4 mmol) were dissolved in ethanol (25 mL). Then to the solution was added 4-bromo-1-fluoro-2-nitrobenzene (4.00 g, 18.2 mmol) in ethanol (5 mL) at room temperature. After refluxing for 15 h, the mixture was concentrated in vacuo. The residue was diluted with ethyl acetate and the solution was washed with saturated ammonium chloride aqueous solution, dried over magnesium sulfate and concentrated.

The residue was dissolved in tetrahydrofuran (50 mL). To the solution was added 5% PLATINUM ON CHARCOAL TYPE 128 PASTE (Johnson Matthey, 247 mg) and the mixture was stirred under hydrogen at 3.5 to 4.5 atm for 4 h. The mixture was filtered through celite and the filtrate was concentrated in vacuo.

The residue was dissolved in dichloromethane (40 mL). To the solution at 0° C. was added triethylamine (5.11 mL, 36.4 mmol), followed by pivaloyl chloride (2.24 mL, 18.2 mmol) in dichloromethane (10 mL). After stirring for 30 min at room temperature, the reaction was quenched with saturated sodium bicarbonate aqueous solution to separate. The aqueous layer was extracted with dichloromethane and the combined organic layers were washed with brine, dried over sodium sulfate and concentrated in vacuo.

The residue was dissolved in acetonitrile (50 mL) and added 12 mol/L hydrochloric acid (10 mL). The mixture was stirred at 95° C. for 22 h. The mixture was basified by 6 mol/L sodium hydroxide solution and removed acetonitrile in vacuo. The residue was extracted with dichloromethane and the organic layer was dried over magnesium sulfate and concentrated in vacuo. The residue was purified by silica gel column chromatography (hexane-ethyl acetate, gradient) to give the title compound (4.50 g, 81%) as a violet oil.

$^1$H-NMR (300 MHz, CDCl$_3$) δ: 7.88 (d, J=2.0 Hz, 1H), 7.32 (dd, J=8.6, 2.0 Hz, 1H), 7.23 (d, J=8.6 Hz, 1H), 4.23 (d, J=5.9 Hz, 2H), 1.57 (s, 9H), 1.21-1.10 (m, 1H), 0.72-0.62 (m, 2H), 0.51-0.44 (m, 2H).

Step B tert-butyl 4-((2-tert-butyl-1-(cyclopropylmethyl)-1H-benzo[d]imidazol-5-ylsulfonyl)methyl)piperidine-1-carboxylate

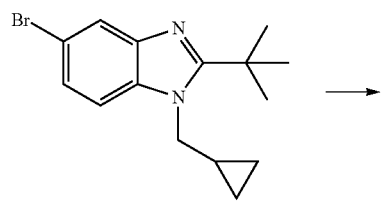

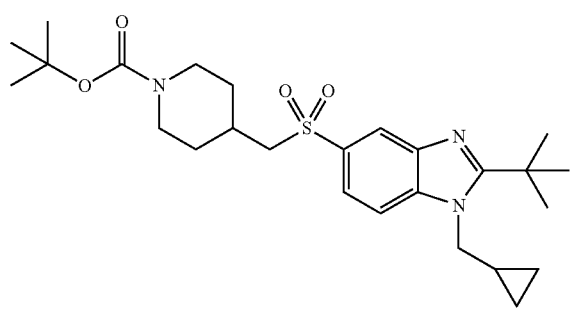

The title compound was prepared according to the procedure described in Step C of Example 2 using 5-bromo-2-tert-butyl-1-(cyclopropylmethyl)-1H-benzo[d]imidazole (STEP A) and tert-butyl 4-(mercaptomethyl)piperidine-1-carboxylate (STEP B of Example 5) instead of tert-butyl 3-mercaptoazetidine-1-carboxylate.

MS (ESI) m/z 490 (M+H)$^+$.

$^1$H-NMR (300 MHz, CDCl$_3$) δ: 8.32 (s, 1H), 7.77 (d, J=7.3 Hz, 1H), 7.50 (d, J=7.3 Hz, 1H), 4.31 (d, J=6.6 Hz, 2H), 4.09-3.96 (m, 2H), 3.04 (d, J=6.6 Hz, 2H), 2.82-2.61 (m, 2H), 2.20-2.07 (m, 1H), 1.97-1.76 (m, 2H), 1.60 (s, 9H), 1.44 (s, 9H), 1.28-1.18 (m, 3H), 0.76-0.67 (m, 2H), 0.56-0.47 (m, 2H).

Step C 2-tert-butyl-1-(cyclopropylmethyl)-5-(piperidin-4-ylmethylsulfonyl)-1H-benzo[d]imidazole dihydrocholide

[Chem.40]

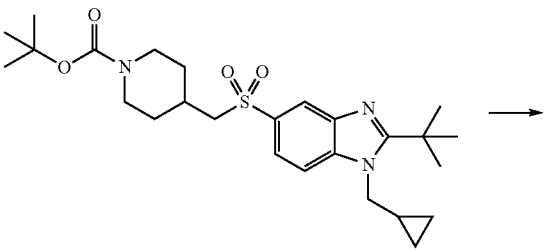

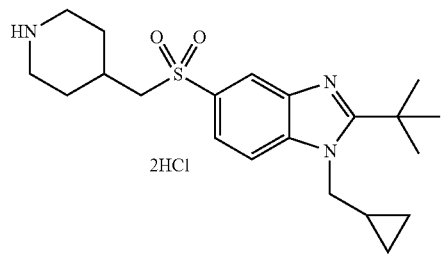

The title compound was prepared according to the procedure described in STEP F of Example 3 using tert-butyl 4-((2-tert-butyl-1-(cyclopropylmethyl)-1H-benzo[d]imidazol-5-ylsulfonyl)methyl)piperidine-1-carboxylate (STEP B) instead of tert-butyl 3-((1-(cyclopropylmethyl)-2-neopentyl-1H-benzo[d]imidazol-5-ylsulfonyl)methyl)azetidine-1-carboxylate.

MS (ESI) m/z 390 (M+H)$^+$.

Step D 2-tert-butyl-1-(cyclopropylmethyl)-5-((1-(methylsulfonyl)piperidin-4-yl)methylsulfonyl)-1)-1H-benzo[d]imidazole

[Chem.41]

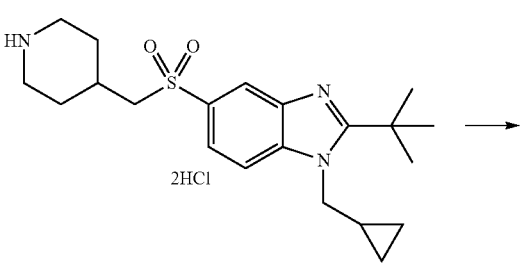

-continued

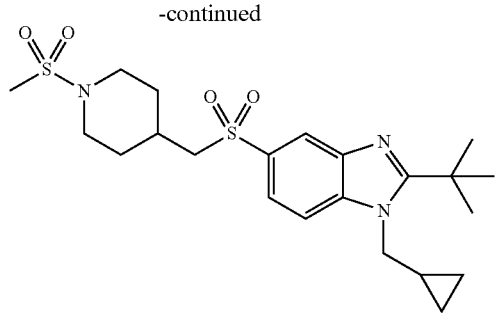

To a solution of 2-tert-butyl-1-(cyclopropylmethyl)-5-(piperidin-4-ylmethylsulfonyl)-1H-benzo[d]imidazole dihydrocholide (STEP C, 30 mg, 0.065 mmol) in dichloromethane (2 mL) was added triethylamine (55 microL, 0.39 mmol) and methanesulfonyl chloride (15 microL, 0.20 mmol) at room temperature. After 1 h, the mixture was concentrated and the residue was diluted with ethyl acetate (4 mL) and saturated sodium bicarbonate aqueous solution (3 mL) to separate. The organic layer was filtered through magnesium sulfate column and the filtrate was concentrated. The residue was purified by prep-LC-MS ("process A").

MS (ESI) m/z 468 (M+H)$^+$.

Example 7

5-(1-(methylsulfonyl)azetidin-3-ylsulfonyl)-2-neopentyl-1-(2-(trifluoromethoxy)ethyl)-1)-1H-benzo[d]imidazole

[Chem.42]

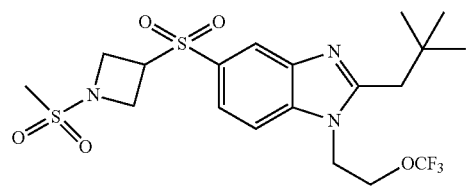

Step A 5-bromo-2-neopentyl-1-(2-(trifluoromethoxy)ethyl)-1H-benzo[d]imidazole

[Chem.43]

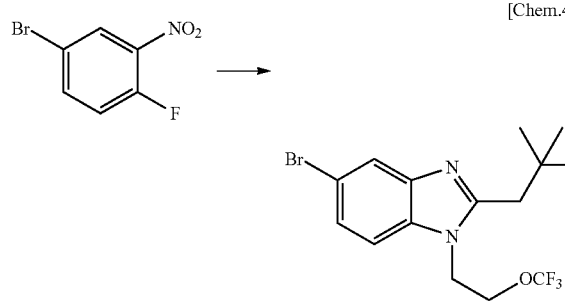

2-(Trifluoromethoxy)ethanamine hydrochloride (3.91 g, 23.6 mmol) and triethylamine (2.56 mL, 18.2 mmol) were dissolved in ethanol (30 mL) at room temperature. Then to the solution was added 4-bromo-1-fluoro-2-nitrobenzene (4.00 g, 18.2 mmol). The mixture was stirred at 75° C. for 14 h. The mixture was concentrated in vacuo and the residue was diluted with ethyl acetate and saturated ammonium chloride aqueous solution to separate. The aqueous layer was extracted with ethyl acetate and the combined organic layers were dried over magnesium sulfate and concentrated in vacuo.

The residue was dissolved in tetrahydrofuran (50 mL) and to the solution was added 5% PLATINUM ON CHARCOAL TYPE 128 PASTE (Johnson Matthey, 262 mg). The mixture was stirred under hydrogen at 3.5 to 4.5 atm for 3 h. The catalyst was filtered off through a celite pad and the filtrate was concentrated in vacuo.

The residue was dissolved in dichloromethane (40 mL). To the solution at 0° C. was added triethylamine (5.11 mL, 36.4 mmol), followed by tert-butylacetyl chloride (2.45 g, 18.2 mmol) in dichloromethane (10 mL). After stirring for 30 min at room temperature, the reaction was quenched with saturated sodium bicarbonate aqueous solution and the mixture was separated. The organic layer was dried over magnesium sulfate and concentrated in vacuo.

The residue was dissolved in toluene (150 mL) and to the mixture was added p-toluenesulfonic acid hydrate (4.15 g, 21.8 mmol). The mixture was refluxed for 6 h with azeotropic removal of water. The mixture was concentrated in vacuo and the residue was diluted with dichloromethane and the solution was basified by 2 mol/L sodium hydroxide aqueous solution. The organic layer was dried over magnesium sulfate and concentrated in vacuo. The crude product was purified by silica gel column chromatography (hexane-ethyl acetate, gradient) to give the title compound (4.14 g, 60%) as a yellow solid.

MS (ESI); 379 [M($^{79}$Br)+H]$^+$, 381 [M($^{81}$Br)+H]$^+$.

$^1$H-NMR (300 MHz, CDCl$_3$) δ: 7.90 (d, J=1.8 Hz, 1H), 7.37 (dd, J=8.8, 1.8 Hz, 1H), 7.16 (d, J=8.8 Hz, 1H), 4.47 (t, J=5.5 Hz, 2H), 4.22 (t, J=5.5 Hz, 2H), 2.80 (s, 2H), 1.09 (s, 9H).

Step B tert-butyl 3-(2-neopentyl-1-(2-(trifluoromethoxy)ethyl)-1H-benzo[d]imidazol-5-ylthio)azetidine-1-carboxylate

[Chem. 44]

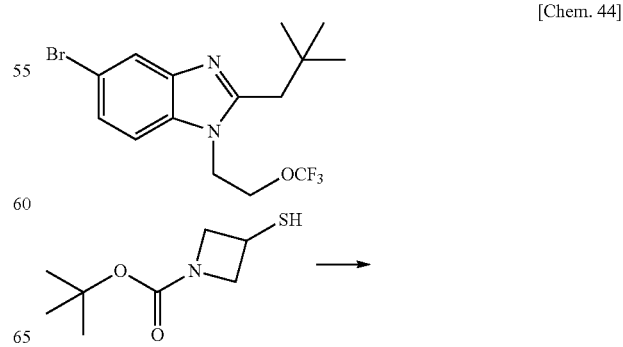

-continued

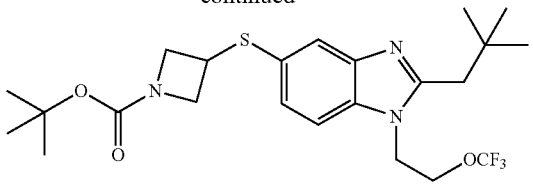

A mixture of 5-bromo-2-neopentyl-1-(2-(trifluoromethoxy)ethyl)-1H-benzo[d]imidazole (STEP A, 265 mg, 0.700 mmol), tert-butyl 3-mercaptoazetidine-1-carboxylate (STEP D of Example 1, 189 mg, 0.999 mmol), Xantphos (20.2 mg, 0.0350 mmol), tris(dibenzylideneacetone)dipalladium (16.0 mg, 0.0175 mmol) and N,N-diisopropylethylamine (245 microL, 1.40 mmol) in 1,4-dioxane (4 mL) was stirred at 160° C. for 1 h under microwave. The mixture was diluted with ethyl acetate and filtered through a celite. The filtrate was concentrated in vacuo and the residue was purified by silica gel column chromatography (hexane-ethyl acetate, gradient) to give the title compound (278 mg, 81%).
MS (ESI) m/z 488 (M+H)+.

Step C 5-(azetidin-3-ylsulfonyl)-2-neopentyl-1-(2-(trifluoromethoxy)ethyl)-1H-benzo[d]imidazole

[Chem. 45]

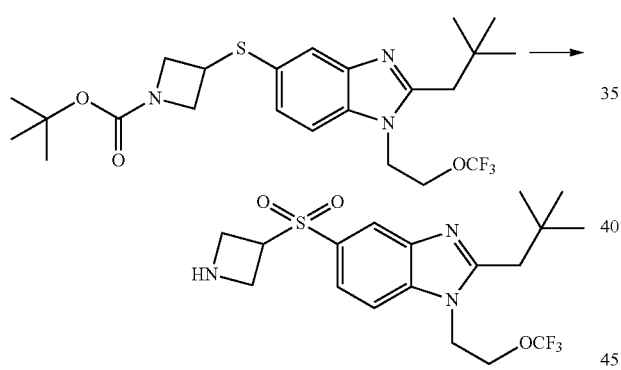

To a solution of tert-butyl 3-(2-neopentyl-1-(2-(trifluoromethoxy)ethyl)-1H-benzo[d]imidazol-5-ylthio)azetidine-1-carboxylate (STEP B, 278 mg, ca.0.570 mmol) in methanol (4 mL) was added 30% hydrogen peroxide aqueous solution (175 microL, 5.70 mmol) and sodium tungstate dihydrate (9.40 mg, 0.0285 mmol) at room temperature. After stirring for 4 h, dimethyl sulfoxide (1 mL) was added to the mixture to quench the reaction. After 10 min, the mixture was concentrated in vacuo.
The residue was diluted with methanol (4 mL) was added chlorotrimethylsilane (1.46 mL). After stirring for 2 h at room temperature, the mixture was concentrated in vacuo. The crude product was purified by reverse phase HPLC (0.4% aqueous ammonia-acetonitrile=96:4 to 4:96) to give the title compound (67.0 mg, 28%) as a white solid.
MS (ESI) m/z 420 (M+H)+.
1H-NMR (300 MHz, CDCl3) δ: 8.30 (d, J=1.7 Hz, 1H), 7.80 (dd, J=8.4, 1.7 Hz, 1H), 7.44 (d, J=8.4 Hz, 1H), 4.55 (t, J=5.5 Hz, 2H), 4.28-4.13(m, 5H), 3.72 (t, J=8.4 Hz, 2H), 2.85 (s, 2H), 1.12 (s, 9H), a peak of NH was not observed.

Step D 5-(1-(methylsulfonyl)azetidin-3-ylsulfonyl)-2-neopentyl-1-(2-(trifluoromethoxy)ethyl)-1)-1H-benzo[d]imidazole

[Chem. 46]

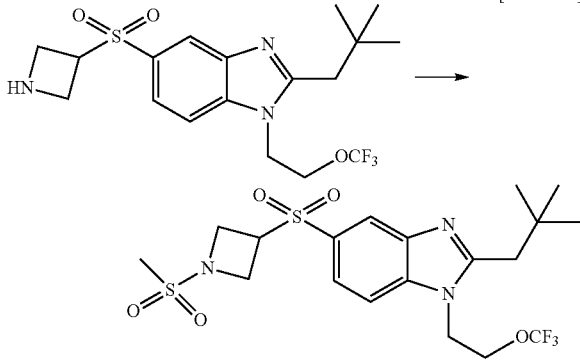

The title compound was prepared according to the procedure described in STEP D of Example 6 using 5-(azetidin-3-ylsulfonyl)-2-neopentyl-1-(2-(trifluoromethoxy)ethyl)-1H-benzo[d]imidazole (STEP C) instead of 2-tert-butyl-1-(cyclopropylmethyl)-5-(piperidin-4-ylmethylsulfonyl)-1H-benzo[d]imidazole dihydrocholide.
MS (ESI) m/z 498 (M+H)+.

Example 8

3-(2-neopentyl-1-(2-(trifluoromethoxy)ethyl)-1H-benzo[d]imidazol-5-ylsulfonyl)azetidine-1-carboxamide

[Chem. 47]

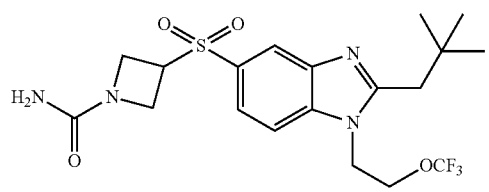

Step A 3-(2-neopentyl-1-(2-(trifluoromethoxy)ethyl)-1H-benzo[d]imidazol-5-ylsulfonyl)azetidine-1-carboxamide

[Chem. 48]

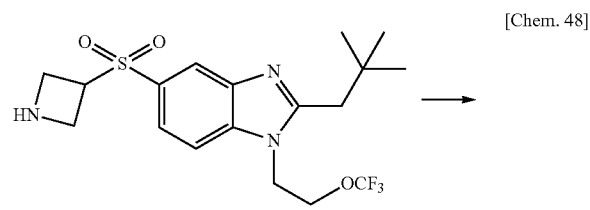

-continued

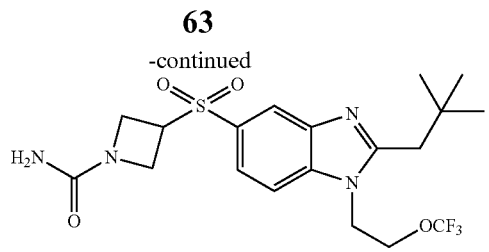

The title compound was prepared according to the procedure described in STEP D of Example 6 using 5-(azetidin-3-ylsulfonyl)-2-neopentyl-1-(2-(trifluoromethoxy)ethyl)-1H-benzo[d]imidazole (STEP C of Example 7) and trimethylsilyl isocyanate instead of methanesulfonyl chloride.

MS (ESI) m/z 463 (M+H)$^+$.

Example 9

1-(4-(1-(cyclopropylmethyl)-2-neopentyl-1H-benzo[d]imidazol-5-ylsulfonyl)-4-(hydroxymethyl)piperidin-1-yl)ethanone

[Chem.49]

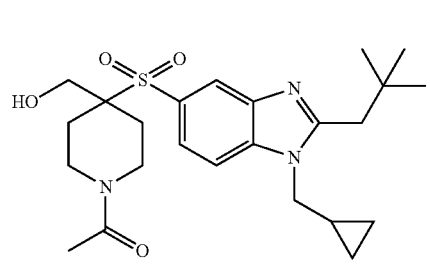

Step A tert-butyl 4-(methanesulfonyloxy)piperidine-1-carboxylate

[Chem.50]

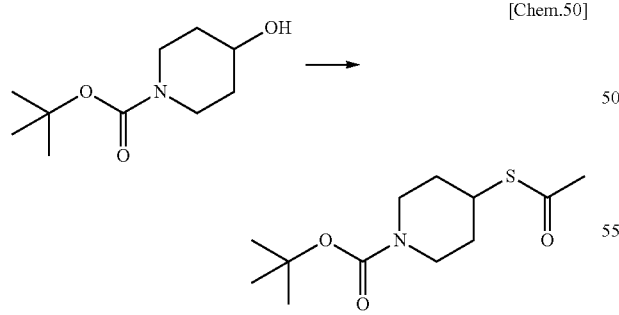

The title compound was prepared according to the procedure described in STEP C of Example 3 using tert-butyl 4-hydroxypiperidine-1-carboxylate instead of tert-butyl 3-(hydroxymethyl)azetidine-1-carboxylate.

$^1$H-NMR (300 MHz, CDCl$_3$) δ: 3.88-3.83 (br, 2H), 3.66-3.56 (m, 1H), 3.06 (ddd, J=13.2, 10.3, 2.9 Hz, 2H), 2.32 (s, 3H), 1.93-1.87 (m, 2H), 1.60-1.40 (2H), 1.45 (s, 9H).

Step B tert-butyl 4-sulfanylpiperidine-1-carboxylate

[Chem. 51]

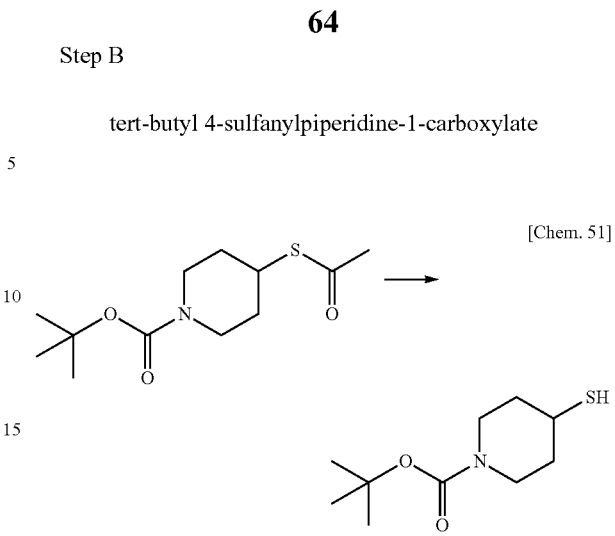

The title compound was prepared according to the procedure described in STEP D of Example 3 using tert-butyl 4-(acetylsulfanyl)piperidine-1-carboxylate instead of tert-butyl 3-(acetylthiomethy)azetidine-1-carboxylate (STEP A).

Step C tert-butyl 4-(1-(cyclopropylmethyl)-2-neopentyl-1H-benzo[d]imidazol-5-ylsulfonyl)piperidine-1-carboxylate

[Chem. 52]

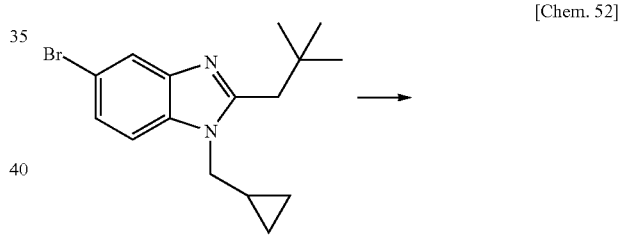

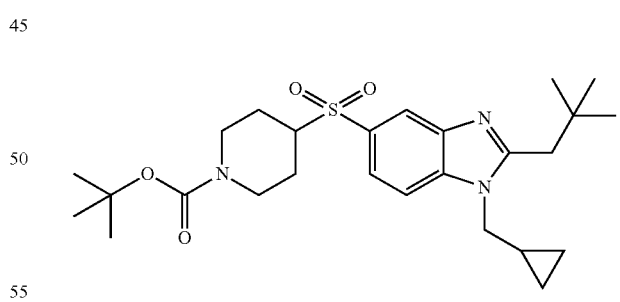

The title compound was prepared according to the procedure described in Step C of Example 2 using tert-butyl 4-mercaptopiperidine-1-carboxylate (STEP B) instead of tert-butyl 3-mercaptoazetidine-1-carboxylate.

MS (ESI) m/z 458 (M+H)$^+$.

$^1$H-NMR (300 MHz, CDCl$_3$) δ: 8.26 (s, 1H), 7.73 (d, J=8.4 Hz, 1H), 7.49 (d, J=8.4 Hz, 1H), 4.29-4.07 (m, 4H), 3.13-3.00 (m, 1H), 2.86 (s, 2H), 2.74-2.55 (m, 2H), 1.71-1.53 (m, 2H), 1.41 (s, 9H), 1.26-1.16 (m, 3H), 1.11 (s, 9H), 0.71-0.59 (m, 2H), 0.47-0.35 (m, 2H).

Step D 1-(cyclopropylmethyl)-2-neopentyl-5-(piperidin-4-ylsulfonyl)-1H-benzo[d]imidazole

[Chem. 53]

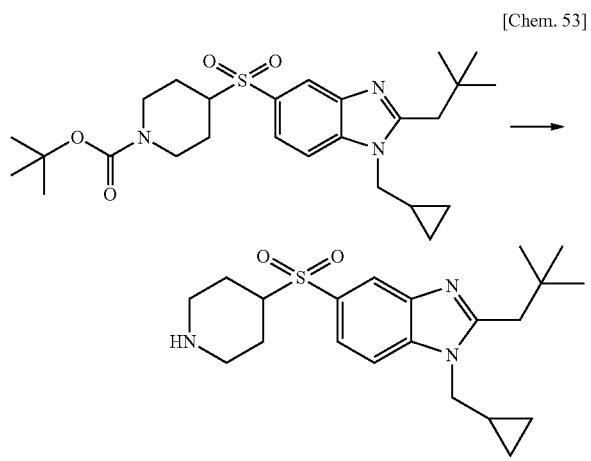

The title compound was prepared according to the procedure described in STEP D of Example 5 using tert-butyl 4-(1-(cyclopropylmethyl)-2-neopentyl-1H-benzo[d]imidazol-5-ylsulfonyl)piperidine-1-carboxylate (STEP C) and tert-butyl 4-((1-(cyclopropylmethyl)-2-neopentyl-1H-benzo[d]imidazol-5-ylsulfonyl)methyl)piperidine-1-carboxylate.

MS (ESI) m/z 390 (M+H)$^+$.

$^1$H-NMR (300 MHz, CDCl$_3$) δ: 8.26 (s, 1H), 7.73 (d, J=8.8 Hz, 1H), 7.47 (d, J=8.8 Hz, 1H), 4.12 (d, J=6.6 Hz, 2H), 3.20-3.00 (m, 3H), 2.85 (s, 2H), 2.61-2.49 (m,2H), 2.10-2.01 (m, 2H), 1.64-1.48 (m, 2H), 1.25-1.14 (m, 1H), 1.11 (s, 9H), 0.69-0.61 (m, 2H), 0.43-0.37 (m, 2H)

Step E 1-(cyclopropylmethyl)-2-neopentyl-5-(1-tritylpiperidin-4-ylsulfonyl)-1H-benzo[d]imidazole

[Chem. 54]

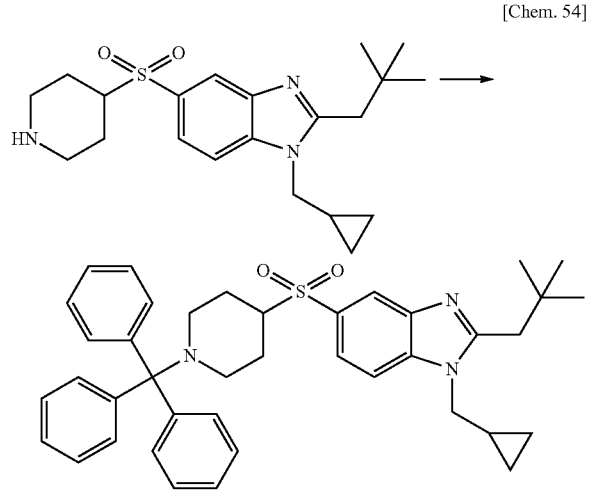

To a solution of 1-(cyclopropylmethyl)-2-neopentyl-5-(piperidin-4-ylsulfonyl)-1H-benzo[d]imidazole (STEP D, 1.31 g, 3.36 mmol) and triethylamine (945 microL, 6.73 mmol) in dichloromethane (12 mL) was added triphenylmethyl chloride (1.22 g, 4.37 mmol) at room temperature. After stirring for 14 h, the mixture was diluted with dichloromethane and washed with saturated sodium bicarbonate aqueous solution. The organic layer was dried over sodium sulfate and concentrated in vacuo. The precipitate was washed with a mixture of diethyl ether and hexane (1:1) to give the title compound (1.99 g, 94%) as a white solid.

$^1$H-NMR (300 MHz, CDCl$_3$) δ: 8.26 (d, J=1.5 Hz, 1H), 7.72 (dd, J=8.8, 1.5 Hz, 1H), 7.47 (d, J=8.8 Hz, 1H), 4.11 (d, J=6.6 Hz, 2H), 3.27-3.18 (m, 2H), 2.84 (s, 2H), 2.82-2.70 (m, 1H), 2.19-2.04 (m, 2H), 1.97-1.87 (m, 2H), 1.34-1.13 (m, 3H), 1.10 (s, 9H), 0.66-0.59 (m, 2H), 0.43-0.34 (m, 2H).

Step F (4-(1-(cyclopropylmethyl)-2-neopentyl-1H-benzo[d]imidazol-5-ylsulfonyl)-1-tritylpiperidin-4-yl)methanol

[Chem. 55]

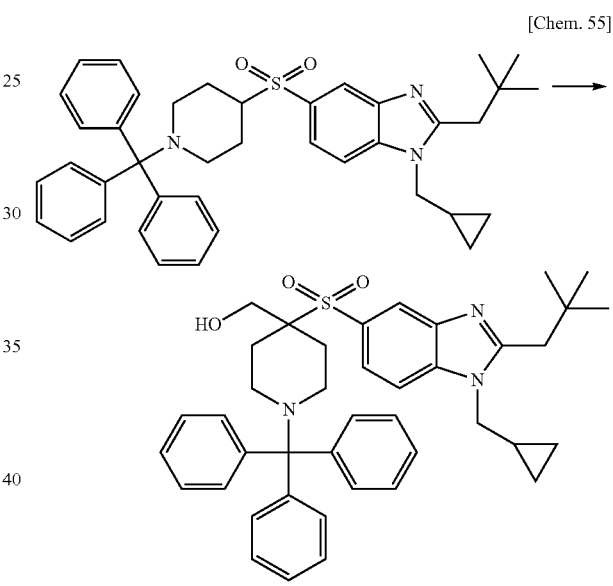

To a solution of 1-(cyclopropylmethyl)-2-neopentyl-5-(1-tritylpiperidin-4-ylsulfonyl)-1H-benzo[d]imidazole (STEP E, 2.05 g, 3.24 mmol) in tetrahydrofuran (60 mL) at −60° C. was added lithium diisopropylamide (1.8 mol/L heptane/tetrahydrofuran/ethylbenzene solution, 2.34 mL, 4.22 mmol). After the mixture was warmed up to −40° C. over a period of 20 min and then stirred for 40 min at the same temperature, methyl cyanoformate (828 mg, 9.73 mmol) in tetrahydrofuran (3 mL) was added to the mixture. The mixture was stirred at 0° C. for 1.5 h. The reaction was quenched with water and the mixture was extracted with ethyl acetate. The organic layer was washed with brine, dried over sodium sulfate and concentrated in vacuo. The residue was purified by silica gel column chromatography (dichloromethane-ethyl acetate, gradient) to give 4:1 mixture of the title compound and the starting material (2.15 g).

MS (ESI) m/z 690 (M+H)$^+$.

To a suspension of lithium aluminum hydride (317 mg, 9.35 mmol) in tetrahydrofuran (15 mL) was added the obtained mixture (2.15 g) in tetrahydrofuran (10 mL) at 0° C. After 1 h, the reaction was quenched with sodium sulfate decahydrate and potassium fluoride. The mixture was filtered through a celite and the filtrate was concentrated in vacuo. The residue was purified by silica gel column chromatography (dichloromethane-ethyl acetate, gradient) to give the title compound (1.43 g, 69%) as a solid.

MS (ESI) m/z 662 (M+H)$^+$.

$^1$H-NMR (300 MHz, CDCl$_3$) δ: 8.31 (d, J=1.5 Hz, 1H), 7.76 (dd, J=8.8, 1.5 Hz, 1H), 7.51-7.08 (m, 15H), 7.50 (d, J=8.8 Hz, 1H), 4.13 (d, J=6.6 Hz, 2H), 3.49 (d, J=5.4 Hz, 2H), 3.18 (t, J=6.9 Hz, 1H), 3.09-2.97 (m, 2H), 2.86 (s, 2H), 2.58-2.43 (m, 2H), 1.77-1.66 (m, 2H), 1.55-1.41 (m, 2H), 1.28-1.05 (m, 1H), 1.12 (s, 9H), 0.68-0.61 (m, 2H), 0.43-0.37 (m, 2H).

Step G (4-(1-(cyclopropylmethyl)-2-neopentyl-1H-benzo[d]imidazol-5-ylsulfonyl)piperidin-4-yl)methanol

[Chem. 56]

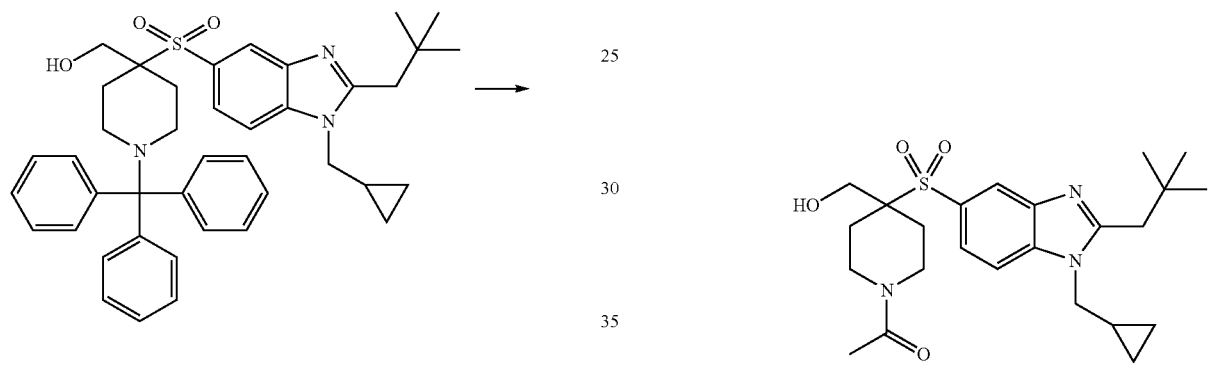

To a solution of (4-(1-(cyclopropylmethyl)-2-neopentyl-1H-benzo[d]imidazol-5-ylsulfonyl)-1-tritylpiperidine-4-yl)methanol (STEP F, 300 mg, 0.453 mmol) in dichloromethane (6 mL) was trifluoroacetic acid (2 mL). After 20 min, the mixture was concentrated in vacuo and the residue was diluted with methanol and the solution was filtered through strong cationic exchange column (SCX). The column was washed with 1 mol/L ammonia methanol to wash out the product. The filtrate was concentrated in vacuo to give the title compound (200 mg, quantitative yield).

MS (ESI) m/z 420 (M+H)$^+$.

Step H 1-(4-(1-(cyclopropylmethyl)-2-neopentyl-1H-benzo[d]imidazol-5-ylsulfonyl)-4-(hydroxymethyl)piperidin-1-yl)ethanone

[Chem. 57]

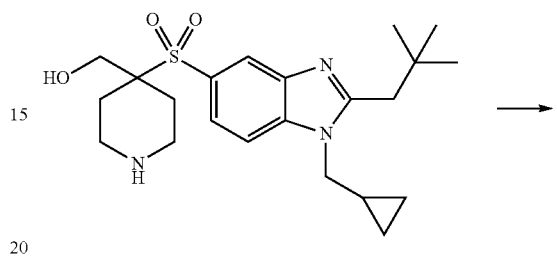

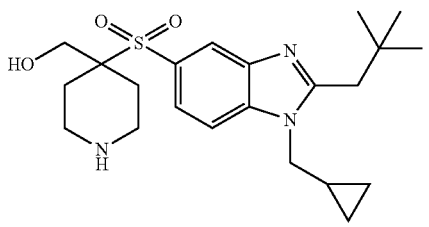

The title compound was prepared according to the procedure described in STEP D of Example 6 using (4-(1-(cyclopropylmethyl)-2-neopentyl-1H-benzo[d]imidazol-5-ylsulfonyl)piperidin-4-yl)methanol (STEP G) and acetyl chloride instead of methanesulfonyl chloride.

MS (ESI) m/z 462 (M+H)$^+$.

Example 10

(4-(1-(cyclopropylmethyl)-2-neopentyl-1H-benzo[d]imidazol-5-ylsulfonyl)-1-(methylsulfonyl)piperidin-4-yl)methanol

[Chem.58]

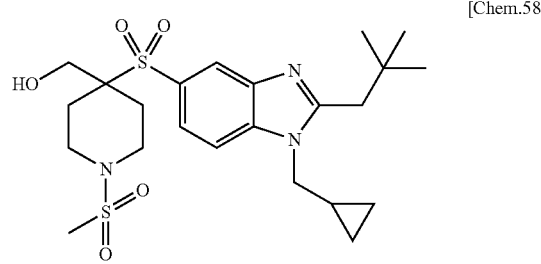 [SMILES: CC(C)(C)Cc1nc2cc(S(=O)(=O)C3(CO)CCN(S(C)(=O)=O)CC3)ccc2n1CC1CC1]

Step A (4-(1-(cyclopropylmethyl)-2-neopentyl-1H-benzo[d]imidazol-5-ylsulfonyl)-1-(methylsulfonyl)piperidin-4-yl)methanol

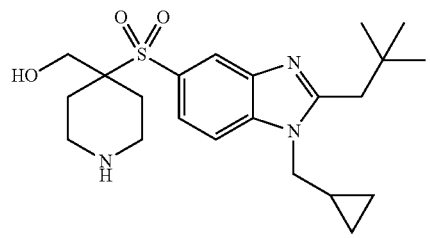

[Chem.59]

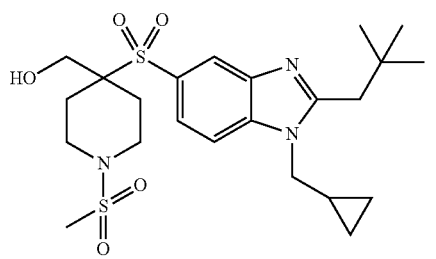

The title compound was prepared according to the procedure described in STEP D of Example 6 using (4-(1-(cyclopropylmethyl)-2-neopentyl-1H-benzo[d]imidazol-5-ylsulfonyl)piperidin-4-yl)methanol (STEP G of Example 9).

MS (ESI) m/z 498 (M+H)⁺.

Example 11

4-[2-(2,2-dimethylpropyl)-1-[(4-hydroxyoxan-4-yl)methyl]-1H-1,3-benzo[d]imidazole-5-sulfonyl]piperidine-1-carboxamide

[Chem.60]

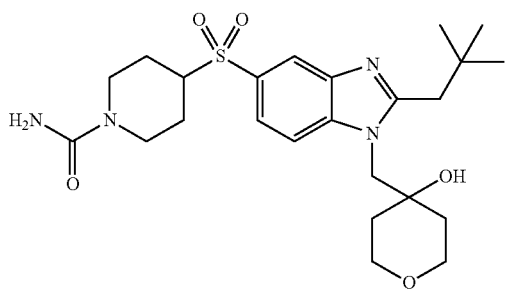

Step A 4-(aminomethyl)oxan-4-ol

[Chem.61]

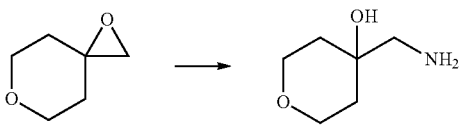

The methanol solution of 1,6-dioxaspiro[2.5]octane (3.15 g, 27.6 mmol) was added to the 25% ammonia aqueous solution (50.0 mL, 27.6 mmol) at 0° C. The mixture was warmed to room temperature and stirred for 18 h. The reaction mixture was concentrated in vacuo. The crude product was used for next step reaction without purification.

MS (ESI) m/z 130 (M−H)⁻.

Step B

4-{[5-bromo-2-(2,2-dimethylpropyl)-1H-1,3-benzodiazol-1-yl]methyl}oxa-4-ol

[Chem.62]

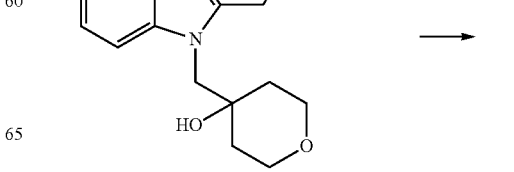

The title compound was prepared according to the procedure described in STEP A of Example 1 using 4-(aminomethyl)oxan-4-ol (STEP A) instead of N,N-dimethylethylenediamine.

MS (ESI) m/z 381(M+H)+, 379 (M−H)⁻.

Step C tert-butyl 4-[2-(2,2-dimethylpropyl)-1-[(4-hydroxyoxan-4-yl)methyl]-1,3-benzodiazole-5-sulfonyl]piperidine-1-carboxylate -continued

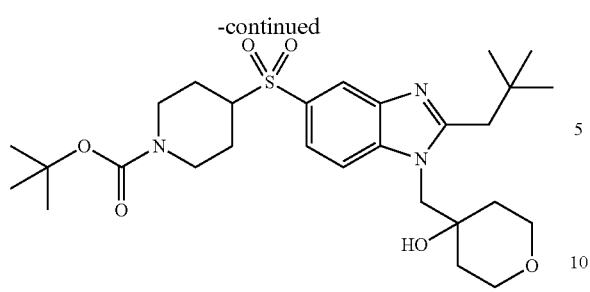

The title compound was prepared according to the procedure described in STEP E of Example 3 using 4-{[5-bromo-2-(2,2-dimethylpropyl)-1H-1,3-benzodiazol-1-yl]methyl}oxan-4-ol (STEP B) instead of 1-(5-bromo-2-neopentyl-1H-benzo[d]imidazol-1-yl)-2-methylpropan-2-ol and tert-butyl 4-sulfanylpiperidine-1-carboxylate instead of tert-butyl 3-mercaptoazetidine-1-carboxylate.

MS (ESI) m/z 550 (M+H)+, 548(M−H)−.

Step D

4-{[2-(2,2-dimethylpropyl)-5-(piperidine-4-sulfonyl)-1,3-benzodiazol-1-yl]methyl}oxan-4-ol

[Chem.64]

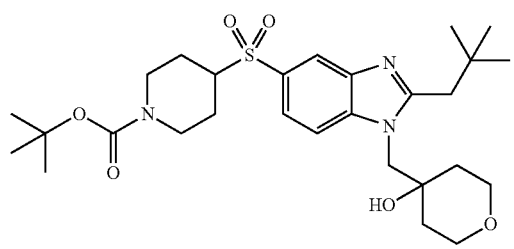 →

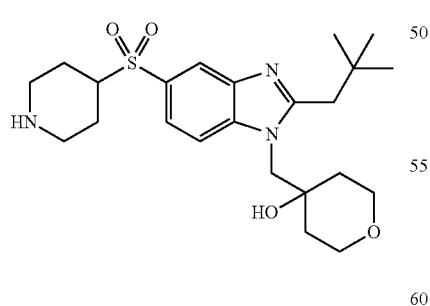

The title compound was prepared according to the procedure described in STEP F of Example 3 using 4-[2-(2,2-dimethylpropyl)-1-[(4-hydroxyoxan-4-yl)methyl]-1,3-benzodiazole-5-sulfonyl]piperidine-1-carboxylate (STEP C) instead of 3-((1-(cyclopropylmethyl)-2-neopentyl-1H-benzo[d]imidazol-5-ylsulfonyl)methyl)azetidine-1-carboxylate MS (ESI) m/z 450 (M+H)+.

Step E

4-[2-(2,2-dimethylpropyl)-1-[(4-hydroxyoxan-4-yl)methyl]-1H-1,3-benzo[d]imidazole-5-sulfonyl]piperidine-1-carboxamide

[Chem.65]

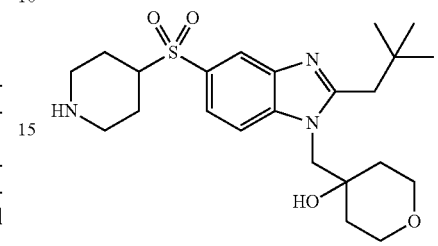

→

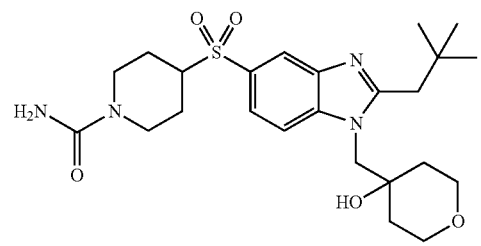

The title compound was prepared according to the procedure described in STEP D of Example 6 using 4-((2-neopentyl-5-(piperidin-4-ylsulfonyl)-1H-benzo[d]imidazol-1-yl)methyl)tetrahydro-2H-pyran-4-ol (STEP E) and trimethylsilyl isocyanate instead of methanesulfonyl chloride.

MS (ESI) m/z 493 (M+H)+.

Example 12

4-(4-((1-(cyclopropylmethyl)-2-neopentyl-1H-benzo[d]imidazol-5-ylsulfonyl)methyl)piperidine-1-carbonyl)imidazolidin-2-one

[Chem.66]

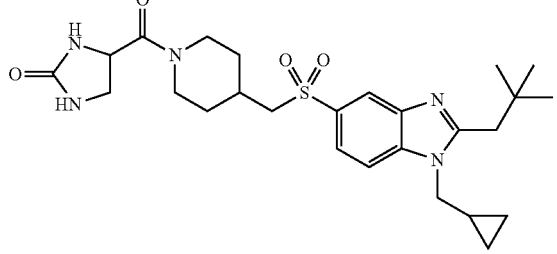

Step A 4-(4-((1-(cyclopropylmethyl)-2-neopentyl-1H-benzo[d]imidazol-5-ylsulfonyl)methyl)piperidine-1-carbonyl)imidazolidin-2-one

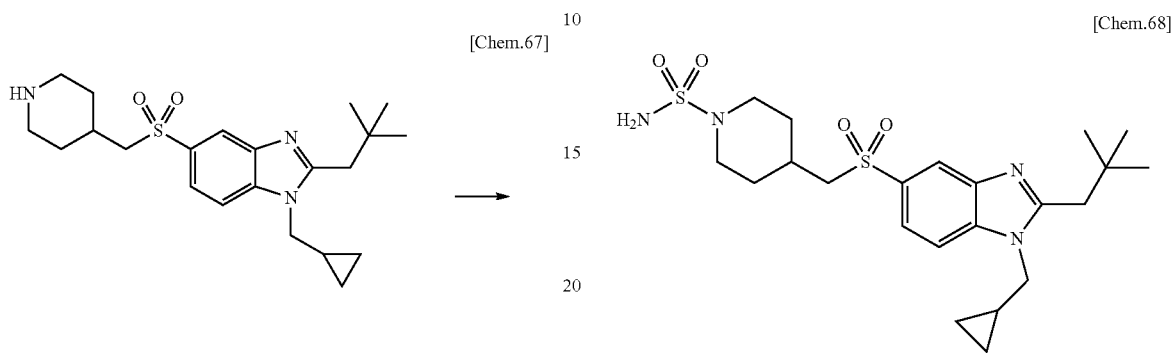

[Chem.67]

To a solution of 2-imidazolidone-4-carboxylic acid (12 mg, 0.093 mmol) in dichloromethane (1 mL) was added 1-(cyclopropylmethyl)-2-neopentyl-5-(piperidin-4-ylmethylsulfonyl)-1H-benzo[d]imidazole (STEP D of Example 5, 25 mg, 0.062 mmol), triethylamine (13 microL, 0.093 mmol) and 2-(1H-benzotriazole-1-yl)-1,1,3,3-tetramethyluronium hexafluorophosphate (35 mg, 0.093 mmol) at room temperature, then stirred. After 15 h, 2-imidazolidone-4-carboxylic acid (12 mg, 0.093 mmol) was added to the mixture and stirred at room temperature. After 2 days, the mixture was washed with water (0.5 mL). The organic layer was mounted to a strong cationic exchange column (SCX) which was preconditioning with methanol (4 mL). SCX was washed with methanol (4 mL). Finally SCX was washed with 1 mol/L ammonia in methanol (5 mL), the product was collected a collection tube and concentrated at under reduced pressure by centrifugal concentrator. The residue (25 mg) was purified by prep-LC-MS("process A").

MS (ESI) m/z 516 (M+H)$^+$.

Example 13

4-{[1-(cyclopropylmethyl)-2-(2,2-dimethylpropyl)-1H-1,3-benzodiazole-5-sulfonyl]methyl}piperidine-1-sulfonamide

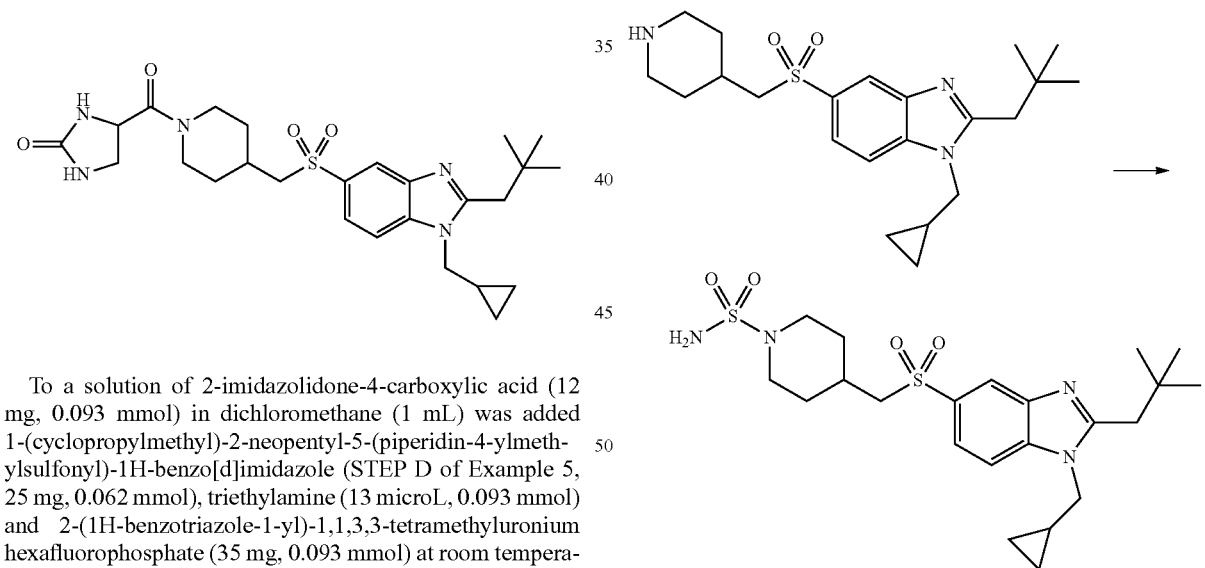

[Chem.68]

Step A

4-{[1-(cyclopropylmethyl)-2-(2,2-dimethylpropyl)-1H-1,3-benzodiazole-5-sulfonyl]methyl}piperidine-1-sulfonamide.

[Chem.69]

The mixture of 1-(cyclopropylmethyl)-2-(2,2-dimethylpropyl)-5-[(piperidin-4-ylmethane)sulfonyl]-1,3-benzodiazole (STEP D of Example 5, 25 mg, 0.062 mmol), sulfamide (15 mg, 0.16 mmol) and 1,4-dioxane was refluxed for 6 h. The reaction mixture was concentrated in vacuo and extracted with ethyl acetate (20 mL) and water (30 mL). The organic layer was washed with water (20 mL) and brine (15 mL), dried over magnesium sulfate. The crude product (27 mg) was purified by prep LC-MS("process A").

MS (ESI) m/z 483 (M+H)$^+$, 481 (M−H)$^-$.

Example 14

3-(1-((1-acetylpiperidin-4-yl)methyl)-2-neopentyl-1H-benzo[d]imidazol-5-ylsulfonyl)azetidine-1-carboxamide

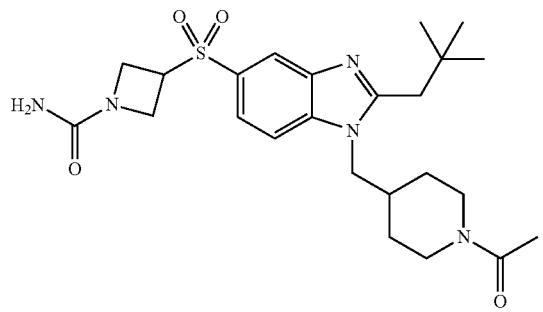

[Chem.70]

Step A tert-butyl 4-((5-bromo-2-neopentyl-1H-benzo[d]imidazol-1-yl)methyl)piperidine-1-carboxylate

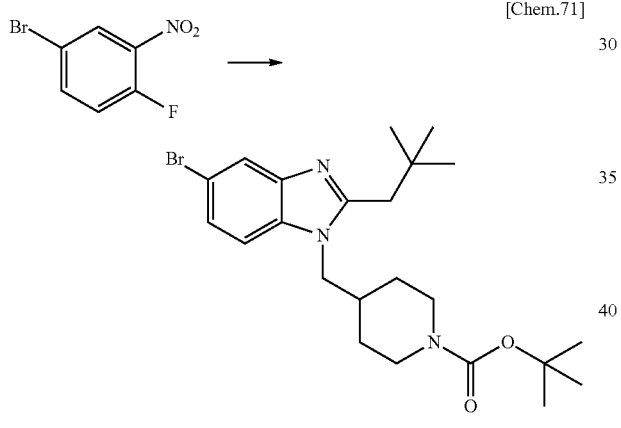

[Chem.71]

Tert-butyl 4-(aminomethyl)piperidine-1-carboxylate (5.60 g, 26.1 mmol) and triethylamine (6.39 mL, 45.5 mmol) were dissolved in ethanol (30 mL). Then to the solution was added 4-bromo-1-fluoro-2-nitrobenzene (5.00 g, 22.7 mmol) in ethanol (10 mL) at room temperature. After refluxing for 2 h, the mixture was concentrated in vacuo. The residue was diluted with ethyl acetate and the solution was washed with saturated ammonium chloride aqueous solution, dried over magnesium sulfate and concentrated.

The residue was dissolved in tetrahydrofuran (60 mL). To the solution was added 5% PLATINUM ON CHARCOAL TYPE 128 PASTE (Johnson Matthey, 471 mg) and the mixture was stirred under hydrogen at 3.5 to 4.5 atm for 4 h. The mixture was filtered through celite and the filtrate was concentrated in vacuo.

The residue was dissolved in dichloromethane. To the solution at 0° C. was added triethylamine (6.39 mL, 45.5 mmol), followed by tert-butylacetyl chloride (3.05 g, 22.7 mmol) in dichloromethane (10 mL). After stirring for 30 min at room temperature, the reaction was quenched with saturated sodium bicarbonate aqueous solution and the mixture was separated. The organic layer was dried over magnesium sulfate and concentrated in vacuo.

The residue was dissolved in acetonitrile (50 mL) and added 12 mol/L hydrochloric acid (15 mL). After refluxing for 28 h, the mixture was basified by 6 mol/L sodium hydroxide aqueous solution and concentrated. The residue was extracted with dichloromethane and the combined organic layers were dried over sodium sulfate and concentrated in vacuo.

The residue was dissolved in dichloromethane (80 mL). To the solution was added triethylamine (4.79 mL, 34.1 mmol) and di-tert-butyl dicarbonate (6.33 mL, 27.3 mmol) at room temperature. After stirring for 1 h at the same temperature, the mixture was concentrated. The residue was purified by silica gel column chromatography (hexane-ethyl acetate, gradient) to give the title compound (7.78 g, 74%).

MS (ESI) m/z 464 [M($^{79}$Br)+H$^+$, 466 [M($^{81}$Br)+H$^+$.

$^1$H-NMR (300 MHz, CDCl$_3$) δ: 7.87(d, J=1.5 Hz, 1H), 7.34 (dd, J=8.6, 1.5 Hz, 1H), 7.16 (d, J=8.6 Hz, 1H), 4.21-4.06 (m, 2H), 4.02 (d, J=7.3 Hz, 2H), 2.78 (s, 2H), 2.65-2.50 (m, 2H), 2.02-1.88 (m, 1H), 1.62-1.31 (m, 2H), 1.45 (s, 9H), 1.18-1.17 (m, 2H), 1.06 (s, 9H).

Step B 1-(4-((5-bromo-2-neopentyl-1H-benzo[d]imidazol-1-yl)methyl)piperidin-1-yl)ethanone

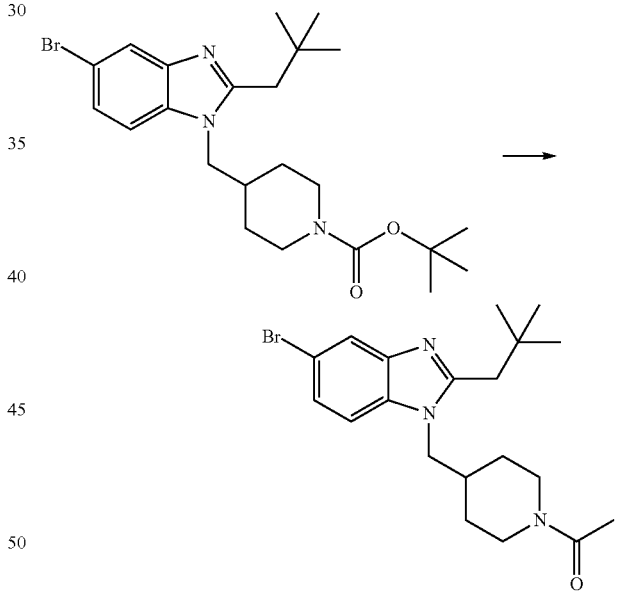

[Chem. 72]

To a solution of tert-butyl 4-((5-bromo-2-neopentyl-1H-benzo[d]imidazol-1-yl)methyl)piperidine-1-carboxylate (STEP A, 740 mg, 1.59 mmol) in methanol (8 mL) was added chlorotrimethylsilane (4 mL). After stirring for 17 h, the mixture was concentrated in vacuo. The residue was diluted with dichloromethane (8 mL) and added triethylamine (2.24 mL, 15.9 mmol) and acetyl chloride (227 microL, 3.19 mmol). After 20 min, the mixture was diluted with ethyl acetate and washed with water, dried over sodium sulfate and concentrated in vacuo. The residue was purified by silica gel column chromatography (dichloromethane-methanol, gradient) to give the title compound (630 mg, 97%) as an amorphous.

MS (ESI) m/z 406 [M($^{79}$Br)+H$^+$, 408 [M($^{81}$Br)+H$^+$.

$^1$H-NMR (300 MHz, CDCl$_3$) δ: 7.88(d, J=1.6 Hz, 1H), 7.34 (dd, J=8.6, 1.6 Hz, 1H), 7.15 (d, J=8.6 Hz, 1H), 4.73-4.63 (m, 1H), 4.11-3.95 (m, 2H), 3.87-3.76 (m, 1H), 2.98-2.87 (m, 1H), 2.77 (s, 2H), 2.49-2.37 (m, 1H), 2.15-2.01 (m, 1H), 2.08 (s, 3H), 1.65-1.51 (m, 2H), 1.32-1.16 (m, 2H), 1.07 (s, 9H).

Step C tert-butyl 3-(1-((1-acetylpiperidin-4-yl)methyl)-2-neopentyl-1H-benzo[d]imidazol-5-ylsulfonyl)azetidine-1-carboxylate

[Chem. 73]

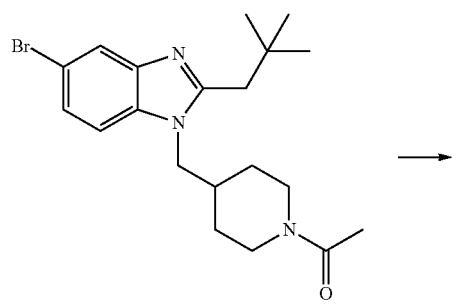

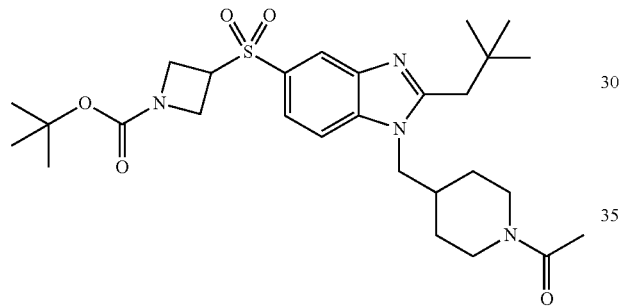

The title compound was prepared according to the procedure described in Step C of Example 2 using 1-(4-((5-bromo-2-neopentyl-1H-benzo[d]imidazol-1-yl)methyl)piperidin-1-yl)ethanone (STEP B).

MS (ESI) m/z 515 (M+H)$^+$.

Step D 1-(4-((5-(azetidin-3-ylsulfonyl)-2-neopentyl-1H-benzo[d]imidazol-1-yl)methyl)piperidin-1-yl)ethanone

[Chem. 74]

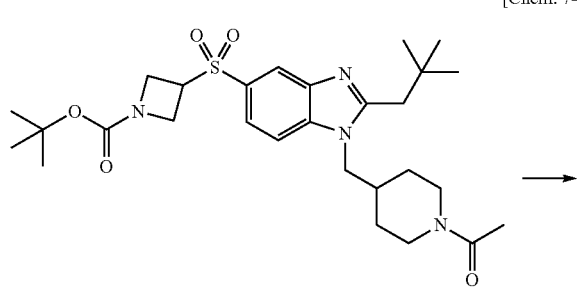

-continued

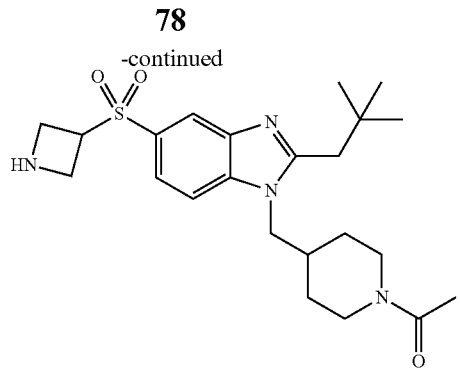

To a solution of tert-butyl 3-(1-((1-acetylpiperidin-4-yl)methyl)-2-neopentyl-1H-benzo[d]imidazol-5-ylsulfonyl)azetidine-1-carboxylate (STEP C, 220 mg, 0.402 mmol) in dichloromethane (2 mL) was added trifluoroacetic acid (1 mL) at room temperature. After stirring for 40 min, the mixture was concentrated. The residue was diluted with methanol (10 mL) and the solution was filtered through strong cationic exchange column (SCX). The column was washed with 1 mol/L ammonia in methanol (10 mL) to wash out the title compound (176 mg, 98%).

ESI-MS m/z 447 (M+H)$^+$.

Step E 3-(1-((1-acetylpiperidin-4-yl)methyl)-2-neopentyl-1H-benzo[d]imidazol-5-ylsulfonyl)azetidine-1-carboxamide

[Chem. 75]

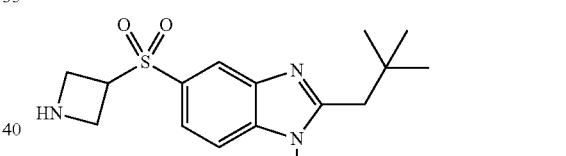

The title compound was prepared according to the procedure described in STEP D of Example 6 using 1-(4-((5-(azetidin-3-ylsulfonyl)-2-neopentyl-1H-benzo[d]imidazol-1-yl)methyl)piperidin-1-yl)ethanone (STEP D) and trimethylsilyl isocyanate instead of methanesulfonyl chloride.

MS (ESI) m/z 489 (M+H)$^+$.

Example 15

1-(cyclopropylmethyl)-2-(2,2-dimethylpropyl)-5-{[(1-methanesulfonylpiperidin-4-yl)methane]sulfonyl}-1H-1,3-benzodiazole

[Chem. 76]

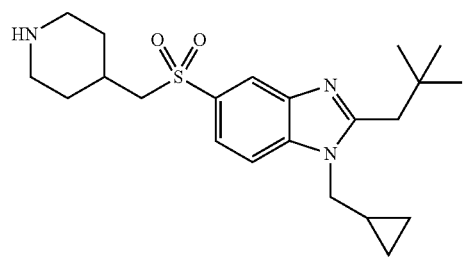

→

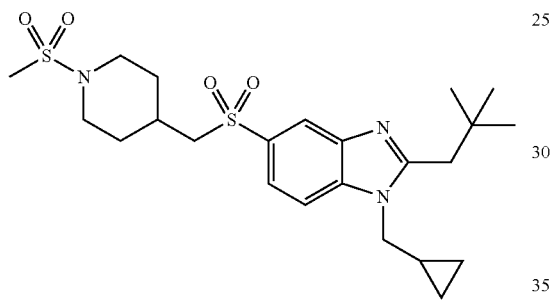

The title compound was prepared according to the procedure described in STEP D of Example 6 using 1-(cyclopropylmethyl)-2-(2,2-dimethylpropyl)-5-[(piperidin-4-ylmethane)sulfonyl]-1,3-benzodiazole (STEP D of Example 5) instead of 5-(azetidin-3-ylmethylsulfonyl)-1-(cyclopropylmethyl)-2-neopentyl-1H-benzo[d]imidazole.

MS (ESI) m/z 482 (M+H)$^+$.

Example 16

1-(4-{[1-(cyclopropylmethyl)-2-(2,2-dimethylpropyl)-1H-1,3-benzodiazole-5-sulfonyl]methyl}piperidin-1-yl)ethan-1-one

[Chem. 77]

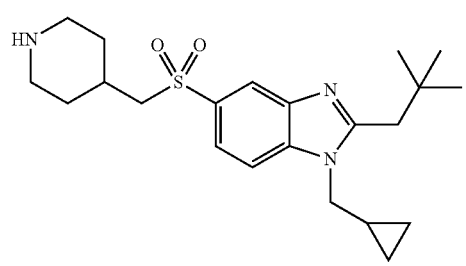

→

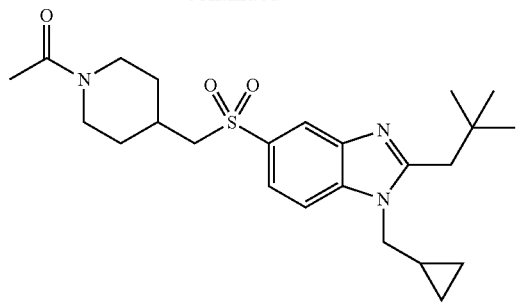

The title compound was prepared according to the procedure described in STEP D of Example 6 using 1-(cyclopropylmethyl)-2-(2,2-dimethylpropyl)-5-[(piperidin-4-ylmethane)sulfonyl]-1,3-benzodiazole (STEP D of Example 5) and acetyl chloride instead of 5-(azetidin-3-ylmethylsulfonyl)-1-(cyclopropylmethyl)-2-neopentyl-1H-benzo[d]imidazole and methanesulfonyl chloride.

MS (ESI) m/z 446 (M+H)$^+$.

Example 17

1-(cyclopropylmethyl)-2-(2,2-dimethylpropyl)-5-(1-methanesulfonylazetidine-3-sulfonyl)-1H-1,3-benzodiazole

[Chem. 78]

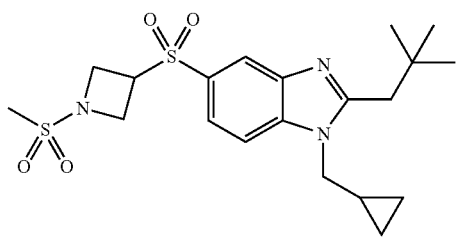

Step A 5-(azetidine-3-sulfonyl)-1-(cyclopropylmethyl)-2-(2,2-dimethylpropyl)-1H-1,3-benzodiazole

[Chem. 79]

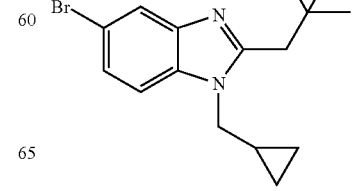

→

-continued

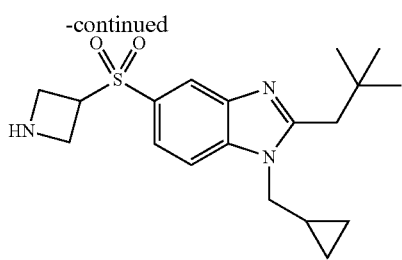

The title compound was prepared according to the procedure described in STEP E and F of Example 3 using tert-butyl 3-mercaptoazetidine-1-carboxylate (STEP D of Example 1) instead of tert-butyl 3-(sulfanylmethyl)azetidine-1-carboxylate.

MS (ESI) m/z 362 (M+H)+.

Step B 1-(cyclopropylmethyl)-2-(2,2-dimethylpropyl)-5-(1-methanesulfonylazetidine-3-sulfonyl)-1H-1,3-benzodiazole

[Chem. 80]

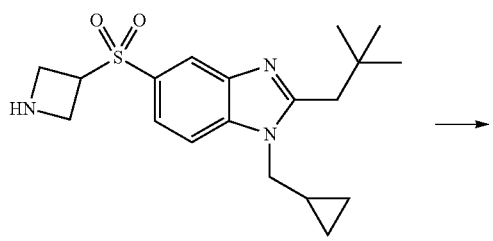

The title compound was prepared according to the procedure described in STEP D of Example 6 using 5-(azetidine-3-sulfonyl)-1-(cyclopropylmethyl)-2-(2,2-dimethylpropyl)-1H-1,3-benzodiazole (STEP A) instead of 2-tert-butyl-1-(cyclopropylmethyl)-5-(piperidin-4-ylmethylsulfonyl)-1H-benzo[d]imidazole dihydrocholide.

MS (ESI) m/z 440 (M+H)+.

Example 18

(3R)-3-[1-(cyclopropylmethyl)-2-(2,2-dimethylpropyl)-1H-1,3-benzodiazole-5-sulfonyl]pyrrolidine-1-carboxamide

[Chem. 81]

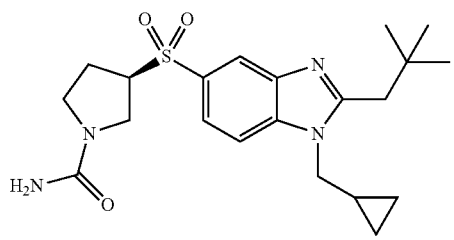

Step A tert-butyl (3S)-3-hydroxypyrrolidine-1-carboxylate

[Chem. 82]

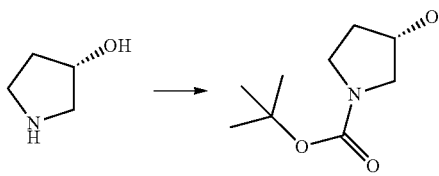

To a solution of (S)-3-pyrrolidinol (1.05 g, 12.0 mmol) in dichloromethane (20 mL) were added triethylamine (2.11 mL, 15.0 mmol) and di-tert-butyl dicarbonate (2.32 mL, 10.0 mmol) at room temperature. After 1 h, the reaction mixture was concentrated. The residue was diluted with ethyl acetate and washed with saturated ammonium chloride aqueous solution. The organic layer was dried over sodium sulfate and concentrated. The crude product (2.00 g, 1.07 mmol) was used for the next step without purification.

MS (ESI) m/z 186 (M−H)−.

Step B tert-butyl (3R)-3-(acetylsulfanyl)pyrrolidine-1-carboxylate

[Chem. 83]

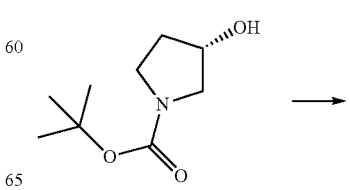

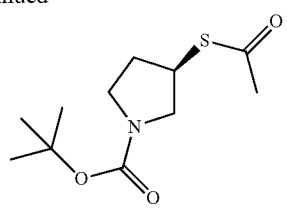

The title compound was prepared according to the procedure described in STEP C of Example 3 using tert-butyl (3S)-3-hydroxypyrrolidine-1-carboxylate (STEP A) instead of tert-butyl 3-(hydroxymethyl)azetidine-1-carboxylate.

MS (ESI) m/z 246 (M+H)$^+$.

Step C tert-butyl (3R)-3-sulfanylpyrrolidine-1-carboxylate

[Chem. 84]

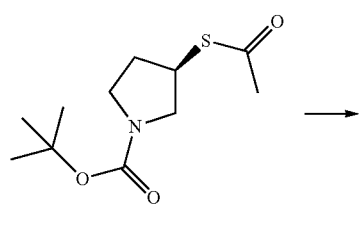

The title compound was prepared according to the procedure described in STEP D of Example 3 using tert-butyl (3R)-3-(acetylsulfanyl)pyrrolidine-1-carboxylate (STEP B) instead of tert-butyl 3-(acetylthiomethyl)azetidine-1-carboxylate.

MS (ESI) m/z 202 (M−H)$^−$.

Step D 1-(cyclopropylmethyl)-2-(2,2-dimethylpropyl)-5-1 (3R-pyrrolidine-3-sulfonyl]-1 H-1,3-benzodiazole

[Chem. 85]

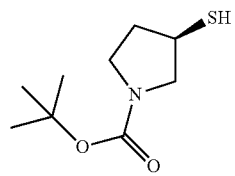

The title compound was prepared according to the procedure described in STEP E and F of Example 3 using tert-butyl (3R)-3-sulfanylpyrrolidine-1-carboxylate (STEP C) instead of tert-butyl 3-(sulfanylmethyl)azetidine-1-carboxylate.

MS (ESI) m/z 376 (M+H)$^+$.

Step E (3R)-3-[1-(cyclopropylmethyl)-2-(2,2-dimethylpropyl)-1H-1,3-benzodiazole-5-sulfonyl]pyrrolidine-1-carboxamide

[Chem. 86]

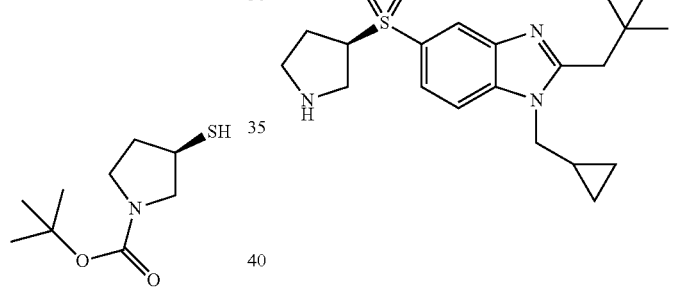

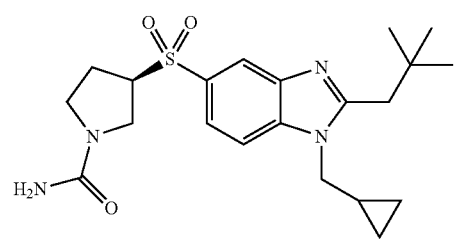

The title compound was prepared according to the procedure described in STEP D of Example 6 using 1-(cyclopropylmethyl)-2-(2,2-dimethylpropyl)-5-[(3R)-pyrrolidine-3-sulfonyl]-1H-1,3-benzodiazole (STEP D) and trimethylsilyl isocyanate instead of methanesulfonyl chloride.

MS (ESI) m/z 440 (M+H)$^+$.

Example 19

N,N-dimethyl-2-(5-(1-(methylsulfonyl)azetidin-3-ylsulfonyl)-2-neopentyl-1H-benzo[d]imidazol-1-yl)ethanamine citrate

[Chem. 87]

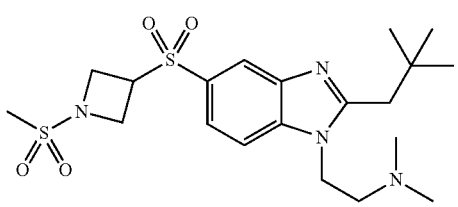

Step A

N,N-dimethyl-2-(5-(1-(methylsulfonyl)azetidin-3-ylsulfonyl)-2-neopentyl-1H-benzo[d]imidazol-1-yl)ethanamine

[Chem. 88]

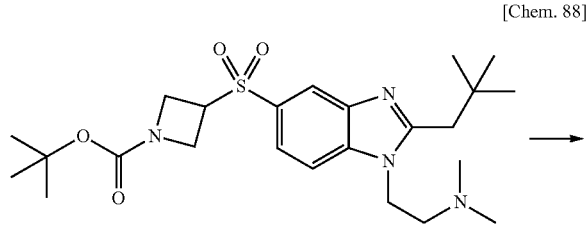

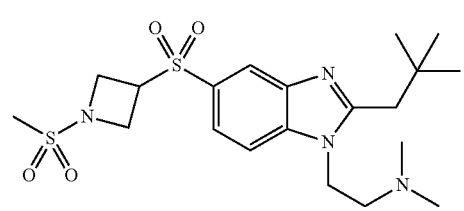

To a solution of tert-butyl 3-(1-(2-(dimethylamino)ethyl)-2-neopentyl-1H-benzo[d]imidazol-5-ylsulfonyl)azetidine-1-carboxylate (prepared in STEP F of Example 1, 575 mg, 1.20 mmol) in methanol (6 mL) was added chlorotrimethylsilane (768 microL, 6.01 mmol). After stirring for 1 h at 50° C., the mixture was concentrated in vacuo.

The residue was diluted with dichloromethane (10 mL). To the mixture was added triethylamine (844 microL, 6.01 mmol), followed by a solution of methanesulfonyl chloride (140 microL, 1.80 mmol) in dichloromethane (2 mL) at 0° C. After stirring for 30 min, to the mixture was added sodium bicarbonate aqueous solution to separate. The organic layer was dried over sodium sulfate and concentrated. The residue was purified by amine gel column chromatography (hexane-ethyl acetate, gradient) to give the title compound (476 mg, 87%) as an amorphous.

MS (ESI) m/z 457 (M+H)$^+$.

Step B

N,N-dimethyl-2-(5-(1-(methylsulfonyl)azetidin-3-ylsulfonyl)-2-neopentyl-1H-benzo[d]imidazol-1-yl)ethanamine citrate

[Chem. 89]

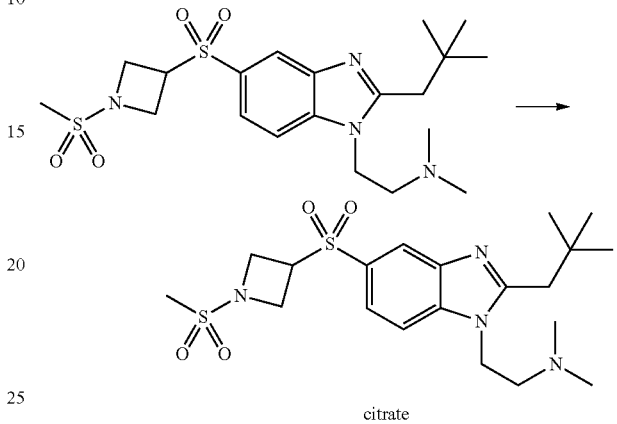

citrate

To a solution of citric acid (200 mg, 1.04 mmol) in methanol (3 mL) was added N,N-dimethyl-2-(5-(1-(methylsulfonyl)azetidin-3-ylsulfonyl)-2-neopentyl-1H-benzo[d]imidazol-1-yl)ethanamine (STEP A, 476 mg, 1.04 mmol) and the mixture was concentrated in vacuo. To the residual amorphous was added ethanol (10 mL) and methanol at 60° C. until the solid was dissolved. The solution was cooled to room temperature and the precipitate was filtered. The white solid was dried under reduced pressure to give the title compound (525 mg, 78%).

$^1$H-NMR (300 MHz, DMSO-d6) δ: 8.20 (d, J=1.7Hz, 1H), 7.85 (d, J=8.3 Hz, 1H), 7.78 (dd, J=8.3 Hz, 1.7 Hz, 1H), 4.59-4.42 (m, 3H), 4.23-4.18 (m, 2H), 4.11-4.05 (m, 2H), 3.07 (s, 3H), 2.87-2.77 (m, 4H), 2.69 (d, J=14.6 Hz, 2H), 2.59 (d, J=14.6 Hz, 2H), 2.41 (s, 6H), 1.09 (s, 9H), peaks of COOH and OH group were not observed.

MS (ESI) m/z 457 (M+H)$^+$.

Example 20

(4-((1-(2-(dimethylamino)ethyl)-2-neopentyl-1H-benzo[d]imidazol-5-ylsulfonyl)methyl)piperidin-1-yl)(1H-pyrazol-4-yl)methanone hydrochloride

[Chem. 90]

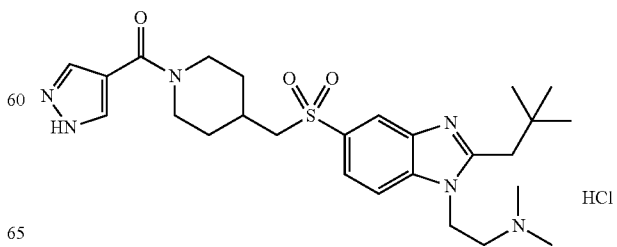

Step A tert-butyl 4-((1-(2-(dimethylamino)ethyl)-2-neopentyl-1H-benzo[d]imidazol-5-ylthio)methyl)piperidine-1-carboxylate

[Chem. 91]

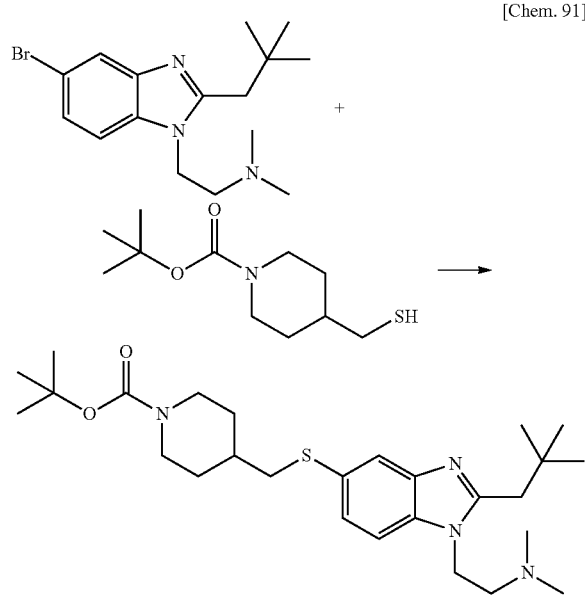

A mixture of 2-(5-bromo-2-neopentyl-1H-benzo[d]imidazol-1-yl)-N,N-dimethylethanamine (prepared in STEP A of Example 1, 1.41 g, 4.15 mmol), tert-butyl 4-(mercaptomethyl)piperidine-1-carboxylate (prepared in STEP B of Example 5, 1.20 g, 5.19 mmol), 4,5-bis(diphenylphosphino)-9,9-dimethylxanthene (120 mg, 0.208 mmol), tris(dibenzylideneacetone)dipalladium(0) (95.2 mg, 0.104 mmol) and N,N-diisopropylethylamine (1.09 mL, 6.23 mmol) in 1,4-dioxane (8.5 mL) was stirred at 130° C. for 18 h. The mixture was filtered through a celite and the filtrate was concentrated in vacuo. The residue (2.40 g) was used for the next step without purification.

MS (ESI) m/z 489 (M+H)⁺.

Step B tert-butyl 4-((1-(2-(dimethylamino)ethyl)-2-neopentyl-1H-benzo[d]imidazol-5-ylsulfonyl)methyl)piperidine-1-carboxylate

[Chem. 92]

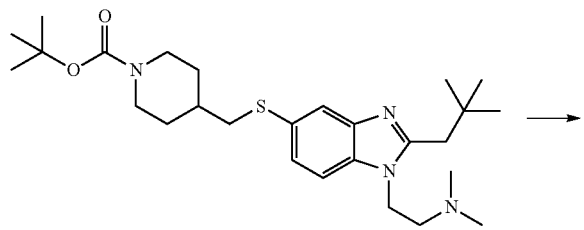

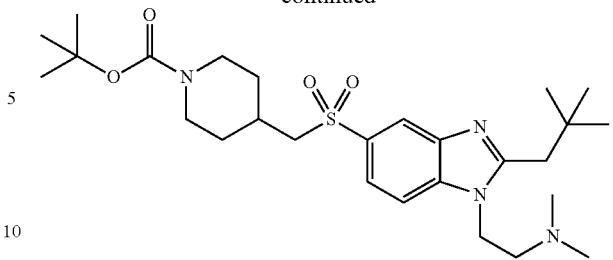

To a solution of tert-butyl 4-((1-(2-(dimethylamino)ethyl)-2-neopentyl-1H-benzo[d]imidazol-5-ylthio)methyl)piperidine-1-carboxylate (STEP A, 2.40 g of crude mixture, c.a. 4.15 mmol) in methanol (15 mL) were added methanesulfonic acid (798 mg, 8.30 mmol), 30% hydrogen peroxide aqueous solution (1.82 mL, 17.9 mmol) and sodium tungstate dihydrate (68.6 mg, 0.208 mmol) at room temperature. The resulting mixture was stirred for 2 h, and to the mixture were added sodium thiosulfate aqueous solution and sodium bicarbonate aqueous solution and diluted with dichloromethane to separate. The organic layer was concentrated in vacuo. The residue was purified by silica gel column chromatography (pre-treatment with triethylamine, dichloromethane-ethyl acetate, gradient) to give the title compound (1.48 g, 68%) as a dark orange grease.

MS (ESI) m/z 521 [M+H]⁺.

¹H-NMR (300 MHz, CDCl₃) δ: 8.29 (br, 1H), 7.79 (dd, J=8.0, 1.5 Hz, 1H), 7.46 (d, J=8.0 Hz, 1H), 4.35-4.30 (m, 2H), 4.05-4.01 (m, 2H), 3.05 (d, J=6.6 Hz, 2H), 2.85 (s, 2H), 2.80-2.53 (m, 4H), 2.32 (s, 6H), 2.20-2.03 (m, 1H), 1.90-1.86 (m, 2H), 1.44 (s, 9H), 1.30-1.16 (m, 2H), 1.11 (s, 9H).

Step C

N,N-dimethyl-2-(2-neopentyl-5-(piperidin-4-ylmethylsulfonyl)-1H-benzo[d]imidazol-1-yl)ethanamine

[Chem. 93]

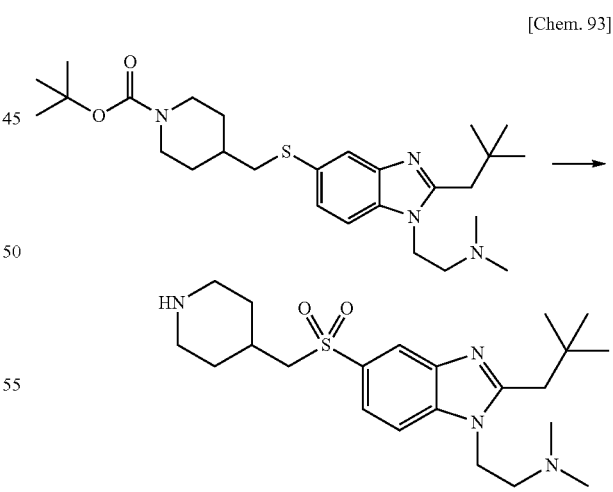

A mixture of tert-butyl 4-((1-(2-(dimethylamino)ethyl)-2-neopentyl-1H-benzo[d]imidazol-5-ylsulfonyl)methyl)piperidine-1-carboxylate (STEP B, 1.48 g, 2.84 mmol) and chlorotrimethylsilane (1.45 mL, 11.4 mmol) in methanol (5 mL) was stirred at 50° C. for 1.5 h. The reaction mixture was concentrated in vacuo, followed by addition of dichloromethane (100 ml). The resulting mixture was washed with sodium bicarbonate aqueous solution and brine and dried over sodium sulfate. The resulting solution was concentrated and the residue was purified by silica gel column chromatography (pre-treatment with triethylamine, dichloromethane-ethyl acetate=100:0 to 0:100) to give the title compound (1.18 g, 84%).

MS (ESI) m/z 421 (M+H)⁺.

Step D (4-((1-(2-(dimethylamino)ethyl)-2-neopentyl-1H-benzo[d]imidazol-5-ylsulfonyl)methyl)piperidin-1-yl)(1H-pyrazol-4-yl)methanone

[Chem. 94]

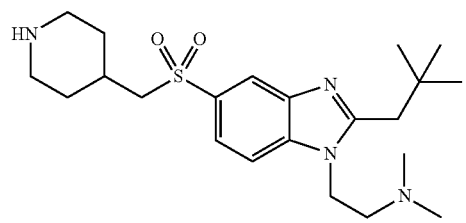

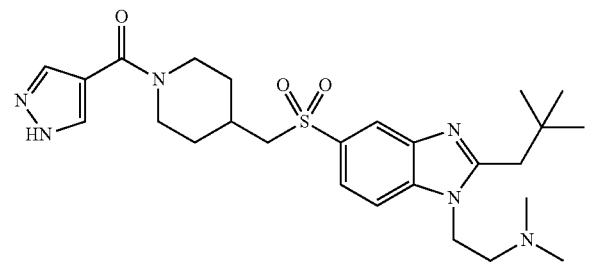

To a solution of N,N-dimethyl-2-(2-neopentyl-5-(piperidin-4-ylmethylsulfonyl)-1H-benzo[d]imidazol-1-yl) ethanamine (STEP C, 687 mg, 1.63 mmol) in dichloromethane (8 mL) were added triethylamine (230 microL, 1.63 mmol), 1H-pyrazole-4-carboxylic acid (201 mg, 1.80 mmol) and O-benzo-triazole-N,N,N',N'-tetramethyl-uronium-hexafluoro-phosphate (638 mg, 1,68 mmol) at room temperature. After 2 h, the mixture was diluted with dichloromethane (80 mL) and washed with sodium bicarbonate aqueous solution and brine. The organic layer was dried over magnesium sulfate and concentrated in vacuo. The residue was purified by amine gel column chromatography (ethyl acetate-methanol, gradient) to give the title compound (757 mg, 90%) as a pale yellow grease.

MS (ESI) m/z 515 (M+H)⁺.

Step E (4-((1-(2-(dimethylamino)ethyl)-2-neopentyl-1H-benzo[d]imidazol-5-ylsulfonyl)methyl)piperidin-1-yl)(1H-pyrazol-4-yl)methanone hydrochloride

[Chem. 95]

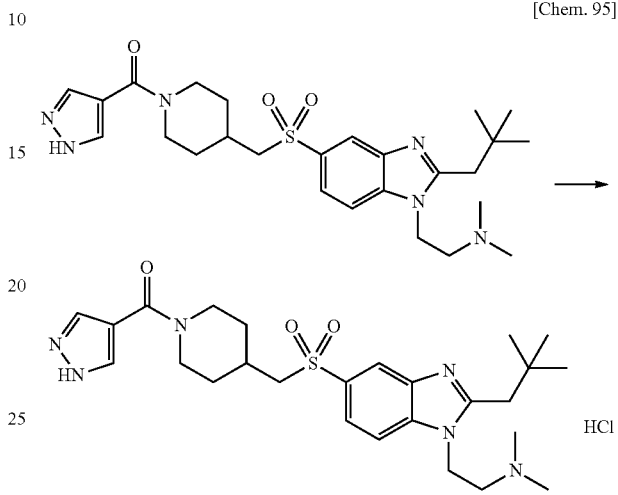

To a solution of (4-((1-(2-(dimethylamino)ethyl)-2-neopentyl-1H-benzo[d]imidazol-5-ylsulfonyl)methyl)piperidin-1-yl)(1H-pyrazol-4-yl)methanone (STEP D, 450 mg, 0.874 mmol) in ethanol (2 mL) was added 4 mol/L hydrogen chloride in ethyl acetate solution (215 microL, 0.869 mmol). To the resulting suspension was added methanol (2 mL) and the whole was heated at 85° C. for 20 min. The resulting suspension was cooled to 0° C. The white solid was isolated with filtration, to give the title compound (182 mg, 38%) as a white solid.

MS (ESI) m/z 515 (M+H)⁺.

¹H-NMR (300 MHz, DMSO-d6) δ: 8.14 (s, 1H), 8.00 (br, 1H), 7.94 (d, J=8.8 Hz, 1H), 7.79 (dd, J=8.8 Hz, 1.6 Hz, 1H), 7.65 (br, 1H), 4.73 (br, 2H), 4.40-4.00 (m, 2H), 3.50-3.00 (m, 2H), 2.90 (s, 2H), 2.95-2.70 (br, 4H), 2.51 (s, 6H), 2.09 (br, 1H), 1.87-1.79 (m, 2H), 1.30-1.17 (m, 2H), 1.09 (s, 9H), peaks of NH group was not observed.

Example 21

(S)—N,N-dimethyl-2-(5-(1-methylpyrrolidin-3-ylsulfonyl)-2-neopentyl-1H-benzo[d]imidazol-1-yl) ethanamine dihydrochloride

[Chem. 96]

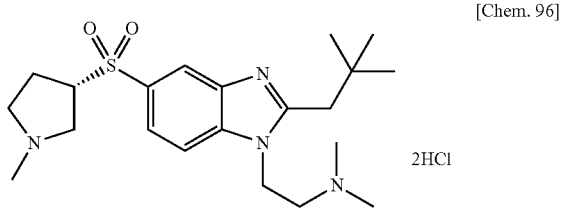 [SMILES: CN(C)CCn1c(CC(C)(C)C)nc2cc(S(=O)(=O)[C@H]3CCN(C)C3)ccc21]

Step A (R)-tert-butyl 3-hydroxypyrrolidine-1-carboxylate

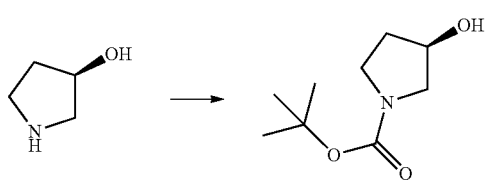

[Chem. 97]

To a solution of (R)-3-pyrrolidinol (4.96 g, 57.0 mmol) in dichloromethane (130 mL) was added triethylamine (10.9 mL, 78.0 mmol) and di-tert-butyl dicarbonate (11.3g 51.8 mmol) in dichloromethane (20 mL) at room temperature. After 1 h, the mixture was washed with 1 mol/L hydrochloric acid (100 mL) and brine, dried over sodium sulfate and concentrated to give the title compound (9.07 g, 94%) as a colorless oil.

$^1$H-NMR (300 MHz, CDCl$_3$) δ: 4.49-4.42 (m, 1H), 3.55-3.26 (m, 4H), 2.06-1.85 (m, 3H), 1.46 (s, 9H).

Step B (S)-tert-butyl 3-(acetylthio)pyrrolidine-1-carboxylate

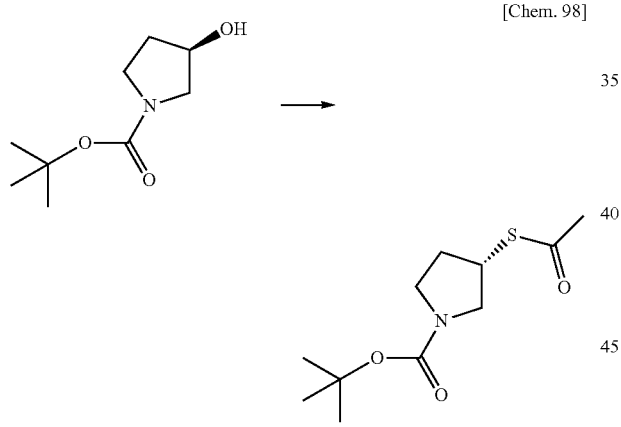

[Chem. 98]

To a solution of (R)-tert-butyl 3-hydroxypyrrolidine-1-carboxylate (STEP A, 2.25 g, 12.0 mmol) and triethylamine (2.53 mL, 18.0 mmol) in tetrahydrofuran (30 mL) was added methanesulfonyl chloride (1.12 mL, 14.4 mmol) in tetrahydrofuran (5 mL) at 0° C. After stirring at room temperature for 1 h, the precipitate was filtered off and the filtrate was concentrated in vacuo.

The residue was diluted with dimethyl formamide (40 mL). To this solution were added potassium carbonate (2.16 g, 15.6 mmol) and thioacetic acid (2.16 mL, 30.0 mmol). The mixture was stirred at 80° C. for 2 h. The mixture was diluted with diethyl ether (100 mL) and water (30 mL) to separate. The organic layer was washed with water (50 mL×2), dried over sodium sulfate and concentrated in vacuo. The residue was purified by silica gel column chromatography (hexane-ethyl acetate, gradient) to give the title compound (1.82 g, 41%) as an orange oil.

MS (ESI) m/z 246 (M+H)$^+$.

Step C (S)-tert-butyl 3-mercaptopyrrolidine-1-carboxylate

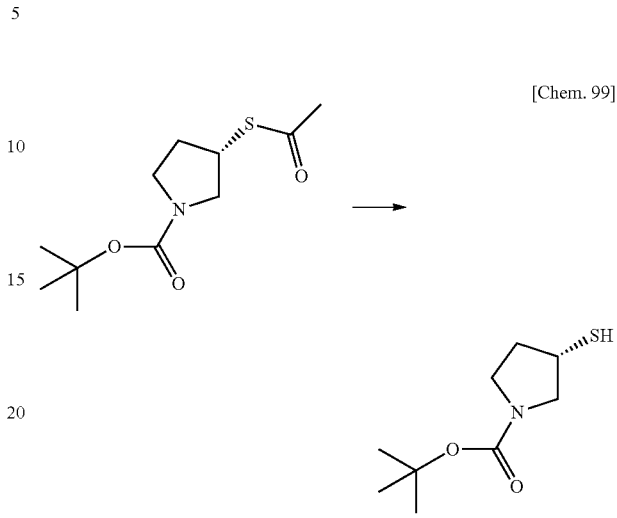

[Chem. 99]

To a solution of (S)-tert-butyl 3-(acetylthio)pyrrolidine-1-carboxylate (STEP B, 1.82 g, 7.42 mmol) in methanol (15 mL) was added potassium carbonate (2.05 g, 14.8 mmol). The mixture was stirred at 50° C. for 2 h. Then the mixture was cooled to room temperature, acidified by addition of 20% citric acid aqueous solution and concentrated in vacuo to remove methanol. The residue was diluted with ethyl acetate to separate. The organic layer was dried over sodium sulfate and concentrated in vacuo. The crude product was used for the next step without purification.

MS (ESI) m/z 202 (M−H)$^−$.

Step D (S)-tert-butyl 3-(1-(2-(dimethylamino)ethyl)-2-neopentyl-1H-benzo[d]imidazol-5-ylthio)pyrrolidine-1-carboxylate

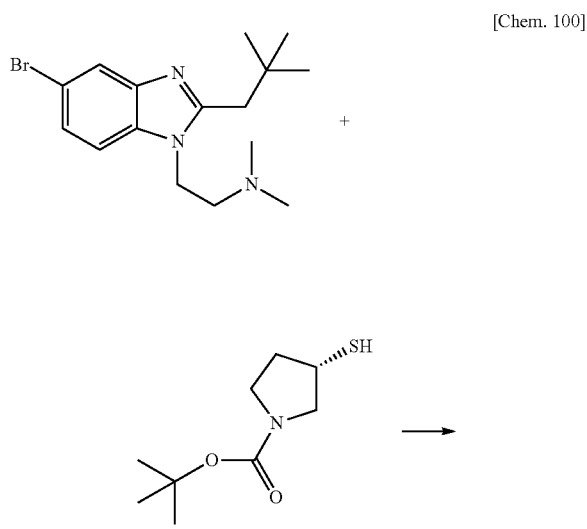

[Chem. 100]

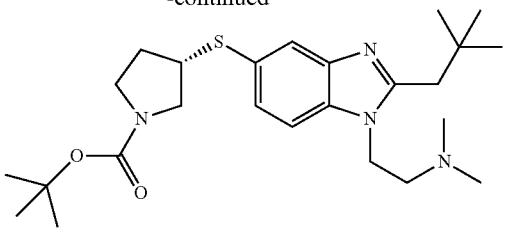

A mixture of 2-(5-bromo-2-neopentyl-1H-benzo[d]imidazol-1-yl)-N,N-dimethylethanamine (prepared in STEP A of Example 1, 1.93 g, 5.69 mmol), (S)-tert-butyl 3-mercaptopyrrolidine-1-carboxylate (STEP C, 7.42 mmol), 4,5-bis(diphenylphosphino)-9,9-dimethylxanthene (165 mg, 0.285 mmol), tris(dibenzylideneacetone)dipalladium(0) (130 mg, 0.142 mmol) and N,N-diisopropylethylamine (1.10 g, 8.54 mmol) in 1,4-dioxane (25 mL) was stirred at 130° C. for 18 h. The mixture was concentrated and the residue was purified by silica gel column chromatography (pre-treatment with triethylamine, hexane-ethyl acetate, gradient) to give the title compound (1.83 g, 70%) as a brown oil.

MS (ESI) m/z 461 (M+H)+.

Step E (S)-tert-butyl 3-(1-(2-(dimethylamino)ethyl)-2-neopentyl-1H-benzo[d]imidazol-5-ylsulfonyl)pyrrolidine-1-carboxylate

[Chem. 101]

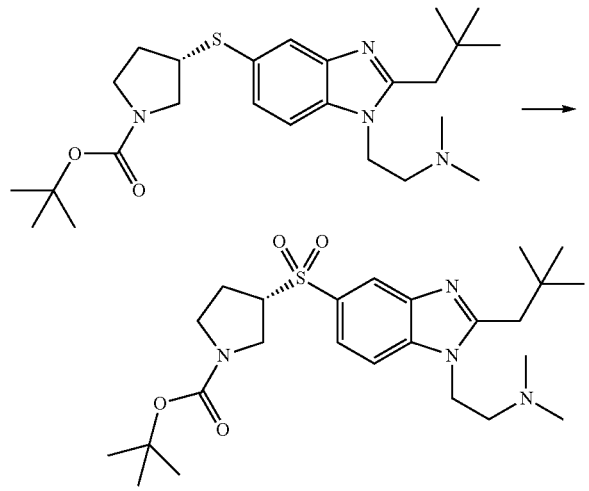

To a solution of (S)-tert-butyl 3-(1-(2-(dimethylamino)ethyl)-2-neopentyl-1H-benzo[d]imidazol-5-ylthio)pyrrolidine-1-carboxylate (STEP D, 1.83 g, 3.98 mmol) in methanol (30 mL) were added methanesulfonic acid (516 microL, 7.95 mmol), 30% hydrogen peroxide aqueous solution (1.42 mL, 13.9 mmol) and sodium tungstate dihydrate (65.6 mg, 0.199 mmol) at room temperature and stirred for 16 h. The resulting mixture was added sodium thiosulfate aqueous solution and sodium bicarbonate aqueous solution and diluted with dichloromethane to separate. The organic layer was concentrated in vacuo and the residue was purified by amine gel column chromatography (hexane-ethyl acetate, gradient) to give the title compound (1.73 g, 3.60 mmol). Product was purified by recrystallization from a mixture of ethyl acetate and hexane to give the title compound (1.28 g, 65%) as a white solid.

MS (ESI) m/z 493 (M+H)+.

Step F (S)—N,N-dimethyl-2-(2-neopentyl-5-(pyrrolidin-3-ylsulfonyl)-1H-benzo[d]imidazol-1-yl)ethanamine

[Chem. 102]

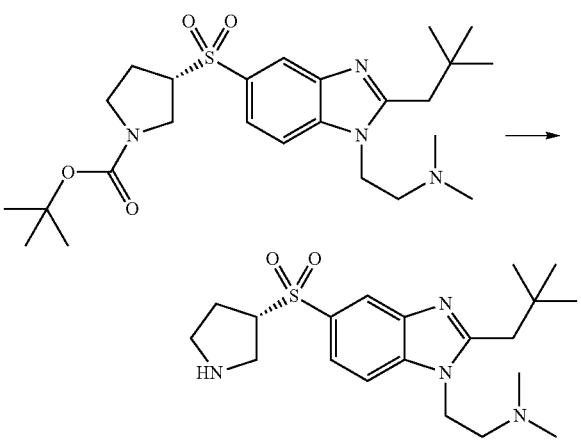

To a solution of (S)-tert-butyl 3-(1-(2-(dimethylamino)ethyl)-2-neopentyl-1H-benzo[d]imidazol-5-ylsulfonyl)pyrrolidine-1-carboxylate (STEP E, 980 mg, 1.99 mmol) in methanol (6 mL) was added chlorotrimethylsilane (1.27 mL, 9.95 mmol). The mixture was stirred at 50° C. for 16 h. The resulting mixture was concentrated. The residue was added 2 mol/L sodium hydroxide aqueous solution to pH>7 and the mixture was extracted with ethyl acetate (150 mL). The organic layer was washed with brine and dried over sodium sulfate. The resulting solution was concentrated to give the title compound (776 mg, 99%) as an oil.

MS (ESI) m/z 393 (M+H)+.

Step G (S)—N,N-dimethyl-2-(5-(1-methylpyrrolidin-3-ylsulfonyl)-2-neopentyl-1H-benzo[d]imidazol-1-yl)ethanamine

[Chem. 103]

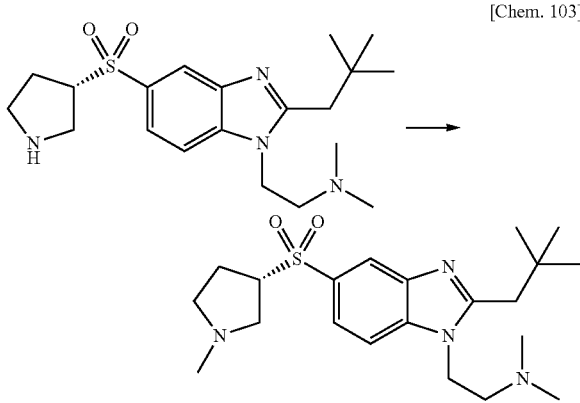

To solution of (S)—N,N-dimethyl-2-(2-neopentyl-5-(pyrrolidin-3-ylsulfonyl)-1H-benzo[d]imidazol-1-yl)ethanamine (STEP F, 776 mg, 1.98 mmol) in 1,4-dioxane (5 mL) were added 37% formalin (588 microL, 7.31 mmol) and formic acid (379 microL, 9.88 mmol). The mixture was stirred at 60° C. for 1 h. The mixture was concentrated in vacuo. The residue was diluted with saturated sodium bicarbonate aqueous solution (4 mL) and extracted with ethyl acetate (60 mL×2). The combined organic layers were washed with brine and dried over sodium sulfate. The resulting solution was concentrated in vacuo and residue was purified by amine gel column chromatography (dichloromethane-ethyl acetate, gradient) to give the title compound (704 mg, 87%) as clear grease.

MS (ESI) m/z 407 (M+H)$^+$, 405 (M−H)$^−$.

$^1$H-NMR (300 MHz, CDCl$_3$) δ: 8.29 (br, 1H), 7.78 (dd, J=8.8 Hz, 1.5 Hz, 1H), 7.46 (d, J=8.8 Hz, 1H), 4.33-4.26 (m, 2H), 3.84-3.73 (m, 1H), 2.86-2.83 (m, 4H), 2.74-2.49 (m, 4H), 2.41-2.32 (m, 1H), 2.34 (s, 3H), 2.32 (s, 6H), 2.15-2.03 (m, 1H), 1.12 (s, 9H).

Step H (S)—N,N-dimethyl-2-(5-(1-methylpyrrolidin-3-ylsulfonyl)-2-neopentyl-1H-benzo[d]imidazol-1-yl)ethanamine dihydrochloride

[Chem. 104]

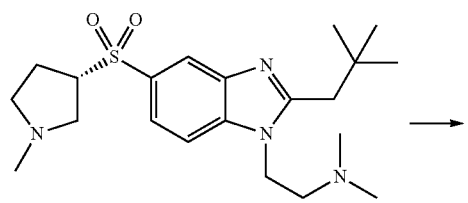

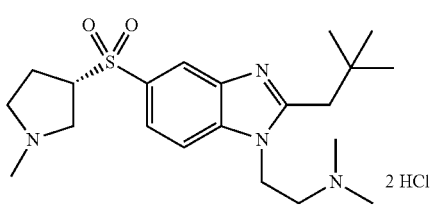

(S)—N,N-dimethyl-2-(5-(1-methylpyrrolidin-3-ylsulfonyl)-2-neopentyl-1H-benzo[d]imidazol-1-yl)ethanamine (STEP G, 704 mg, 1.73 mmol) was dissolved in ethanol (2 mL). The resulting solution was added 4 mol/L hydrogen chloride in ethyl acetate solution (857 microL, 3.43 mmol) at room temperature. The whole was concentrated in vacuo. The resulting solid was recrystallized from ethanol (4 mL) to give the title compound (413 mg, 50%).

MS (ESI) m/z 407 (M+H)$^+$.

Example 22

2-(5-(1-ethylazetidin-3-ylsulfonyl)-2-neopentyl-1H-benzo[d]imidazol-1-yl)-N,N-dimethylethanamine

[Chem. 105]

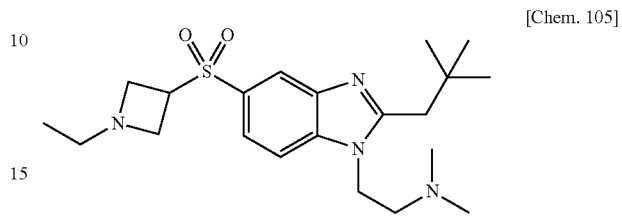

Step A 2-(5-(azetidin-3-ylsulfonyl)-2-neopentyl-1H-benzo[d]imidazol-1-yl)-N,N-dimethylethanamine

[Chem. 106]

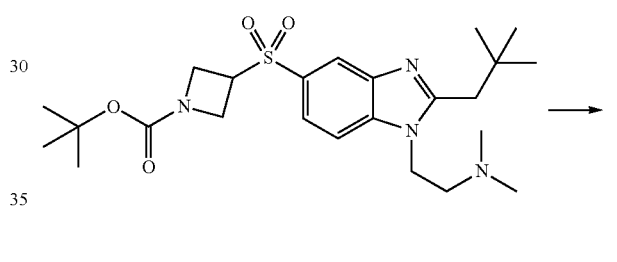

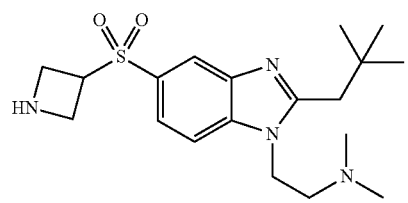

To a solution of tert-butyl 3-(1-(2-(dimethylamino)ethyl)-2-neopentyl-1H-benzo[d]imidazol-5-ylsulfonyl)azetidine-1-carboxylate (prepared in STEP F of Example 1, 327 mg, 0.683 mmol) in methanol (4 mL) was added chlorotrimethylsilane (873 microL, 6.80 mmol). After stirring for 20 h at room temperature, the mixture was concentrated in vacuo. The residue was diluted with methanol (10 mL) and filtered through SCX column. The column was washed with 1 mol/L ammonia in methanol solution to wash out the product. The filtrated was concentrated to give the title compound (270 mg, 97%) as an oil.

MS (ESI) m/z 379 (M+H)$^+$.

Step B 2-(5-(1-ethylazetidin-3-ylsulfonyl)-2-neopentyl-1H-benzo[d]imidazol-1-yl)-N,N-dimethylethanamine

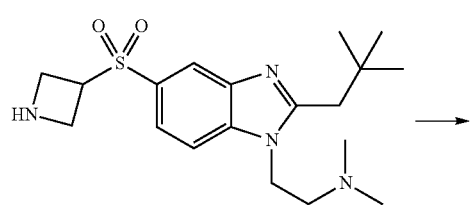

[Chem. 107]

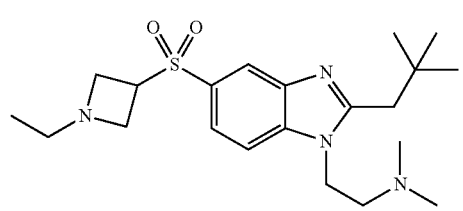

To a mixture of 2-(5-(azetidin-3-ylsulfonyl)-2-neopentyl-1H-benzo[d]imidazol-1-yl)-N,N-dimethylethanamine (STEP A, 25 mg, 0.066 mmol), acetic acid (11 microL, 0.20 mmol) and acetaldehyde (75 microL, 1.3 mmol) in dichloromethane (1 mL) and methanol (0.5 mL) was added sodium triacetoxyborohydride (28 mg, 0.13 mmol) at room temperature. After 1 h, the mixture was concentrated. The residue was diluted with methanol (4 mL). The solution was filtered through SCX column and the column was washed with 1 mol/L ammonia in methanol solution (2 mL×2) to wash out the desired compound. The filtrate was concentrated in vacuo. The residue was purified by prep-LC-MS ("process A").

MS (ESI) m/z 407

Example 23

2-(3-(1-(2-(dimethylamino)ethyl)-2-neopentyl-1H-benzo[d]imidazol-5-ylsulfonyl)azetidin-1-yl)ethanol

[Chem. 108]

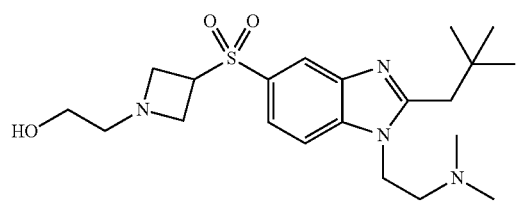

Step A 2-(3-(1-(2-(dimethylamino)ethyl)-2-neopentyl-1H-benzo[d]imidazol-5-ylsulfonyl)azetidin-1-yl)ethanol

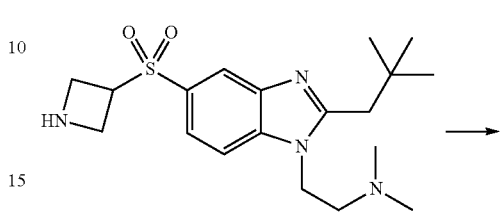

[Chem. 109]

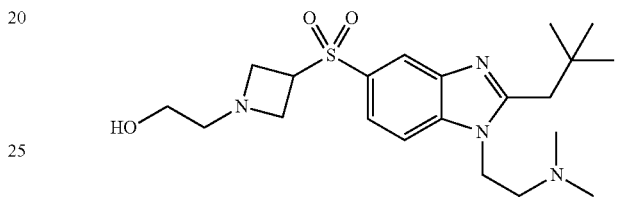

A mixture of 2-(5-(azetidin-3-ylsulfonyl)-2-neopentyl-1H-benzo[d]imidazol-1-yl)-N,N-dimethylethanamine (prepared in STEP A of Example 22, 554 mg, 1.46 mmol), triethylamine (226 microL, 1.61 mmol) and 2-chloroethanol (3.53 g, 43.9 mmol) was stirred at 60° C. for 9 h. The resulting mixture was diluted with water (30 mL) and extracted with dichloromethane (50 mL×3). The organic layer was dried over sodium sulfate and concentrated in vacuo. The crude product was purified by reverse phase HPLC (0.4% aqueous ammonia-acetonitrile=96:4 to 4:96) to give the title compound (238 mg, 39%) as a clear grease.

MS (ESI) m/z 423 (M+H)$^+$.

$^1$-NMR (300 MHz, CDCl$_3$) δ: 8.27 (br, 1H), 7.76 (dd, J=8.8 Hz, 1.5 Hz, 1H), 7.46 (d, J=8.8 Hz, 1H), 4.33-4.26 (m, 2H), 4.09-3.99 (m, 1H), 3.65-3.54 (m, 4H), 3.52-3.48 (m, 2H), 2.84 (s, 2H), 2.69-2.57 (m, 4H), 2.32 (s, 6H), 1.11 (s, 9H), OH group was not observed.

Example 24

(R)—N,N-dimethyl-2-(5-(1-methylpyrrolidin-3-ylsulfonyl)-2-neopentyl-1H-benzo[d]imidazol-1-yl)ethanamine dihydrochloride

[Chem. 110]

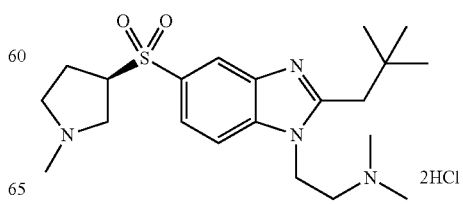

Step A (R)-tert-butyl 3-(1-(2-(dimethylamino)ethyl)-2-neo-pentyl-1H-benzo[d]imidazol-5-ylthio)pyrrolidine-1-carboxylate

[Chem. 111]

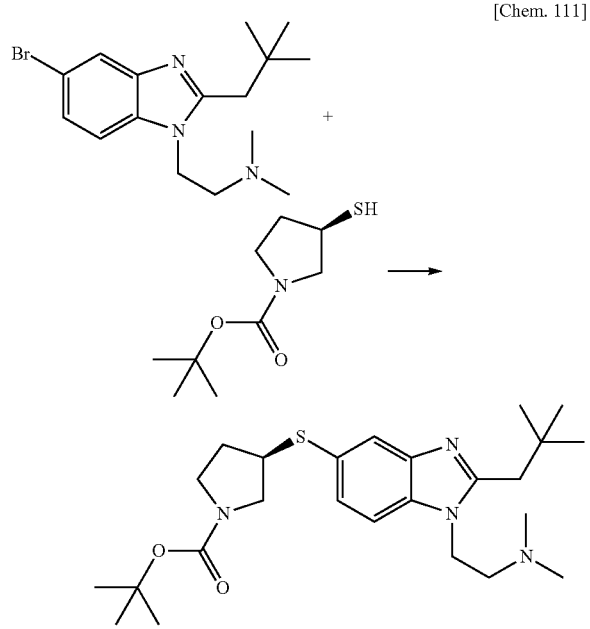

A mixture of 2-(5-bromo-2-neopentyl-1H-benzo[d]imidazol-1-yl)-N,N-dimethylethanamine (prepared in STEP A of Example 1, 937 mg, 2.77 mmol), (R)-tert-butyl 3-mercaptopyrrolidine-1-carboxylate (prepared in STEP C of Example 18, c.a. 3.60 mmol), 4,5-bis(diphenylphosphino)-9,9-dimethylxanthene (80.1 mg, 0.138 mmol), tris(dibenzylideneacetone)dipalladium(0) (63.1 mg, 0.0690 mmol) and N,N-diisopropylethylamine (725 microL, 4.15 mmol) in 1,4-dioxane (15 mL) was stirred at 160° C. for 1 h under microwave. The mixture was concentrated in vacuo and the residue was purified by amine gel column chromatography (hexane-ethyl acetate, gradient) to give the title compound (802 mg, 63% mmol) as a pale orange gum.

MS (ESI) m/z 461 (M+H)⁺.

Step B (R)-tert-butyl 3-(1-(2-(dimethylamino)ethyl)-2-neo-pentyl-1H-benzo[d]imidazol-5-ylsulfonyl)pyrrolidine-1-carboxylate

[Chem. 112]

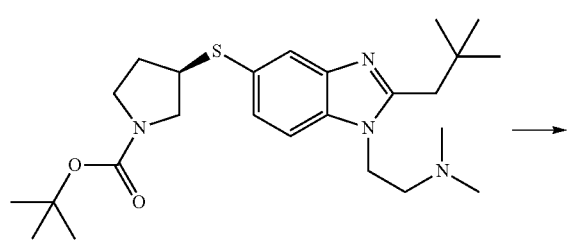

-continued

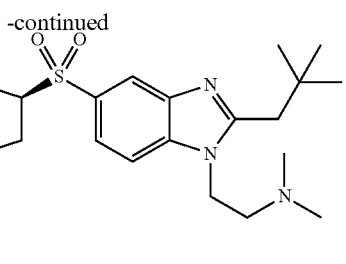

To a solution of (R)-tert-butyl 3-(1-(2-(dimethylamino)ethyl)-2-neopentyl-1H-benzo[d]imidazol-5-ylthio)pyrrolidine-1-carboxylate (STEP A, 802 mg, 1.74 mmol) in methanol (15 mL) was added methane-sulfonic acid (226 microL, 3.46 mmol), 30% hydrogen peroxide solution (622 microL, 6.09 mmol) and sodium tungstate dihydrate (28.7 mg, 0.0870 mmol) in water solution (0.5 mL) at 0° C. The resulting solution was stirred at room temperature for 5 h. The reaction mixture was added sodium thiosulfate aqueous solution and sodium bicarbonate aqueous solution and diluted with dichloromethane to separate. The organic layer was concentrated in vacuo. The residue was purified by amine gel column chromatography (hexane-ethyl acetate, gradient) to give the title compound (612 mg, 71%).

MS (ESI) m/z 493 (M+H)⁺.

Step C (R)—N,N-dimethyl-2-(2-neopentyl-5-(pyrrolidin-3-ylsulfonyl)-1H-benzo[d]imidazol-1-yl)ethanamine

[Chem. 113]

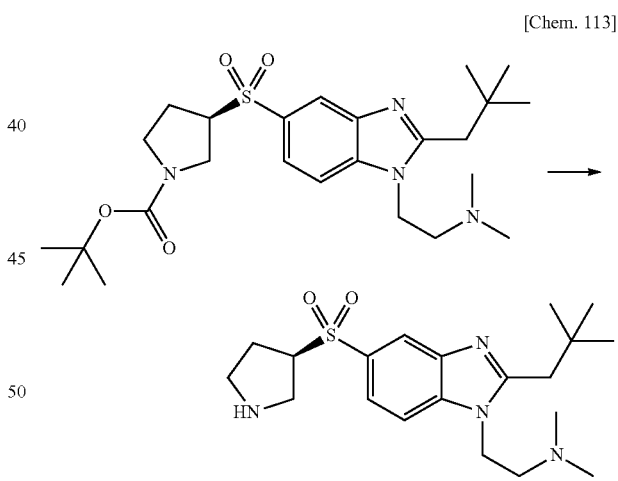

To a solution of (R)-tert-butyl 3-(1-(2-(dimethylamino)ethyl)-2-neopentyl-1H-benzo[d]imidazol-5-ylsulfonyl)pyrrolidine-1-carboxylate (STEP B, 612 mg, 1.24 mmol) in methanol (5 mL) was added chlorotrimethylsilane (749 microL, 6.21 mmol). The mixture was stirred at 50° C. for 3 h. The mixture was concentrated in vacuo. To the residue was added 2 mol/L sodium hydroxide aqueous solution to pH>7 and the mixture was extracted with ethyl acetate (150 mL). The organic layer was washed with brine and dried over sodium sulfate. The resulting solution was concentrated to give the title compound (453 mg, 93%) as an oil.

MS (ESI) m/z 393 (M+H)⁺.

Step D (R)—N,N-dimethyl-2-(5-(1-methylpyrrolidin-3-yl-
sulfonyl)-2-neopentyl-1H-benzo[d]imidazol-1-yl)
ethanamine

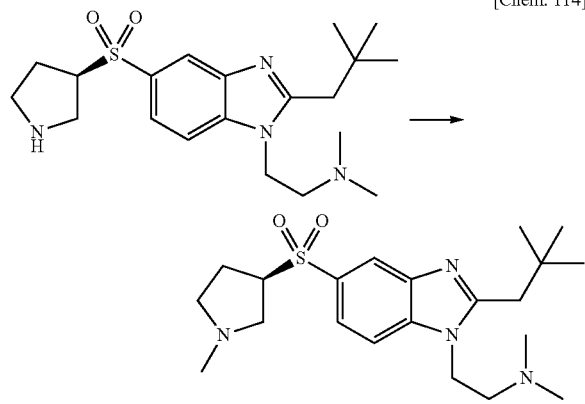

[Chem. 114]

To a solution of (R)—N,N-dimethyl-2-(2-neopentyl-5-(pyrrolidin-3-ylsulfonyl)-1H-benzo[d]imidazol-1-yl)ethanamine (STEP C, 453 mg, 1.15 mmol) in 1,4-dioxane (5 mL) was added 37% formalin (343 microL, 4.27 mmol) and formic acid (221 microL, 5.77 mmol) at 0° C. The mixture was stirred at 45° C. for 1 h. The mixture was concentrated in vacuo. The residue was diluted with sodium bicarbonate aqueous solution and extracted with ethyl acetate (60 mL×2). The combined organic layers were washed with brine and dried over sodium sulfate. The resulting solution was concentrated and residue was purified by amine gel column chromatography (dichloromethane-ethyl acetate, gradient) to give the title compound (419 mg, 89%) as a clear grease.

MS (ESI) m/z 407 (M+H)$^+$.

$^1$H-NMR (300 MHz, CDCl$_3$) δ: 8.29 (d, J=1.5 Hz, 1H), 7.78 (dd, J=8.8 Hz, 1.5 Hz, 1H), 7.46 (d, J=8.8 Hz, 1H), 4.33-4.26 (m, 2H), 3.84-3.73 (m, 1H), 2.86-2.83 (m, 4H), 2.74-2.49 (m, 4H), 2.42-2.32 (m, 1H), 2.33 (s, 3H), 2.32 (s, 6H), 2.15-2.03 (m, 1H), 1.12 (s, 9H).

Step E (R)—N,N-dimethyl-2-(5-(1-methylpyrrolidin-3-yl-
sulfonyl)-2-neopentyl-1H-benzo[d]imidazol-1-yl)
ethanamine dihydrochloride

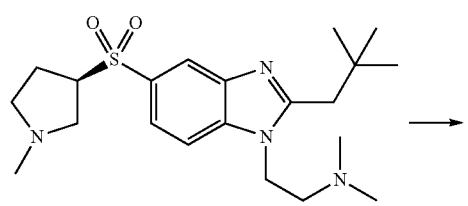

[Chem. 115]

-continued

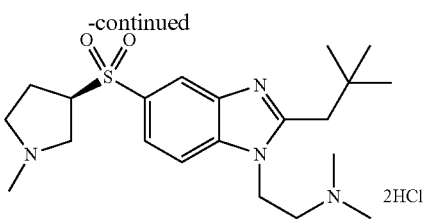

(R)—N,N-dimethyl-2-(5-(1-methylpyrrolidin-3-ylsulfonyl)-2-neopentyl-1H-benzo[d]imidazol-1-yl)ethanamine (STEP D, 419 mg, 1.03 mmol) was dissolved in ethanol (2 mL). To the resulting solution was added 4 mol/L hydrogen chloride in ethyl acetate solution (502 microL, 2.01 mmol) at room temperature. The whole was concentrated in vacuo. The resulting solid was recrystallized from a mixture of ethanol (5 mL) and ethyl acetate (1.5 mL) to give the title compound (177 mg, 36%).

MS (ESI) m/z 407 (M+H)$^+$.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the formula (I):

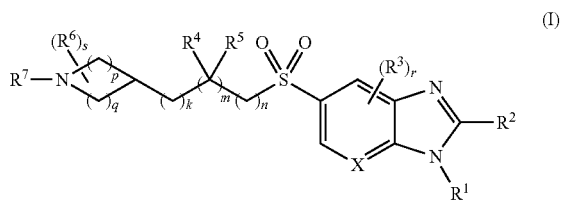

wherein:

X is carbon;

R$^1$ is C$_1$-C$_4$ alkyl optionally substituted with 1 to 2 substituents independently selected from the group consisting of C$_1$-C$_4$ alkyl, hydroxy, trifluoromethyl, trifluoromethoxy, C$_1$-C$_4$ alkoxy, amino, C$_1$-C$_4$ alkylamino, di(C$_1$-C$_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl, acyl-substituted heterocyclyl and hydroxy-substituted heterocyclyl;

R$^2$ is hydrogen, cycloalkyl, alkyl-substituted cycloalkyl, C$_3$-C$_{10}$ alkyl, alkoxy-substituted C$_3$-C$_{10}$ alkyl or C$_1$-C$_2$ alkyl; said C$_1$-C$_2$ alkyl is optionally substituted with 1 to 2 substituents independently selected from the group consisting of cycloalkyl and alkyl-substituted cycloalkyl;

R$^3$ is halogen, hydroxy, C$_1$-C$_4$ alkyl or C$_1$-C$_4$ alkoxy;

R$^4$ and R$^5$ are independently selected from the group consisting of hydrogen, halogen, hydroxy, C$_1$-C$_4$ alkyl and C$_1$-C$_4$ alkoxy; or alternatively R$^4$ and R$^5$ form a 3 to 6 membered ring;

R$^6$ is C$_1$-C$_4$ alkyl, halogen, hydroxy, hydroxy C$_1$-C$_4$ alkyl, R$^a$R$^b$N—C$_1$-C$_4$ alkyl, —CONR$^a$R$^b$, —CO$_2$C$_1$-C$_4$ alkyl or $C_1$-$C_4$ alkoxy, said $C_1$-$C_4$ alkyl is optionally substituted with 1 to 2 substituents independently selected from the group consisting of cycloalkyl and alkyl-substituted cycloalkyl; said $R^a$ and $R^b$ are independently selected from the group consisting of hydrogen, $C_1$-$C_4$ alkyl and cycloalkyl; said $C_1$-$C_4$ alkyl is optionally substituted with hydroxylamino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; or alternatively $R^a$ and $R^b$ together with nitrogen atom to which they are attached form a 5 to 6 membered ring;

k, m and n are independently selected from the group consisting of 0, 1 and 2;

p is 1 and q is 1, or p is 1 and q is 2, or p is 2 and q is 2;

r is independently selected from the group consisting of 0, 1, 2 and 3; when r is two or more than two, $R^3$ may be the same or different;

s is independently selected from the group consisting of 0, 1, 2, 3 and 4; when s is two or more than two, $R^6$ may be the same or different;

$R^7$ is $C_1$-$C_4$ alkyl, cycloalkyl, hydroxy $C_1$-$C_4$ alkyl, $R^aR^bN$—$C_1$-$C_4$ alkyl, —CO—$NR^aR^b$, —CO—($C_1$-$C_4$ alkyl), —$SO_2$—$NR^aR^b$, —$SO_2$-($C_1$-$C_4$ alkyl), heterocycle ring, or —CO-heterocycle ring;

said $C_1$-$C_4$ alkyl is optionally substituted with 1 to 2 substituents independently selected from the group consisting of $C_1$-$C_4$ alkyl, hydroxy, trifluoromethyl, trifluoromethoxy, $C_1$-$C_4$ alkoxy, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl;

said $R^a$ and $R^b$ are independently selected from the group consisting of hydrogen, $C_1$-$C_4$ alkyl, cycloalkyl, and —CO—$C_1$-$C_4$ alkyl; or alternatively $R^a$ and $R^b$ together with nitrogen atom to which they are attached form a 4 to 6 membered ring which may containing N or O;

or a pharmaceutically acceptable salt thereof.

2. The compound or the pharmaceutically acceptable salt, as claimed in claim 1, wherein:

X is carbon;

$R^1$ is $C_1$-$C_4$ alkyl optionally substituted with 1 to 2 substituents independently selected from the group consisting of $C_1$-$C_4$ alkyl, hydroxy, trifluoromethoxy, $C_1$-$C_4$ alkylamino, di($C_1$-$C_4$ alkyl)amino, cycloalkyl, alkyl-substituted heterocyclyl, acyl-substituted heterocyclyl and hydroxy-substituted heterocyclyl;

$R^2$ is tertbutyl or neopentyl;

$R^3$ is fluorine, chlorine, methyl, or ethyl;

$R^4$ and $R^5$ are independently selected from the group consisting of hydrogen, methyl and ethyl; or alternatively $R^4$ and $R^5$ form a 3 to 5 membered ring;

$R^6$ is methyl, ethyl, hydroxymethyl, —$CONH_2$, or —$CO_2$methyl;

k, m and n are independently selected from the group consisting of 0 and 1;

p is 1 and q is 1, or p is 1 and q is 2, or p is 2 and q is 2;

r is independently selected from the group consisting of 0 and 1;

s is independently selected from the group consisting of 0, 1, and 2; when s is two, $R^6$ may be the same or different;

$R^7$ is methyl, ethyl, propyl, isopropyl, butyl, isobutyl, sec-butyl, tert-butyl, hydroxyl, cyclopropyl, cyclobutyl, hydroxyethyl, 1-methylhydroxyethyl, 1,1-dimethylhydroxyethyl, dimethylaminoetyhyl, methylaminoethyl, —$CONH_2$, —CONH $C_1$-$C_4$ alkyl, —$CONR^aR^b$, —$SO_2$—$NH_2$, —$SO_2$—$NHCH_3$, —$SO_2$—$N(CH_3)_2$, —$SO_2$—$CH_3$, —$SO_2$—$C_2H_5$, heterocycle ring, or —CO—heterocycle ring; said $C_1$-$C_4$ alkyl is optionally substituted with 1 to 2 substituents independently selected from the group consisting of $C_1$-$C_4$ alkyl, hydroxy, trifluoromethyl, trifluoromethoxy, and $C_1$-$C_4$ alkoxy.

3. The compound of claim 1, which is selected from the group consisting of:

3-(1-(2-(dimethylamino)ethyl)-2-neopentyl-1H-benzo[d]imidazol-5-ylsulfonyl)azetidine-1-carboxamide;

3-(1-(2-hydroxy-2-methylpropyl)-2-neopentyl-1H-benzo[d]imidazol-5-ylsulfonyl)azetidine-1-carboxamide;

3-((1-(cyclopropylmethyl)-2-neopentyl-1H-benzo[d]imidazol-5-ylsulfonyl)methy)azetidine-1-carboxamide;

1-(cyclopropylmethyl)-5-((1-(methylsulfonyl)azetidin-3-yl)methylsulfonyl)-2-neopentyl-1H-benzo[d]imidazole;

1-(cyclopropylmethyl)-2-neopentyl-5-((1-(pyridin-4-yl)piperidin-4-yl)methylsulfonyl)-1H-benzo[d]imidazole;

2-tert-butyl-1-(cyclopropylmethyl)-5-((1-(methylsulfonyl)piperidin-4-yl)methylsulfonyl)-1H-benzo[d]imidazole;

5-(1-(methylsulfonyl)azetidin-3-ylsulfonyl)-2-neopentyl-1-(2-(trifluoromethoxy)ethyl)- 1H-benzo[d]imidazole;

3-(2-neopentyl-1-(2-(trifluoromethoxy)ethyl)-1H-benzo[d]imidazol-5-ylsulfonyl)azetidine-1-carboxamide;

1-(4-(1-(cyclopropylmethyl)-2-neopentyl-1H-benzo[d]imidazol-5-ylsulfonyl)-4-(hydroxymethyl)piperidin-1-yl)ethanone;

(4-(1-(cyclopropylmethyl)-2-neopentyl-1H-benzo[d]imidazol-5-ylsulfonyl)-1-(methylsulfonyl)piperidin-4-yl)methanol;

4-[2-(2,2-dimethylpropyl)-1-[(4-hydroxyoxan-4-yl)methyl]-1H-1,3-benzo[d]imidazole-5-sulfonyl]piperidine-1-carboxamide;

4-(4-((1-(cyclopropylmethyl)-2-neopentyl-1H-benzo[d]imidazol-5-ylsulfonyl)methyl)piperidine-1-carbonyl)imidazolidin-2-one;

4-{[1-(cyclopropylmethyl)-2-(2,2-dimethylpropyl)-1H-1,3-benzodiazole-5-sulfonyl]methyl}piperidine-1-sulfonamide;

3-(1-((1-acetylpiperidin-4-yl)methyl)-2-neopentyl-1H-benzo[d]imidazol-5-ylsulfonyl)azetidine-1-carboxamide;

1-(cyclopropylmethyl)-2-(2,2-dimethylpropyl)-5-{[(1-methanesulfonylpiperidin-4-yl)methane]sulfonyl}-1H-1,3-benzodiazole;

1-(4-{[1-(cyclopropylmethyl)-2-(2,2-dimethylpropyl)-1H-1,3-benzodiazole-5-sulfonyl]methyl}piperidin-1-yl)ethan-1-one;

1-(cyclopropylmethyl)-2-(2,2-dimethylpropyl)-5-(1-methanesulfonylazetidine-3-sulfonyl)-1H-1,3-benzodiazole;

(3R)-3[1-(cyclopropylmethyl)-2-(2,2-dimethylpropyl)-1H-1 ,3-benzodiazole-5-sulfonyl]pyrrolidine-1-carboxamide;

N,N-dimethyl-2-(5-(1-(methylsulfonyl)azetidin-3-ylsulfonyl)-2-neopentyl-1H-benzo[d]imidazol-1-yl)ethanamine citrate;

(4-((1-(2-(dimethylamino)ethyl)-2-neopentyl-1H-benzo[d]imidazol-5-ylsulfonyl)methyl)piperidin-1-yl)(1H-pyrazol-4-yl)methanone hydrochloride;

(S)—N,N-dimethyl-2-(5-(1-methylpyrrolidin-3-ylsulfonyl)-2-neopentyl-1H-benzo[d]imidazol-1-yl)ethanamine dihydrochloride;

2-(5-(1-ethylazetidin-3-ylsulfonyl)-2-neopentyl-1H-benzo[d]imidazol-1-yl)-N, N-dimethylethanamine;

2-(3-(1-(2-(dimethylamino)ethyl)-2-neopentyl-1H-benzo[d]imidazol-5-ylsulfonyl)azetidin-1-yl)ethanol; and (R)-N,N-dimethyl-2-(5-(1-methylpyrrolidin-3-ylsulfonyl)-2-neopentyl-1H-benzo[d]imidazol-1-yl)ethanamine dihydrochloride;

or a pharmaceutically acceptable salt thereof.

4. A pharmaceutical composition comprising the compound or the pharmaceutically acceptable salt thereof, as defined in any one of claims 1 to 3, and a pharmaceutically acceptable carrier.

5. The pharmaceutical composition as claimed in claim 4, further comprising another pharmacologically active agent.

6. 2-(3-(1-(2-(dimethylamino)ethyl)-2-neopentyl-1H-benzo[d]imidazol-5-ylsulfonyl)azetidin-1-yl)ethanol, or a pharmaceutically acceptable salt thereof.

\* \* \* \* \*